(12) United States Patent
Lonberg et al.

(10) Patent No.: US 10,266,591 B2
(45) Date of Patent: Apr. 23, 2019

(54) OPTIMIZATION OF ANTIBODIES THAT BIND LYMPHOCYTE ACTIVATION GENE-3 (LAG-3), AND USES THEREOF

(71) Applicant: BRISTOL-MYERS SQUIBB COMPANY, Princeton, NJ (US)

(72) Inventors: Nils Lonberg, Woodside, CA (US); Mohan Srinivasan, Cupertino, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/296,290

(22) Filed: Oct. 18, 2016

(65) Prior Publication Data

US 2017/0137514 A1     May 18, 2017

Related U.S. Application Data

(60) Division of application No. 14/093,867, filed on Dec. 2, 2013, now Pat. No. 9,505,839, which is a continuation of application No. PCT/US2013/048999, filed on Jul. 2, 2013.

(60) Provisional application No. 61/667,058, filed on Jul. 2, 2012.

(51) Int. Cl.
| | |
|---|---|
| A61K 38/36 | (2006.01) |
| A61K 39/395 | (2006.01) |
| C07K 16/28 | (2006.01) |
| A61K 45/06 | (2006.01) |
| A61K 47/68 | (2017.01) |
| C07K 16/30 | (2006.01) |
| A61K 39/00 | (2006.01) |

(52) U.S. Cl.
CPC .......... *C07K 16/2803* (2013.01); *A61K 45/06* (2013.01); *A61K 47/6849* (2017.08); *C07K 16/28* (2013.01); *C07K 16/2818* (2013.01); *C07K 16/2827* (2013.01); *A61K 39/39558* (2013.01); *A61K 2039/507* (2013.01); *C07K 16/3061* (2013.01); *C07K 2317/14* (2013.01); *C07K 2317/21* (2013.01); *C07K 2317/565* (2013.01); *C07K 2317/75* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 5,773,578 A | 6/1998 | Hercend et al. |
| 5,874,250 A | 2/1999 | Hercend et al. |
| 5,976,877 A | 11/1999 | Hercend et al. |
| 6,143,273 A | 11/2000 | Faure et al. |
| 6,197,524 B1 | 3/2001 | Romagnani |
| 6,482,925 B1 | 11/2002 | El Tayar et al. |
| RE38,313 E | 11/2003 | Faure et al. |
| 7,138,501 B2 | 11/2006 | Ruben et al. |
| 7,306,906 B2 | 12/2007 | Maruyama et al. |
| 7,329,737 B2 | 2/2008 | Sexton et al. |
| 7,563,441 B2 | 7/2009 | Graus et al. |
| 7,595,048 B2 | 9/2009 | Honjo et al. |
| 7,605,238 B2 | 10/2009 | Korman et al. |
| 7,790,160 B2 | 9/2010 | Von Strandmann et al. |
| 7,850,965 B2 | 12/2010 | Jensen et al. |
| 7,943,743 B2 | 5/2011 | Korman et al. |
| 8,008,449 B2 | 8/2011 | Korman et al. |
| 8,168,179 B2 | 5/2012 | Honjo et al. |
| 8,383,796 B2 | 2/2013 | Korman et al. |
| 8,728,474 B2 | 5/2014 | Honjo et al. |
| 8,779,105 B2 | 7/2014 | Korman et al. |
| 9,067,999 B1 | 6/2015 | Honjo et al. |

(Continued)

FOREIGN PATENT DOCUMENTS

| | | |
|---|---|---|
| JP | 2006-340714 A | 12/2006 |
| WO | 9110682 A1 | 7/1991 |

(Continued)

OTHER PUBLICATIONS

MacCallum et al. "Antibody-antigen interactions: contact analysis and binding site topography", Journal of Molecular Biology, 1996. vol. 262, pp. 732-745.*

(Continued)

*Primary Examiner* — Michail A Belyavskyi
(74) *Attorney, Agent, or Firm* — Sterne, Kessler, Goldstein & Fox P.L.L.C.

(57) ABSTRACT

The present invention provides isolated monoclonal antibodies that specifically bind LAG-3, and have optimized functional properties compared to previously described anti-LAG-3 antibodies, such as antibody 25F7 (US 2011/0150892 A1). These properties include reduced deamidation sites, while still retaining high affinity binding to human LAG-3, and physical (i.e., thermal and chemical) stability. Nucleic acid molecules encoding the antibodies of the invention, expression vectors, host cells and methods for expressing the antibodies of the invention are also provided, as well as immunoconjugates, bispecific molecules and pharmaceutical compositions comprising the antibodies. The present invention also provides methods for detecting LAG-3, as well as methods for treating stimulating immune responses using an anti-LAG-3 antibody of the invention. Combination therapy, in which the antibodies are co-administered with at least one additional immunostimulatory antibody, is also provided.

37 Claims, 15 Drawing Sheets

Specification includes a Sequence Listing.

(56) References Cited

U.S. PATENT DOCUMENTS

| | | | |
|---|---|---|---|
| 9,073,994 B2 | 7/2015 | Honjo et al. |
| 9,084,776 B2 | 7/2015 | Korman et al. |
| 9,102,725 B2 | 8/2015 | Korman et al. |
| 9,212,224 B2 | 12/2015 | Cogswell et al. |
| 9,273,135 B2 | 3/2016 | Korman et al. |
| 9,358,289 B2 | 6/2016 | Korman et al. |
| 9,387,247 B2 | 7/2016 | Korman et al. |
| 9,393,301 B2 | 7/2016 | Honjo et al. |
| 9,402,899 B2 | 8/2016 | Honjo et al. |
| 9,439,962 B2 | 9/2016 | Honjo et al. |
| 9,492,539 B2 | 11/2016 | Korman et al. |
| 9,492,540 B2 | 11/2016 | Korman et al. |
| 9,505,839 B2 | 11/2016 | Lonberg et al. |
| 9,580,505 B2 | 2/2017 | Korman et al. |
| 9,580,507 B2 | 2/2017 | Korman et al. |
| 2002/0086014 A1 | 7/2002 | Korman et al. |
| 2002/0146753 A1 | 10/2002 | Ditzel et al. |
| 2003/0059937 A1 | 3/2003 | Ruben |
| 2003/0129601 A1 | 7/2003 | Cole |
| 2004/0072164 A1 | 4/2004 | Maruyama et al. |
| 2004/0171551 A1 | 9/2004 | Triebel |
| 2005/0009136 A1 | 1/2005 | Nixon et al. |
| 2005/0226876 A1 | 10/2005 | Graus et al. |
| 2006/0110383 A1 | 5/2006 | Honjo et al. |
| 2006/0177442 A1 | 8/2006 | Von Strandmann et al. |
| 2006/0240024 A1 | 10/2006 | Pardoll et al. |
| 2007/0004910 A1 | 1/2007 | Sexton et al. |
| 2007/0160598 A1 | 7/2007 | Dennis et al. |
| 2008/0038264 A1 | 2/2008 | Bodary et al. |
| 2008/0069822 A1 | 3/2008 | Jensen et al. |
| 2008/0260641 A1 | 10/2008 | Teeling et al. |
| 2009/0055944 A1 | 2/2009 | Korman et al. |
| 2009/0217401 A1 | 8/2009 | Korman et al. |
| 2009/0297518 A1 | 12/2009 | Honjo et al. |
| 2010/0196394 A1 | 8/2010 | Pardoll et al. |
| 2011/0081341 A1 | 4/2011 | Honjo et al. |
| 2011/0150892 A1 | 6/2011 | Thudium et al. |
| 2011/0209230 A1 | 8/2011 | Korman et al. |
| 2013/0122014 A1 | 5/2013 | Korman et al. |
| 2013/0133091 A1 | 5/2013 | Korman et al. |
| 2013/0309250 A1 | 11/2013 | Cogswell et al. |
| 2014/0093511 A1 | 4/2014 | Lonberg et al. |
| 2014/0212422 A1 | 7/2014 | Korman et al. |
| 2014/0294852 A1 | 10/2014 | Korman et al. |
| 2014/0314714 A1 | 10/2014 | Honjo et al. |
| 2014/0328833 A1 | 11/2014 | Korman et al. |
| 2014/0348743 A1 | 11/2014 | Korman et al. |
| 2015/0093380 A1 | 4/2015 | Honjo et al. |
| 2015/0125463 A1 | 5/2015 | Cogswell et al. |
| 2015/0165025 A1 | 6/2015 | Korman et al. |
| 2015/0197572 A1 | 7/2015 | Honjo et al. |
| 2015/0307609 A1 | 10/2015 | Lonberg et al. |
| 2015/0337038 A1 | 11/2015 | Korman et al. |
| 2016/0075782 A1 | 3/2016 | Korman et al. |
| 2016/0090417 A1 | 3/2016 | Cogswell et al. |
| 2016/0158355 A1 | 6/2016 | Honjo et al. |
| 2016/0158356 A1 | 6/2016 | Honjo et al. |
| 2016/0222116 A1 | 8/2016 | Korman et al. |
| 2016/0326248 A1 | 11/2016 | Gutierrez et al. |
| 2016/0362495 A1 | 12/2016 | Korman et al. |
| 2017/0051060 A1 | 2/2017 | Honjo et al. |
| 2017/0088615 A1 | 3/2017 | Korman et al. |
| 2017/0158767 A1 | 6/2017 | Korman et al. |

FOREIGN PATENT DOCUMENTS

| | | | |
|---|---|---|---|
| WO | 9530750 A2 | 11/1995 |
| WO | 9703695 A1 | 2/1997 |
| WO | 9713852 A1 | 4/1997 |
| WO | 97/32733 A1 | 9/1997 |
| WO | WO 98/42752 A1 | 10/1998 |
| WO | 9858059 A1 | 12/1998 |
| WO | 0069914 A2 | 11/2000 |
| WO | 03088808 A2 | 10/2003 |
| WO | WO-2004004771 A1 | 1/2004 |
| WO | 2004039956 A2 | 5/2004 |
| WO | 2005034733 A2 | 4/2005 |
| WO | 2005059106 A2 | 6/2005 |
| WO | 2006007850 A1 | 1/2006 |
| WO | WO-2006121168 A1 | 11/2006 |
| WO | 2008007648 A1 | 1/2008 |
| WO | 2008073160 A2 | 6/2008 |
| WO | 2008121615 A2 | 10/2008 |
| WO | 2008121616 A2 | 10/2008 |
| WO | 2008132601 A1 | 11/2008 |
| WO | 2010019570 A2 | 2/2010 |
| WO | 2011008092 A2 | 1/2011 |
| WO | 2012/009442 A2 | 1/2012 |
| WO | 2012054438 A1 | 4/2012 |
| WO | WO-2013173223 A1 | 11/2013 |
| WO | 2014008218 A1 | 1/2014 |
| WO | 2014140180 A1 | 9/2014 |
| WO | 2015-016718 A1 | 2/2015 |
| WO | 2015042246 A1 | 3/2015 |
| WO | 2015116539 A1 | 8/2015 |

OTHER PUBLICATIONS

De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*

Anonymous: "A Phase 1 Dose Escalation and Cohort Expansion Study of the Safety, Tolerability and Efficacy of Anti-LAG-3 Monoclonal Antibody (BMS-986016) Administered Alone and in Combination with Anti-PD-I Monoclonal Antibody (Nivolumab BMS-936558)in Advanced Solid Tumors," ClinicalTrials.gov archive, Jan. 23, 2014, pp. 1-5, XP055195481, Retrieved from the Internet<URL:https://clinicaltrials.gov/archive/NCT> 01968109/ 2014 01 23 [retrieved on-Jun. 12, 2015] p. 4. paragraph 5-paragraph 6.

Anonymous: "A Phase 1 Dose Escalation and Cohort Expansion Study of the Safety, Tolerability, and Efficacy of Anti-LAG-3 (BMS-986016) in Relapsed or Refractory Chronic Lymphocytic Leukemia and Lymphomas and Multiple Myeloma," ClinicalTrials. govArchive. Nov. 20, 2014, pp. 1-5, XP055195982. Retrieved from the Internet: URL:https://clinicaltrials.gov/archive/NCT02061761/ 2014 11 20 [retrieved on-Jun. 16, 2015] the whole document.

Baixeras, Elena et al., "Characterization of the Lymphocyte Activation Gene 3-Encoded Protein. A New Ligand for Human Leukocyte Antigen Class II Antigens," J. Exp. Med., vol. 176(2):327-337 (1992).

Blackburn, Shawn D. et al., "Coregulation of CD8+ T cell exhaustion by multiple inhibitory receptors during chronic viral infection," Nature Immunology, vol. 10(1):29-37 (2009).

Casati, Chiara et al., "Soluble Human LAG-3 Molecule Amplifies the in vitro Generation of Type 1 Tumor-Specific Immunity," Cancer Res., vol. 66(8):4450-4460 (2006).

Chelius, Dirk et al., "Identification and Characterization of Deamidation Sites in the Conserved Regions of Human Immunoglobulin Gamma Antibiodies," Anal. Chem., American Chemical Society, vol. 77(18): 6004-6011 (2005).

Cleland, JL et al., "The development of stable protein formulations: a close look at protein aggregation, deamidation, and oxidation, " Grit. Rev. Ther. Drug Carrier Syst., vol. 10(4):307-377 (1993).

Correia, I. et al., "Stability of IgG isotypes in serum," mAbs, vol. 2(3): 221-232 (2010).

Drake, C.G. et al., "Blocking the regulatory T cell molecule LAG-3 augments in vivo anti-tumor immunity in an autochthonous model of prostate cancer," Journal of Clinical Oncology, ASCO Annual Meeting Proceedings, vol. 24 (18S), Abstract No. 2573, 1page (2006).

El Mir, Samir et al., "A Soluble Lymphocyte Activation Gene-3 Molecule Used as a Vaccine Adjuvant Elicits Greater Humoral and Cellular Immune Responses to Both Particulate and Soluble Antigens," The Journal of Immunology, vol. 164:5583-5589 (2000).

(56) References Cited

OTHER PUBLICATIONS

Fishwild, D.M. et al., "High-avidity human IgG kappa monoclonal antibodies from a novel strain of minilocus transgenic mice.," Nature Biotechnol., vol. 14, pp. 845-851 (1996).
Goding S., et al., "Combination of adoptive cell transfer, anti-PD-L1 and anti-LAG-3 antibodies for the treatment of recurrent tumors Better with More," OncoImmunology, vol. 2 (8), 4 pages (2013).
Grosso, Joseph F. et al., "LAG-3 regulates CD8+ T cell accumulation and effector function in murine self- and tumor-tolerance systems," J. Clin. Invest., vol. 117(11):3383-3392 (2007).
Huang, Ching-Tai et al., "Role of LAG-3 in Regulatory T Cells," Immunity, vol. 21:503-513 (2004).
Huard, B. et al., "Cellular expression and tissue distribution of the human LAG-3-encoded protein, an MHC class II ligand," Immunogenetics, vol. 39(3), pp. 213-217 (1994).
Huard, Bertrand et al., "Characterization of the major histocompatibility complex class II binding site on LAG-3 protein," Proc. Natl. Acad. Sci. USA, vol. 94:5744-5749 (1997).
Huard, Bertrand et al., "Lymphocyte-activation gene 3/major histocompatibility complex class II interaction modulates the antigenic response of CD4+ T lymphocytes," Eur. J. Immunol., vol. 24(12):3216-3221 (1994).
Huard, Bertrand et al., "T cell major histocompatibility complex class II molecules down-regulate CD4+ T cell clone responses following LAG-3 binding," Eur. J. Immunol., vol. 26:1180-1186 (1996).
International Preliminary Report on Patentability, PCT/US2009/053405, dated Feb. 15, 2011, 10 pages, Inventors, Thudium, Kent, B. (US), Korman, Alan, J. (US), LeBlanc, Heidi (US), Yamanaka, Mark (US), Selby, Mark, (US), and Zens, Kyra, D. (US); Application title, "Human Antibodies That Bind Lymphocyte Activation Gene-3 (LAG-3), and Uses Thereof," Application Filing Date: Aug. 11, 2009.
International Preliminary Report on Patentability, PCT/US2014/056277, dated Mar. 22, 2016, 10 pages, Inventors, <Korman, Alan, J.; (US), Lonberg, Nils; (US), Fontana, David, J.; (US), Gutierrez, Andres, A.; (US), Selby, Mark, J.; (US), Lewis,Katherine, E.; (US), Application title, "Combination of Anti-LAG-3 Antibodies and Anti-PD-1 Antibodies to Treat Tumors," Application Filing Date: Sep. 18, 2014.
International Search Report and Written Opinion for PCT/US13/48999, 11 pages, dated Sep. 23, 2013, Inventors, Lonberg, Nils; (US) and Srinivasan, Mohan; (US), Application Title, "Optimization of Antibodies that Bind Lymphocyte Activation Gene-3 (LAG-3), and UsesThereof," Application Filing Date Jul. 2, 2013.
International Search Report and Written Opinion, PCT/US2009/053405, dated Mar. 31, 2010, 15 pages, Inventors, Thudium, Kent, B. (US), Korman, Alan, J. (US), LeBlanc, Heidi, (US), Yamanaka, Mark (US), Selby, Mark, (US), and Zens, Kyra, D. (US); Application title, "Human Antibodies That Bind Lymphocyte Activation Gene-3 (LAG-3), and Uses Thereof," Application Filing Date: Aug. 11, 2009.
International Search Report and Written Opinion, PCT/US2014/056277, dated Feb. 4, 2005, 15 pages, Inventors, Korman, Alan, J.; (US), Lonberg, Nils; (US), Fontana, David, J.; (US), Gutierrez, Andres, A.; (US), Selby, Mark, J.; (US), Lewis, Katherine,E.; (US), Application title, "Combination off Anti-LAG-3 Antibodies and Anti-PD-1 Antibodies to Treat Tumors," Application Filing Date: Sep. 18, 2014.
International Search Report and Written Opinion, PCT/US2015/012916, dated Jun. 23, 2015, 12 pages, Inventors, Gutierrez, Andres, A.; (US), Grosso, Joseph; (US)., Hill, Christopher, Mark; (US), Selby, Mark; (US), Lewis, Katherine E.; (US),Application title, "Anti-LAG-3 Antibodies to Treat Hematological Malignancies," Application Filing Date: Jan. 26, 2015.
Iouzalen, Nathalie et al., "LAP, a lymphocyte activation gene-3 (LAG-3)-associated protein that binds to a repeated EP motif in the intracellular region of LAG-3, may participate in the downregulation of the CD3/TCR activation pathway," Eur. J.Immunol., vol. 31:2885-2891 (2001).

Kocak, Ergun et al., "Combination Therapy with Anti-CTL Antigen-4 and Anti-4-1BB Antibodies Enhances Cancer Immunity and Reduces Autoimmunity," Cancer Res., vol. 66(14):7276-7284 (2006).
Kosky, AA, et al., "Multivariate analysis of the sequence dependence of asparagine deamidation rates in peptides," Pharm Res., vol. 26(11):2417-2428 (2009).
Kroon D. et al., "Identification of Sites of Degradation in a Therapeutic Monoclonal Antibody by Peptide Mapping," Pharmaceutical Research, vol. 9(11): 1386-1393 (1992).
Macon-Lemaitre, Laetitia et al., "The negative regulatory function of the lymphocyte-activation gene-3 co-receptor (CD223) on human T cells," Immunology, vol. 115:170-178 (2005).
Pardoll, D. et al., Dendritic Cells and Coregulatory Signals: Immune Checkpoint Blockade to Stimulate Immunotherapy, Cancer Immunotherapy, vol. 86(5) :257-275 (2007).
Prigent, Philippe et al., "Lymphocyte activation gene-3 induces tumor regression and antitumor immune responses," Eur. J. Immunol., vol. 29:3867-3876 (1999).
Reply to Communication from the Examining Division filed in European Application No. 13737946.7, dated Nov. 25, 2016, Inventors, Lonberg, Nils; (US) and Srinivasan, Mohan; (US), Application Title, "Optimization of Antibodies that Bind Lymphocyte Activation Gene-3 (LAG-3), and Uses Thereof," Application Filing Date: Jul. 2, 2013, 5 pages.
Robinson, Ne et al., "Molecular clocks," PNAS, vol. 98(3):944-949 (2001).
Subramanyam, Meena et al., "Soluble human lymphocyte activation gene-3 modulates allospecific T cell responses," International Immunology, vol. 10(4):679-689 (1998).
Third Party Observation for European Application No. 13737946.7, filed Oct. 7, 2016, Inventors, Lonberg, Nils; (US) and Srinivasan, Mohan; (US), Application Title, "Optimization of Antibodies that Bind Lymphocyte Activation Gene-3 (LAG-3), and Uses Thereof," Application Filing Date: Jul. 2, 2013, 17 pages.
Triebel, Frederic et al., "LAG-3, A Novel Lymphocyte Activation Gene Closely Related to CD4," J. Exp. Med., vol. 171:1393-1405 (1990).
Triebel, Frederic et al., "LAG-3: a regulator T-cell and DC responses and its use in therapeutic vaccination," Trends in Immunology, vol. 24(12):619-622 (2003).
Tsai P.K. et al., "Origin of the Isoelectric Heterogeneity of Monoclonal Immunoglobulin h1B4," Pharmaceutical Research, vol. 10(11): 1580-1586 (1993).
Turins M. et al., "Combinatorial immunotherapy: PD-1 may not be LAG-ing behind any more," OncoImmunolgy, vol. 1 (7), pp. 1172-1174 (2012).
Vlasak, J. et al., "Identification and characterization of asparagine deamidation in the light chain CDR1 of a humanized IgG1 antibody," Analytical Biochemistry, vol. 392 (2): 145-154 (2009).
Woo, S-R., et al., "Immune Inhibitory Molecules LAG-3 and PD-1 Synergistically Regulate T-cell Function to Promote Tumoral Immune Escape", Cancer Research, vol. 72(4), pp. 917-927 (2011).
Workman, C.J. et al., "Phenotypic analysis of the murine CD4-related glycoprotein, CD223 (LAG-3).," Eur. J. Immunol., vol. 32(8): 2255-2263 (2002).
Workman, Creg J. et al., "Negative Regulation of T Cell Homeostasis by Lympohocyte Activation Gene-3 (CD223)," The Journal of Immunology, vol. 174:688-695 (2005).
Supplementary European Search Report for Application No. 09807162.4, 10 pages, dated Dec. 21, 2012, Inventors: Thudium Kent B [US] Korman Alan J.[US]; LeBlanc Heidi [US]; Yamanaka Mark[US]; Selby Mark [US]; Zens Kyra D. [US] Thudium Kent B., Korman Alan J., Leblanc Heidi, Yamanaka Mark, Selby Mark, Zens Kyra D., Application Title: "Human Antibodies That Bind Lymphocyte Activation Gene-3 (LAG-3), and Uses Thereof," filed Jul. 31, 2015.
Lonberg, N. et al., "Antigen-specific human antibodies from mice comprising four distinct genetic modifications.," Nature, vol. 368(6474), pp. 856-859 (1994).
Agrawal S. et al., "Clinical pharmacokinetics (PK) of BMS-936558, a fully human anti-PD-1 monoclonal antibody," Journal of Clinical Oncology, 2012, ASCO Annual Meeting, American Society of Clinical Oncology, US, vol. 30 (Supp. 14), (2015) p. 1, XP002734393,

(56) References Cited

OTHER PUBLICATIONS

ISSN: 0732-183X Retrieved from the Internet: URL:http://meetinglibrary.asco.org/content; /98623-114 [retrieved on Jan. 13, 2015].

Cashion, M. et al., "Biomimetic Design and Performance of Polymerizable Lipids," Am Chem Res., vol. 42 (8):1016-1025 (2008).

De Pascalis, R. et al. "Grafting of "Abbreviated" Complementarity-Determining Regions Containing Specificity-Determining residues Essential for Ligand Contact to Engineer a Less Immunogenic Humanzied Monoclonal Antibody," Journal of Immunology, vol. 169:3076-3084 (2002).

Extended European Search Report, EP Application 16197459.7, dated Feb. 23, 2017, 15 pages.

MacCallum, R. et al. "Antibody-antigen interactions: contact analysis and binding site topography, " Journal of Molecular Biology, vol. 262: 732-745 (1996).

ATCC Product Data Sheet, "A3.4H2 (ATCC® HB-12319™)," American Type Culture Collections, 2013. 2 pages.

ATCC Product Data Sheet, "A3.6B10 (ATCC® HB-12318™)," American Type Culture Collections, 2013. 2 pages.

Harris, RJ et al, "Identification of multiple sources of charge heterogeneity in a recombinant antibody," J Chromatogr B Biomed Sci Appl., vol. 752(2): 233-245 (2001).

U.S. Appl. No. 14/093,867, filed Dec. 2, 201, Optimization of Antibodies That Bind Lymphocyte Activation Gene-3 (LAG-3), and Uses Thereof, Nils Lonberg.

U.S. Appl. No. 14/795,740, filed Jul. 9, 2015, Optimization of Antibodies That Bind Lymphocyte Activation Gene-3 (LAG-3), and Uses Thereof, Nils Lonberg.

U.S. Appl. No. 15/021,102, filed Mar. 10, 2016, Combination of Anti-LAG-3 Antibodies and Anti-PD-1 Antibodies to Treat Tumors, Alan J. Korman.

U.S. Appl. No. 13/058,492, filed Feb. 10, 2011, Human Antibodies That Bind Lymphocyte Activation Gene-3 (LAG-3) and Uses Thereof, Kent B. Thudium.

U.S. Appl. No. 14/093,867, dated Oct. 12, 2016, Ronald B. Schwadron.
U.S. Appl. No. 14/093,867, dated Jul. 1, 2016, Ronald B. Schwadron.
U.S. Appl. No. 14/093,867, dated May 10, 2016, Ronald B. Schwadron.
U.S. Appl. No. 14/093,867, dated Apr. 15, 2016, Ronald B. Schwadron.
U.S. Appl. No. 14/795,740, dated Oct. 15, 2015, Ronald B. Schwadron.
U.S. Appl. No. 13/058,492, dated Jul. 8, 2015, Ronald B. Schwadron.
U.S. Appl. No. 13/058,492, dated Mar. 17, 2015, Ronald B. Schwadron.
U.S. Appl. No. 13/058,492, dated Oct. 14, 2014, Ronald B. Schwadron.
U.S. Appl. No. 13/058,492, dated May 30, 2014, Ronald B. Schwadron.
U.S. Appl. No. 13/058,492, dated Aug. 14, 2012, Ronald B. Schwadron.

Extended European Search Report for EP Application No. 17177885, Hague, Netherlands, dated Nov. 17, 2017.

International Preliminary Report on Patentability and Written Opinion for Application Serial No. PCT/US2013/48999, dated Jan. 6, 2015, 7 pages.

Nivolumab, "Guide to Pharmacology," accessed at http://www.guidetopharmacology.org/GRAC/liganddisplayforward?liglandId=7335, last accessed Sep. 28, 2018, 1 page.

\* cited by examiner

LAG3.1 - Anti-LAG3 25F7 VH

```
V segment:      4-34
D segment:      5-12
J segment:      JH5b
```

```
          Q   V   Q   L   Q   Q   W   G   A   G   L   L   K   P   S   E   T   L
1         CAG GTG CAG CTA CAG CAG TGG GGC GCA GGA CTG TTG AAG CCT TCG GAG ACC CTG

CDR1
                                                   ------------------------------
          S   L   T   C   A   V   Y   G   G   S   F   S   D   Y   Y   W   N   W
55        TCC CTC ACC TGC GCT GTC TAT GGT GGG TCC TTC AGT GAT TAC TAC TGG AAC TGG

CDR2
                                                              ------------------
          I   R   Q   P   P   G   K   G   L   E   W   I   G   E   I   N   H   N
109       ATC CGC CAG CCC CCA GGG AAG GGG CTG GAG TGG ATT GGG GAA ATC AAT CAT AAT

CDR2
          ------------------------------------------------------------------------
          G   N   T   N   S   N   P   S   L   K   S   R   V   T   L   S   L   D
163       GGA AAC ACC AAC TCC AAC CCG TCC CTC AAG AGT CGA GTC ACC CTA TCA CTA GAC

T   S   K   N   Q   F   S   L   K   L   R   S   V   T   A   A   D   T
217       ACG TCC AAG AAC CAG TTC TCC CTG AAG CTG AGG TCT GTG ACC GCC GCG GAC ACG

CDR3
                                          ------------------------------------------
          A   V   Y   Y   C   A   F   G   Y   S   D   Y   E   Y   N   W   F   D
271       GCT GTG TAT TAC TGT GCG TTT GGA TAT AGT GAC TAC GAG TAC AAC TGG TTC GAC

CDR3
          ---
          P   W   G   Q   G   T   L   V   T   V   S   S
325       CCC TGG GGC CAG GGA ACC CTG GTC ACC GTC TCC TCA
```

Fig. 1A

LAG3.1 - Anti-LAG3 25F7 VK

V segment:     L6
J segment:     JK2

```
          E   I   V   L   T   Q   S   P   A   T   L   S   L   S   P   G   E   R
  1       GAA ATT GTG TTG ACA CAG TCT CCA GCC ACC CTG TCT TTG TCT CCA GGG GAA AGA

CDR1
                                   ----------------------------------------------
          A   T   L   S   C   R   A   S   Q   S   I   S   S   Y   L   A   W   Y
 55       GCC ACC CTC TCC TGC AGG GCC AGT CAG AGT ATT AGC AGC TAC TTA GCC TGG TAC

CDR2
                                                             -----------------
          Q   Q   K   P   G   Q   A   P   R   L   L   I   Y   D   A   S   N   R
109       CAA CAG AAA CCT GGC CAG GCT CCC AGG CTC CTC ATC TAT GAT GCA TCC AAC AGG

CDR2
          --------
          A   T   G   I   P   A   R   F   S   G   S   G   S   G   T   D   F   T
163       GCC ACT GGC ATC CCA GCC AGG TTC AGT GGC AGT GGG TCT GGG ACA GAC TTC ACT

CDR3
                                                                         --------
          L   T   I   S   S   L   E   P   E   D   F   A   V   Y   Y   C   Q   Q
217       CTC ACC ATC AGC AGC CTA GAG CCT GAA GAT TTT GCA GTT TAT TAC TGT CAG CAG

CDR3
          ----------------------------
          R   S   N   W   P   L   T   F   G   Q   G   T   N   L   E   I   K
271       CGT AGC AAC TGG CCT CTC ACT TTT GGC CAG GGG ACC AAC CTG GAG ATC AAA
```

*Fig. 1B*

LAG3.5 - Anti-LAG VH

Q V Q L Q Q W G A G L L K P S E T L
                                    CDR1
S L T C A V Y G G S F S D Y Y W N W
                                    CDR2
I R Q P P G K G L E W I G E I N H R
    CDR2
G S T N S N P S L K S R V T L S L D

T S K N Q F S L K L R S V T A A D T
                              CDR3
A V Y Y C A F G Y S D Y E Y N W F D
CDR3
P W G Q G T L V T V S S

*Fig. 2A*

LAG3.5 - Anti- LAG3 VK

V segment:    L6
J segment:    JK2

```
         E   I   V   L   T   Q   S   P   A   T   L   S   L   S   P   G   E   R
1        GAA ATT GTG TTG ACA CAG TCT CCA GCC ACC CTG TCT TTG TCT CCA GGG GAA AGA

CDR1
                                     ------------------------------------------
         A   T   L   S   C   R   A   S   Q   S   I   S   S   Y   L   A   W   Y
55       GCC ACC CTC TCC TGC AGG GCC AGT CAG AGT ATT AGC AGC TAC TTA GCC TGG TAC

CDR2
                                                          ------------------------
         Q   Q   K   P   G   Q   A   P   R   L   L   I   Y   D   A   S   N   R
109      CAA CAG AAA CCT GGC CAG GCT CCC AGG CTC CTC ATC TAT GAT GCA TCC AAC AGG

CDR2
         ---------
         A   T   G   I   P   A   R   F   S   G   S   G   S   G   T   D   F   T
163      GCC ACT GGC ATC CCA GCC AGG TTC AGT GGC AGT GGG TCT GGG ACA GAC TTC ACT

CDR3
                                                                      ---------
         L   T   I   S   S   L   E   P   E   D   F   A   V   Y   Y   C   Q   Q
217      CTC ACC ATC AGC AGC CTA GAG CCT GAA GAT TTT GCA GTT TAT TAC TGT CAG CAG

CDR3
         ------------------------------------
         R   S   N   W   P   L   T   F   G   Q   G   T   N   L   E   I   K
271      CGT AGC AAC TGG CCT CTC ACT TTT GGC CAG GGG ACC AAC CTG GAG ATC AAA
```

*Fig. 2B*

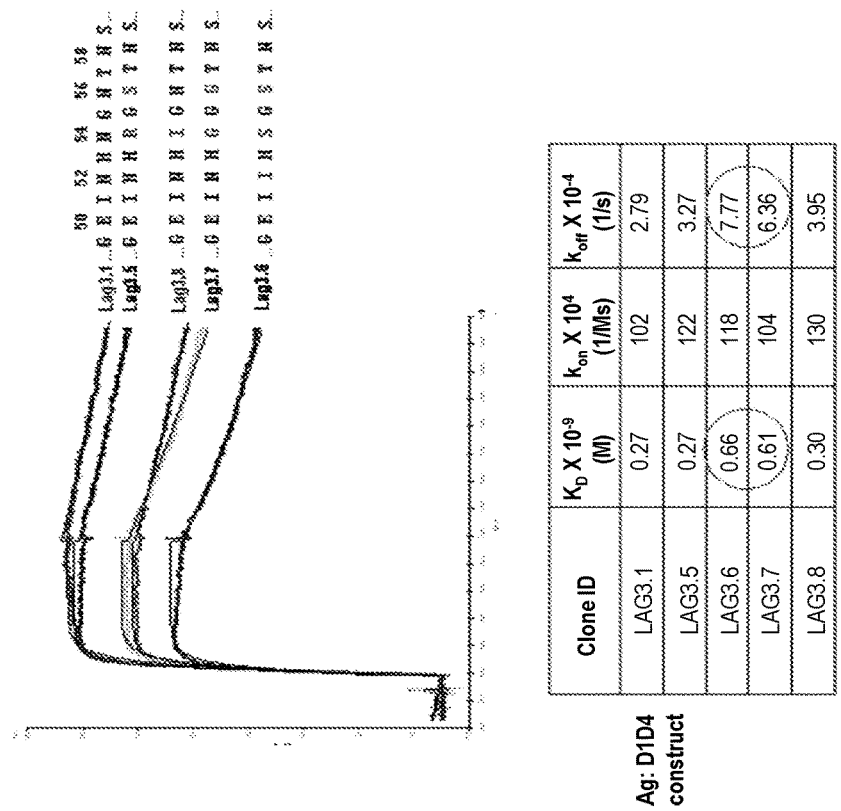
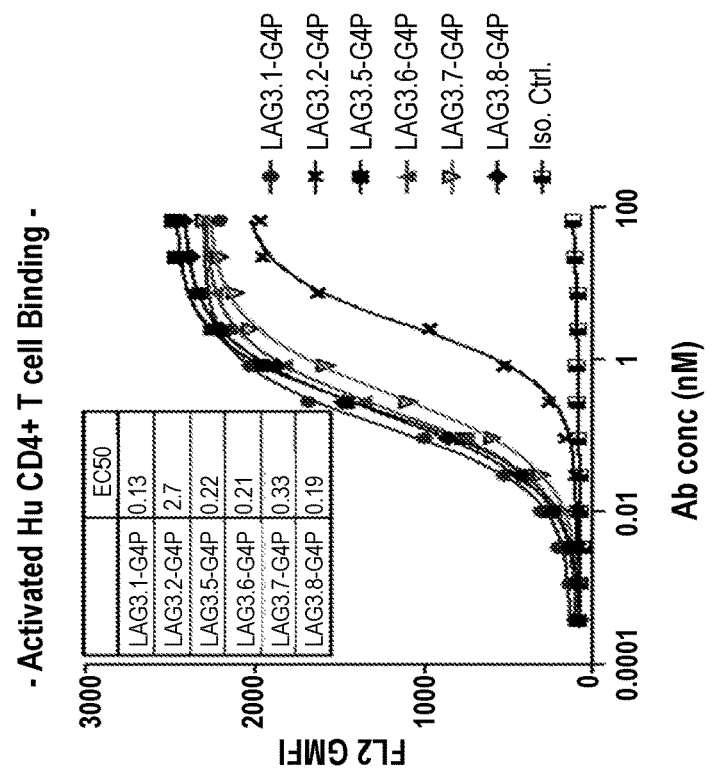
Fig. 4B
Fig. 4A

Mab 5 day incubation     CDR2 peptide alone is shown

| | INHD*GNTNSNPSLK | INHDGNTNSNPSLK | | IDHNGNTNSNPSLK | CDR2 deamidation Total |
|---|---|---|---|---|---|
| | INHNGNTDSNPSLK | | | | |
| 3.1 | 2.5% | 5.1% | | 1.5% | 9% |
| 3.1 pH8 | 10.0% | 15.3% | | 4.9% | 30% |

| | INHRGSTD?SNPSLK | INHRGSTNSNPSLK | ID?HRGSTDSNPSLK | |
|---|---|---|---|---|
| 3.5 | 2.3% | - | 1.5% | 4% |
| 3.5 pH8 | 3.1% | - | 1.7% | 5% |

*Fig. 8*

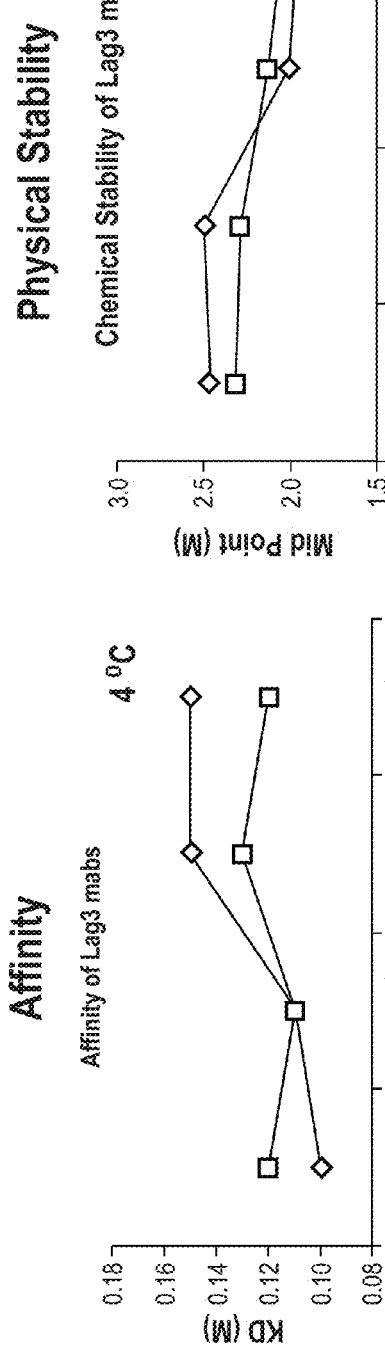
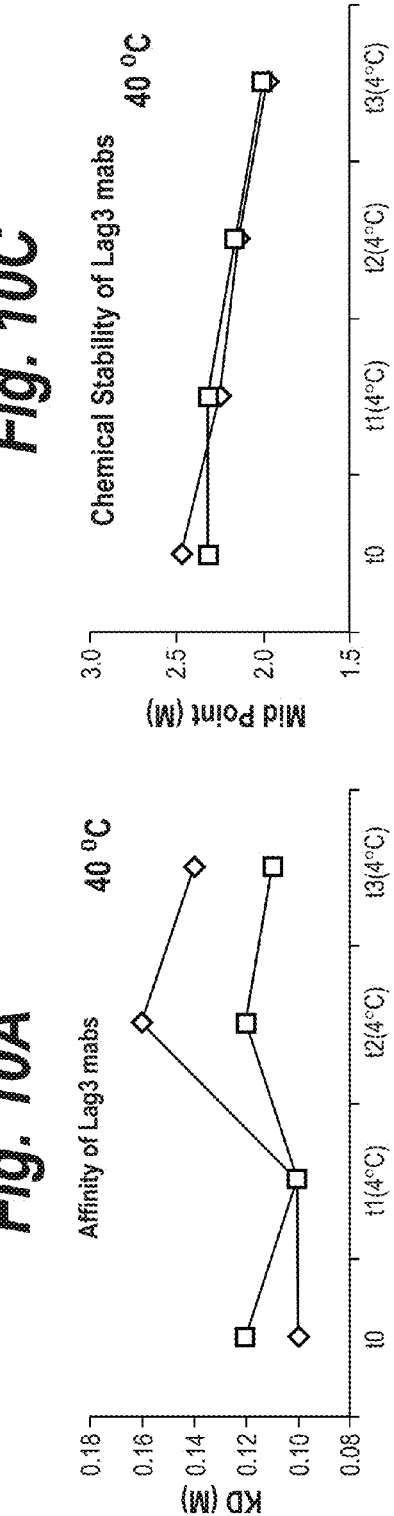
Fig. 10A, Fig. 10B, Fig. 10C, Fig. 10D

# OPTIMIZATION OF ANTIBODIES THAT BIND LYMPHOCYTE ACTIVATION GENE-3 (LAG-3), AND USES THEREOF

RELATED APPLICATIONS

This application claims priority to U.S. application Ser. No. 14/093,867 (Allowed), filed Dec. 2, 2013, which claims priority to Application No. PCT/US2013/048999, filed Jul. 2, 2013, which claims priority to U.S. Provisional Application No. 61/667,058, filed Jul. 2, 2012. The contents of the foregoing applications are incorporated herein by reference.

SEQUENCE LISTING

The instant application contains a Sequence Listing which has been submitted in ASCII format via EFS-Web and is hereby incorporated by reference in its entirety. Said ASCII copy, created on Oct. 18, 2016, is named MXI-513DV_Sequence Listing.txt and is 42,054 bytes in size.

BACKGROUND OF THE INVENTION

Therapeutic antibodies are one of the fastest growing segments of the pharmaceutical industry. To maintain potency (i.e., activity) and minimize immunogenicity, antibodies and other protein drugs must be protected from physical and chemical degradation during manufacturing and storage. Indeed, one of the primary difficulties in developing antibody therapeutics is the potential immunogenic response when administered to a subject, which can lead to rapid clearance or even induce life-threatening side effects including anaphylactic shock. Various factors influence the immunogenicity of an antibody such as its physiochemical properties (e.g., purity, stability, or solubility), clinical factors (e.g., dose, route of administration, heterogeneity of the disease, or patient features), and concomitant treatment with other agents (Swann et al. (2008) *Curr Opinion Immuol* 20:493-499).

Immunogenicity of antibodies and/or loss of antibody activity is often due to deamidation. Deamidation is a chemical degradative process that spontaneously occurs in proteins (e.g., antibodies). Deamidation removes an amide functional group from an amino acid residue, such as asparagine and glutamine, thus damaging its amide-containing side chains. This, in turn, causes structural and biological alterations throughout the protein, thus creating heterogeneous forms of the antibody. Deamidation is one of the most common post-translational modifications that occurs in recombinantly produced therapeutic antibodies.

For example, heterogeneity in the heavy chain of monoclonal antibody h1B4 (a humanized anti-CD18 antibody) due to deamidation during cell culture was reported by Tsai et al. (*Pharm Res* 10(11):1580 (1993)). In addition, reduction/loss of biological activity due to deamidation has been a recognized problem. For example, Kroon et al. characterized several deamidation sites in therapeutic antibody OKT3, and reported that samples of OKT3 production lots (aged 14 months to 3 years) had fallen below 75% activity (*Pharm Res* 9(11):1386 (1992), page 1389, second column). In addition, samples of OKT3 showing large amounts of the oxidized peptides in their maps had significantly reduced activity in the antigen binding potency assay (page 1390, first column). The authors concluded that specific sites of chemical modification that occur upon storage of OKT3 were identified by peptide mapping and correlated with observed changes in chemical analyses and biological assays of the antibody (page 1392, first column). Loss of biological activity also has been reported for a variety of other deamidated therapeutic proteins, including recombinant human DNase (Cacia et al. (1993) *J. Chromatogr.* 634:229-239) and recombinant soluble CD4 (Teshima et al. (1991) *Biochemistry* 30:3916-3922).

Overall, deamidation poses a significant and unpredictable problem to the pharmaceutical industry. Efforts associated with monitoring the variability caused by deamidation within antibody therapeutics, in particular, as well as FDA concerns associated with this variability, increase costs and delay clinical trials. Moreover, modifications to address this issue, including shifting conditions (e.g., temperature, pH, and cell type) associated with recombinant production and/or alteration of amino acids which are susceptible to deamidation (e.g., site-directed mutagenesis) can negatively impact stability and activity, especially when changes are made within the complementarity determining regions (CDRs) of the antibody. Accordingly, the need exists for more stable versions of therapeutic antibodies.

SUMMARY

The present invention provides isolated monoclonal antibodies (e.g., human monoclonal antibodies) that bind LAG-3 (e.g., human LAG-3) and have optimized physical stability compared to previously described anti-LAG-3 antibodies. In particular, the invention relates to a modified form of antibody 25F7 (US 2011/0150892 A1) which exhibits significantly improved thermal and chemical stability compared to the unmodified antibody. Specifically, by altering the critical binding region of the heavy chain CDR2 domain of antibody 25F7, it was shown that the modified antibody exhibited significantly higher physical and thermal stability, reduced deamidation, higher thermal reversibility, and lower aggregation. At the same time, it was unexpectedly observed that the modified antibody retained the same high binding affinity to human LAG-3 and functional activity of the unmodified antibody, including the ability to inhibit binding of LAG-3 to major histocompatibility (MHC) Class II molecules and stimulate antigen-specific T cell responses. The combined substantial increase in stability and retention of binding/biological activity of the modified antibody was surprising, particularly in view of the criticality of CDRs regions to antibody function.

The antibodies of the invention can be used for a variety of applications, including detection of LAG-3 protein and stimulation of antigen-specific T cell responses in tumor-bearing or virus-bearing subjects.

Accordingly, in one aspect, the invention pertains to an isolated monoclonal antibody (e.g., a human antibody), or an antigen-binding portion thereof, having a heavy chain variable region comprising the amino acid sequence of SEQ ID NO: 12. In another embodiment, the antibody further includes a light chain variable region comprising the amino acid sequence of SEQ ID NO: 14. In another embodiment, the antibody, or antigen-binding portion thereof, includes the CDR1, CDR2, and CDR3 regions of a heavy chain variable region comprising the amino acid sequence of SEQ ID NO: 12 (e.g., SEQ ID NOs: 15, 16, and 17, respectively). In another embodiment, the antibody further includes the CDR1, CDR2, and CDR3 regions of a light chain variable region comprising the amino acid sequence of SEQ ID NO: 12 (e.g., SEQ ID NOs: 18, 19, and 20, respectively).

In a preferred embodiment the antibody exhibits increased physical properties (i.e., thermal and chemical stability) compared to antibody 25F7, while still retaining at least the same binding affinity for human LAG-3 as 25F7. For example, the antibody exhibits decreased sequence variability in the heavy chain CDR2 region due to deamidation, compared to antibody 25F7, e.g., approximately 2.5% or less modification of the amino acid sequence after 12 weeks at 4 C.° (i.e., under "real-time" stability studies as described herein) and/or approximately 12.0% or less modification of the amino acid sequence after 12 weeks at 40 C.° (i.e., under accelerated stress conditions, as described herein), while still retaining a binding affinity for human LAG-3 of about at least $K_D$ of $1 \times 10^{-7}$ M or less (more preferably, a $K_D$ of $1 \times 10^{-8}$M or less, a $K_D$ of $5 \times 10^{-9}$ M or less, or a $K_D$ of $1 \times 10^{-9}$M or less). In another embodiment, the antibody exhibits thermal reversibility of at least about 40% in PBS at pH8.0.

In another embodiment, the antibody possesses a higher melting temperature (indicating greater overall stability in vivo), compared to the unmodified antibody (Krishnamurthy R and Manning M C (2002) *Curr Pharm Biotechnol* 3:361-71). In one embodiment, the antibody exhibits a $T_{M1}$ (the temperature of initial unfolding) of greater than 60° C., e.g., greater than 65° C., or greater than 70° C. The melting point of an antibody can be measured using differential scanning calorimetry (Chen et al (2003) *Pharm Res* 20:1952-60; Ghirlando et al (1999) *Immunol Lett* 68:47-52) or circular dichroism (Murray et al. (2002) *J. Chromatogr Sci* 40:343-9).

In another embodiment, the antibody is characterized by its resistance to rapid degradation. Degradation of an antibody can be measured using capillary electrophoresis (CE) and MALDI-MS (Alexander A J and Hughes D E (1995) *Anal Chem* 67:3626-32).

In another embodiment, the antibody exhibits minimal aggregation effects, e.g., aggregation of 25% or less, such as 20% or less, 15% or less, 10% or less, 5% or less, or 4% or less. Aggregation can lead to the triggering of an unwanted immune response and/or altered or unfavorable pharmacokinetic properties, Aggregation can be measured by several techniques, including size-exclusion column (SEC), high performance liquid chromatography (HPLC), and light scattering.

In another embodiment, the antibody further exhibits at least one of the following properties:
(a) binding to monkey LAG-3;
(b) lack of binding to mouse LAG-3;
(c) inhibition of binding of LAG-3 to major histocompatibility (MHC) class II molecules; and
(d) stimulation of immune responses, particularly antigen-specific T cell responses.

Preferably, the antibody exhibits at least two of properties (a), (b), (c) and (d). More preferably, the antibody exhibits at least three of properties (a), (b), (c) and (d). Even more preferably, the antibody exhibits all four of properties (a), (b), (c) and (d).

In another embodiment, the antibody stimulates an antigen-specific T cell response, such as interleukin-2 (IL-2) production in an antigen-specific T cell response. In other embodiments, the antibody stimulates an immune response, such as an anti-tumor response (e.g., inhibition of tumor growth in an in vivo tumor graft model) or an autoimmune response (e.g., development of diabetes in NOD mice).

In another embodiment, the antibody binds an epitope of human LAG-3 comprising the amino acid sequence PGH-PLAPG (SEQ ID NO: 21). In another embodiment, the antibody binds an epitope of human LAG-3 comprising the amino acid sequence HPAAPSSW (SEQ ID NO: 22) or PAAPSSWG (SEQ ID NO: 23).

In other embodiments, the antibody stains pituitary tissue by immunohistochemistry, or does not stain pituitary tissue by immunohistochemistry.

Antibodies of the invention can be full-length antibodies, for example, of an IgG1, IgG2 or IgG4 isotype, optionally with a serine to proline mutation in the heavy chain constant region hinge region (at a position corresponding to position 241 as described in Angal et al. (1993) *Mol. Immunol.* 30:105-108), such that inter-heavy chain disulfide bridge heterogeneity is reduced or abolished. In one aspect, the constant region isotype is IgG4 with a mutation at amino acid residues 228, e.g., S228P. Alternatively, the antibodies can be antibody fragments, such as Fab, Fab' or Fab'2 fragments, or single chain antibodies.

In another aspect of the invention, the antibody (or antigen-binding portion thereof) is part of an immunoconjugate which includes a therapeutic agent, e.g., a cytotoxin or a radioactive isotope, linked to the antibody. In another aspect, the antibody is part of a bispecific molecule which includes a second functional moiety (e.g., a second antibody) having a different binding specificity than said antibody, or antigen binding portion thereof.

Compositions comprising antibodies, or antigen-binding portions thereof, immunoconjugates or bispecific molecules of the invention, optionally formulated in a pharmaceutically acceptable carrier, also are provided.

Nucleic acid molecules encoding the antibodies, or antigen-binding portions (e.g., variable regions and/or CDRs) thereof, of the invention also are provided, as well as expression vectors comprising such nucleic acids and host cells comprising such expression vectors. Methods for preparing anti-LAG-3 antibodies using the host cells comprising such expression vectors also are provided, and can include the steps of (i) expressing the antibody in the host cell and (ii) isolating the antibody from the host cell.

In another aspect, the invention provides methods of stimulating immune responses using anti-LAG-3 antibodies of the invention. In one embodiment, the method involves stimulating an antigen-specific T cell response by contacting T cells with an antibody of the invention, such that an antigen-specific T cell response is stimulated. In a preferred embodiment, interleukin-2 production by the antigen-specific T cell is stimulated. In another embodiment, the subject is a tumor-bearing subject and an immune response against the tumor is stimulated. In another embodiment, the subject is a virus-bearing subject and an immune response against the virus is stimulated.

In yet another embodiment, the invention provides a method for inhibiting growth of tumor cells in a subject comprising administering to the subject an antibody, or antigen-binding portion thereof, of the invention, such that growth of the tumor is inhibited in the subject. In still another embodiment, the invention provides a method for treating viral infection in a subject comprising administering to the subject an antibody, or antigen-binding portion thereof, of the invention such that the viral infection is treated in the subject. In another embodiment, these methods comprise administering a composition, bispecific, or immunoconjugate of the invention.

In yet another embodiment, the invention provides a method for stimulating an immune response in a subject comprising administering to the subject an antibody, or antigen-binding portion thereof, of the invention and at least one additional immunostimulatory antibody, such as an anti-PD-1 antibody, an anti-PD-L1 antibody and/or an anti-CTLA-4 antibody, such that an immune response is stimulated in the subject, for example to inhibit tumor growth or to stimulate an anti-viral response. In one embodiment, the additional immunostimulatory antibody is an anti-PD-1 antibody. In another embodiment, the additional immunostimulatory agent is an anti-PD-L1 antibody. In yet another embodiment, the additional immunostimulatory agent is an anti-CTLA-4 antibody. In yet another embodiment, an antibody, or antigen-binding portion thereof, of the invention is administered with a cytokine (e.g., IL-2 and/or IL-21), or a costimulatory antibody (e.g., an anti-CD137 and/or anti-GITR antibody). The antibodies can be, for example, human, chimeric or humanized antibodies.

In another aspect, the invention provides anti-LAG-3 antibodies and compositions of the invention for use in the foregoing methods, or for the manufacture of a medicament for use in the foregoing methods (e.g., for treatment).

Other features and advantages of the instant disclosure will be apparent from the following detailed description and examples, which should not be construed as limiting. The contents of all references, Genbank entries, patents and published patent applications cited throughout this application are expressly incorporated herein by reference.

BRIEF DESCRIPTION OF THE DRAWINGS

FIG. 1A shows the nucleotide sequence (SEQ ID NO: 1) and amino acid sequence (SEQ ID NO: 2) of the heavy chain variable region of the 25F7 human monoclonal antibody. The CDR1 (SEQ ID NO: 5), CDR2 (SEQ ID NO: 6) and CDR3 (SEQ ID NO: 7) regions are delineated and the V, D and J germline derivations are indicated. The CDR regions are delineated using the Kabat system (Kabat et al. (1991) Sequences of Proteins of Immunological Interest, Fifth Edition, U.S. Department of Health and Human Services, NIH Publication No. 91-3242).

FIG. 1B shows the nucleotide sequence (SEQ ID NO: 3) and amino acid sequence (SEQ ID NO: 4) of the kappa light chain variable region of the 25F7 human monoclonal antibody. The CDR1 (SEQ ID NO: 8), CDR2 (SEQ ID NO: 9) and CDR3 (SEQ ID NO: 10) regions are delineated and the V and J germline derivations are indicated. The full-length heavy and light chain amino acid sequences antibody 25F7 are shown in SEQ ID NOs: 32 and 34, respectively.

FIG. 2A shows the amino acid sequence (SEQ ID NO: 12) of the heavy chain variable region of the LAG3.5 monoclonal antibody. The CDR1 (SEQ ID NO: 15), CDR2 (SEQ ID NO: 16) and CDR3 (SEQ ID NO: 17) regions are delineated. The full-length heavy and light chain amino acid sequences antibody LAG3.5 are shown in SEQ ID NOs: 35 and 37, respectively.

FIG. 2B shows the nucleotide sequence (SEQ ID NO: 13) and amino acid sequence (SEQ ID NO: 14) of the kappa light chain variable region of the LAG3.5 monoclonal antibody. The CDR1 (SEQ ID NO: 18), CDR2 (SEQ ID NO: 19) and CDR3 (SEQ ID NO: 20) regions are delineated.

FIG. 3 also discloses SEQ ID NO: 40.

FIGS. 4A and 4B are graphs showing the binding activity ($EC_{50}$ and affinity, respectively) of antibodies LAG3.1 (25F7), LAG3.2, LAG3.5, LAG3.6, LAG3.7, and LAG3.8 to activated human CD4+ T cells. FIG. 4B discloses SEQ ID NOS 41, 42, 45, 44, and 43, respectively, in order of appearance.

FIG. 8 shows the results of peptide mapping using mass-spectrometry (chemical modifications/molecular stability) for antibodies LAG3.1 (25F7) and LAG3.5 reflecting deamidation and isomerization after incubating for 5 days under accelerated stress conditions as described herein. FIG. 8 discloses SEQ ID NOS 46-52, respectively, in order of appearance.

FIGS. 10 A, B, C, and D are graphs comparing the affinity and physical stability (i.e., thermal and chemical stability) of antibodies LAG3.1 and LAG3.5 at 4 C.° and 40 C.°, i.e., both accelerated stress conditions and "real-time" stability studies, as described herein.

DETAILED DESCRIPTION OF THE INVENTION

Figure 3:
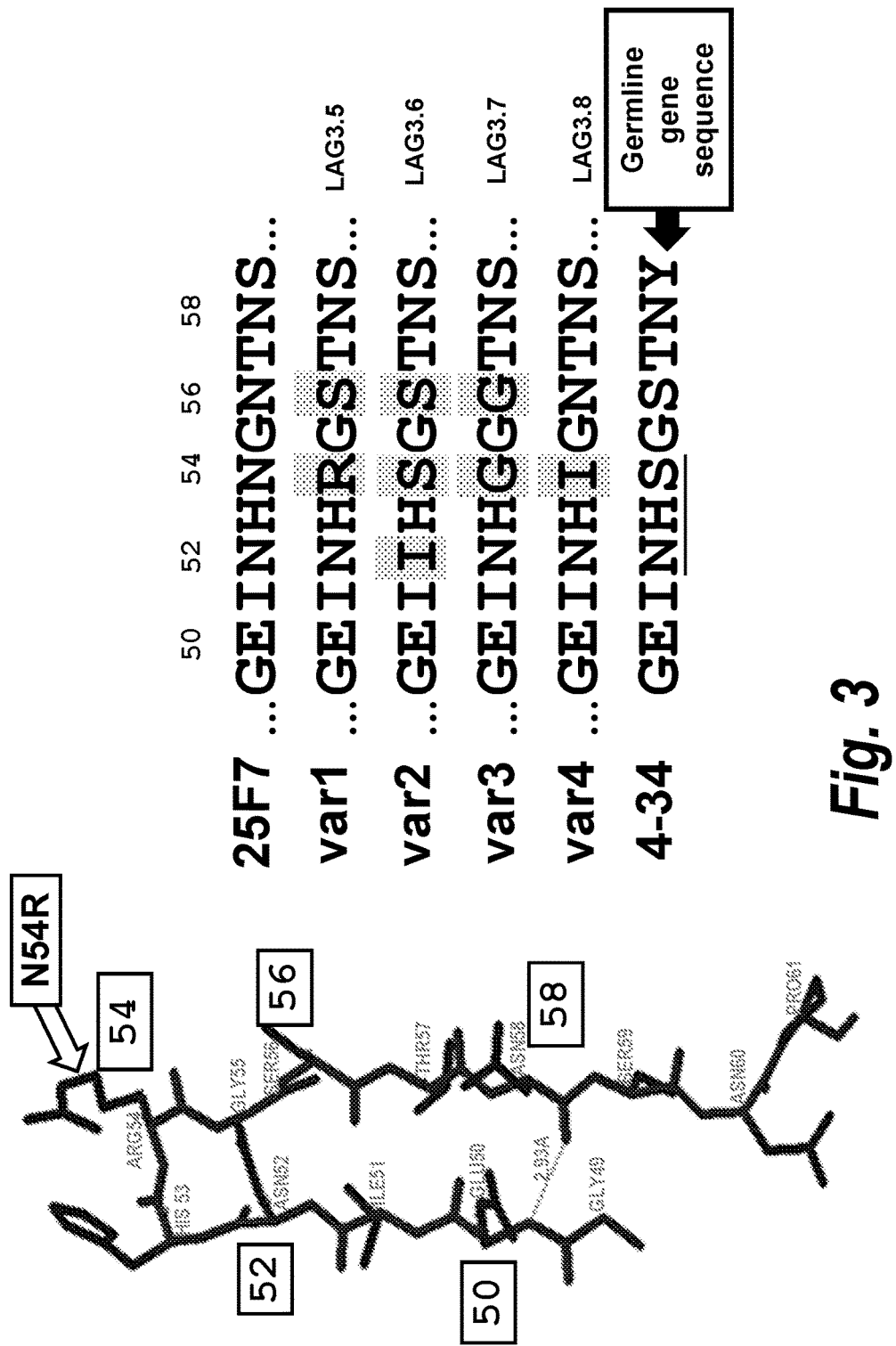
FIG. 3 shows the amino acid sequences of the CDR2 heavy chain variable region sequences of the LAG-3 variants LAG3.5 (SEQ ID NO: 42), LAG3.6 (SEQ ID NO: 43), LAG3.7 (SEQ ID NO: 44), and LAG3.8 (SEQ ID NO: 45), compared to the amino acid sequence of the CDR2 heavy chain variable region sequence of antibody 25F7 (LAG3.1) (SEQ ID NO: 41) and corresponding human germline sequence (SEQ ID NO: 27). The CDR2 heavy chain variable region of LAG3.5 differs from the CDR2 heavy chain variable region of 25F7 by arginine (R) at position 54 (versus asparagine (N)) and serine (S) at position 56 (versus asparagines (N)). The remaining CDRs of LAG3.5 anf 25F7 are identical.
Figure 5A:
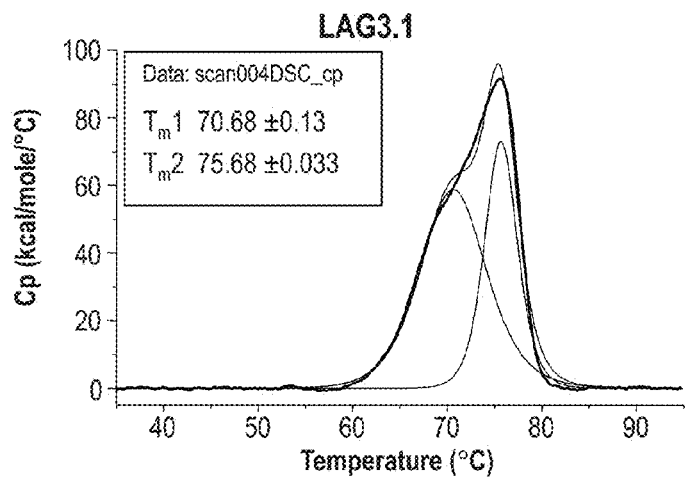
FIGS. 5A, B, C, D, and E are graphs showing thermal melting curves (i.e., thermal stability) of antibodies LAG3.1 (25F7), LAG3.5, LAG3.6, LAG3.7, and LAG3.8, respectively.
Figure 5B:
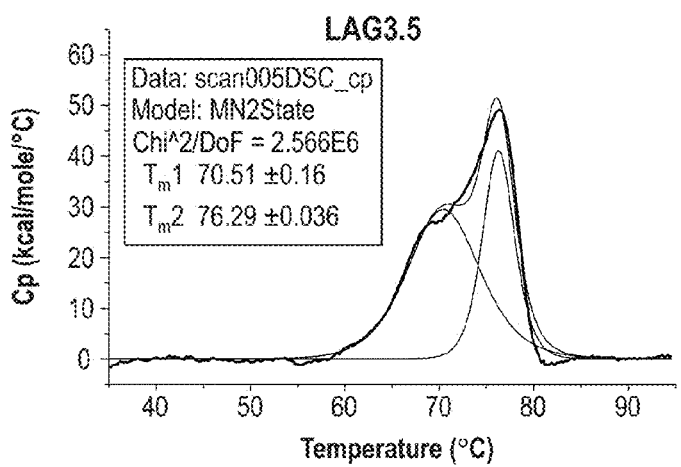
Figure 5C:
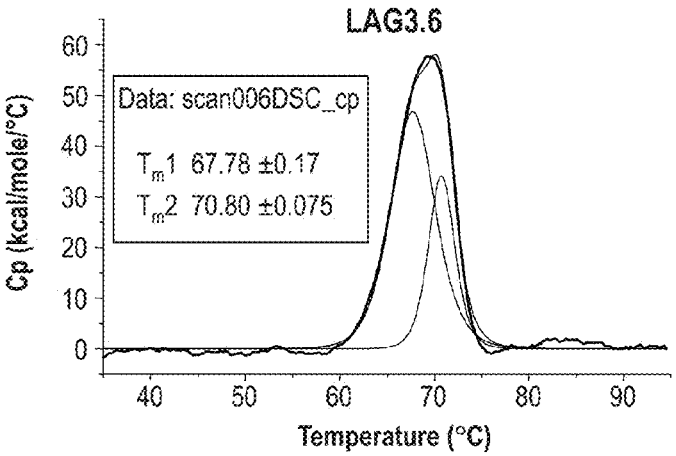
Figure 5D:
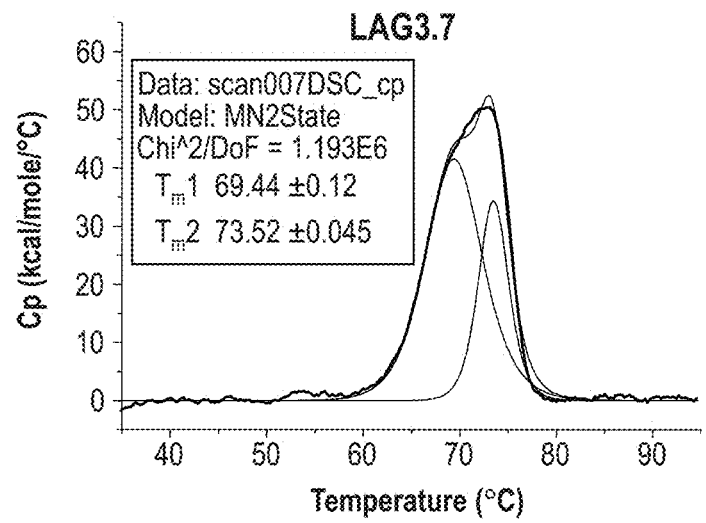
Figure 5E:
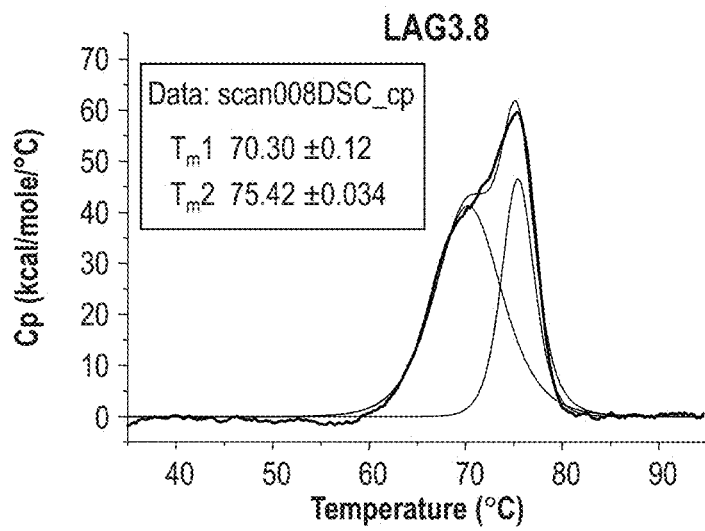
Figure 6A:
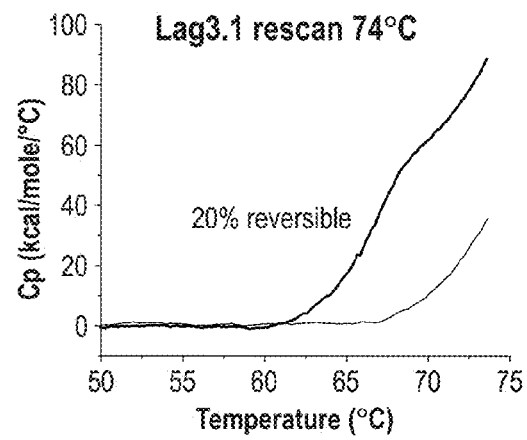
FIGS. 6A, B, C, D, and E are graphs showing thermal reversibility curves (i.e., thermal stability) of antibodies LAG3.1 (25F7), LAG3.5, LAG3.6, LAG3.7, and LAG3.8, respectively.
Figure 6B:
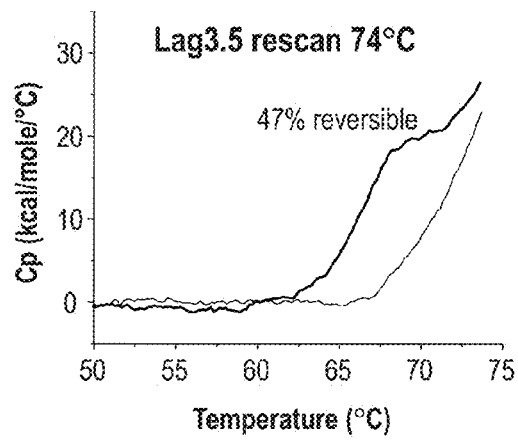
Figure 6C:
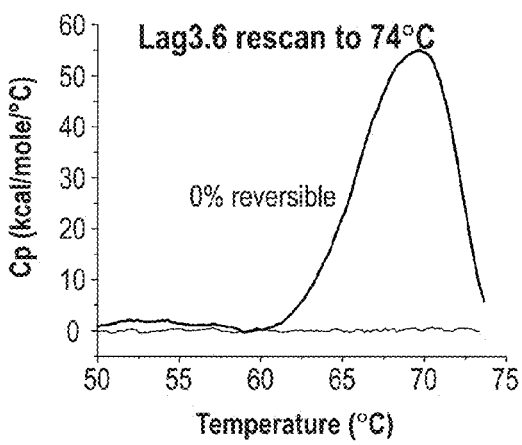
Figure 6D:
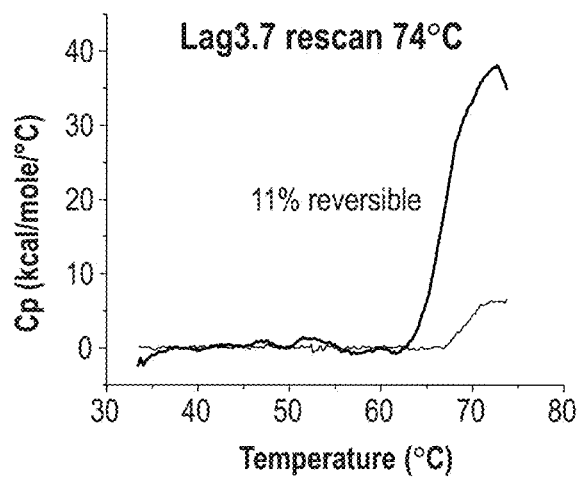
Figure 6E:
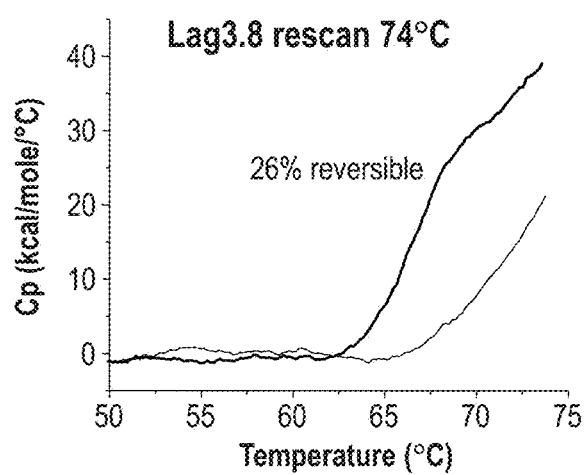

In order that the present disclosure may be more readily understood, certain terms are first defined. Additional definitions are set forth throughout the detailed description.

The terms "25F7," "antibody 25F7," "antibody LAG3.1," and "LAG3.1" refer to the anti-human LAG-3 antibody described in US2011/0150892 A1. The nucleotide sequence (SEQ ID NO: 1) encoding the heavy chain variable region of 25F7 (LAG3.1) and the corresponding amino acid sequence (SEQ ID NO: 2) is shown in FIG. 1A (with CDR sequences designated as SEQ ID NOs: 4, 5, and 7, respectively). The nucleotide sequence (SEQ ID NO: 3) encoding the light chain variable region of 25F7 (LAG3.1) and the corresponding amino acid sequence (SEQ ID NO: 4) is shown in FIG. 1B (with CDR sequences designated as SEQ ID NOs: 8, 9, and 10, respectively).

The term "LAG-3" refers to Lymphocyte Activation Gene-3. The term "LAG-3" includes variants, isoforms, homologs, orthologs and paralogs. For example, antibodies specific for a human LAG-3 protein may, in certain cases, cross-react with a LAG-3 protein from a species other than human. In other embodiments, the antibodies specific for a human LAG-3 protein may be completely specific for the human LAG-3 protein and may not exhibit species or other types of cross-reactivity, or may cross-react with LAG-3 from certain other species but not all other species (e.g., cross-react with monkey LAG-3 but not mouse LAG-3). The term "human LAG-3" refers to human sequence LAG-3, such as the complete amino acid sequence of human LAG-3 having Genbank Accession No. NP_002277 (SEQ ID NO:

29). The term "mouse LAG-3" refers to mouse sequence LAG-3, such as the complete amino acid sequence of mouse LAG-3 having Genbank Accession No. NP_032505. LAG-3 is also known in the art as, for example, CD223. The human LAG-3 sequence may differ from human LAG-3 of Genbank Accession No. NP_002277 by having, e.g., conserved mutations or mutations in non-conserved regions and the LAG-3 has substantially the same biological function as the human LAG-3 of Genbank Accession No. NP_002277. For example, a biological function of human LAG-3 is having an epitope in the extracellular domain of LAG-3 that is specifically bound by an antibody of the instant disclosure or a biological function of human LAG-3 is binding to MHC Class II molecules.

The term "monkey LAG-3" is intended to encompass LAG-3 proteins expressed by Old World and New World monkeys, including but not limited to cynomolgus monkey LAG-3 and rhesus monkey LAG-3. A representative amino acid sequence for monkey LAG-3 is the rhesus monkey LAG-3 amino acid sequence which is also deposited as Genbank Accession No. XM_001108923. Another representative amino acid sequence for monkey LAG-3 is the alternative rhesus monkey sequence of clone pa23-5 as described in US 2011/0150892 A1. This alternative rhesus sequence exhibits a single amino acid difference, at position 419, as compared to the Genbank-deposited sequence.

A particular human LAG-3 sequence will generally be at least 90% identical in amino acid sequence to human LAG-3 of Genbank Accession No. NP_002277 and contains amino acid residues that identify the amino acid sequence as being human when compared to LAG-3 amino acid sequences of other species (e.g., murine). In certain cases, a human LAG-3 can be at least 95%, or even at least 96%, 97%, 98%, or 99% identical in amino acid sequence to LAG-3 of Genbank Accession No. NP_002277. In certain embodiments, a human LAG-3 sequence will display no more than 10 amino acid differences from the LAG-3 sequence of Genbank Accession No. NP_002277. In certain embodiments, the human LAG-3 can display no more than 5, or even no more than 4, 3, 2, or 1 amino acid difference from the LAG-3 sequence of Genbank Accession No. NP_002277. Percent identity can be determined as described herein.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

An "antigen-specific T cell response" refers to responses by a T cell that result from stimulation of the T cell with the antigen for which the T cell is specific. Non-limiting examples of responses by a T cell upon antigen-specific stimulation include proliferation and cytokine production (e.g., IL-2 production).

The term "antibody" as referred to herein includes whole antibodies and any antigen binding fragment (i.e., "antigen-binding portion") or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., a LAG-3 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_H$ and $C_H1$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a LAG-3 protein is substantially free of antibodies that specifically bind antigens other than LAG-3 proteins). An isolated antibody that specifically binds a human LAG-3 protein may, however, have cross-reactivity to other antigens, such as LAG-3 proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity, which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications can be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds human LAG-3" is intended to refer to an antibody that binds to human LAG-3 protein (and possibly a LAG-3 protein from one or more non-human species) but does not substantially bind to non-LAG-3 proteins. Preferably, the antibody binds to a human LAG-3 protein with "high affinity", namely with a $K_D$ of $1\times10^{-7}$M or less, more preferably $1\times10^{-8}$M or less, more preferably $5\times10^{-9}$M or less, more preferably $1\times10^{-9}$M or less.

The term "does not substantially bind" to a protein or cells, as used herein, means does not bind or does not bind with a high affinity to the protein or cells, i.e. binds to the protein or cells with a $K_D$ of $1\times10^{-6}$ M or more, more preferably $1\times10^{-5}$M or more, more preferably $1\times10^{-4}$M or more, more preferably $1\times10^{-3}$M or more, even more preferably $1\times10^{-2}$M or more.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$," as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

The term "high affinity" for an IgG antibody refers to an antibody having a $K_D$ of $1\times10^{-7}$M or less, more preferably $5\times10^{-8}$M or less, even more preferably $1\times10^{-8}$M or less, even more preferably $5\times10^{-9}$M or less and even more preferably $1\times10^{-9}$M or less for a target antigen. However, "high affinity" binding can vary for other antibody isotypes. For example, "high affinity" binding for an IgM isotype refers to an antibody having a $K_D$ of $10^{-6}$M or less, more preferably $10^{-7}$M or less, even more preferably $10^{-8}$ M or less.

The term "deamidation" refers to a chemical degredative process that spontaneously occurs in proteins (e.g., antibodies). Deamidation removes an amide functional group from an amino acid residue, such as asparagine and glutamine, thus damaging its amide-containing side chains. Specifically, the side chain of an asparagine attacks the adjacent peptide group, forming a symmetric succinimide intermediate. The symmetry of the intermediate results in two hydrolysis products, either aspartate or isoaspartate. A similar reaction can also occur in aspartate side chains, yielding a partial conversion to isoaspartate. In the case of glutamine, the rate of deamidation is generally ten fold less than asparagine, however, the mechanism is essentially the same, requiring only water molecules to proceed.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

Various aspects of the invention are described in further detail in the following subsections.

Anti-LAG-3 Antibodies Having Increased Stability and Advantageous Functional Properties Antibodies of the invention specifically bind to human LAG-3 and have optimized stability compared to previously described anti-LAG-3 antibodies, particularly compared to antibody 25F7 (LAG3.1). This optimization includes reduced deamidation (e.g., increased chemical stability) and increased thermal refolding (e.g., increased physical stability), while still retaining high affinity binding to human LAG-3.

Methods for identifying deamidation sites are known in the art (see, e.g., ion exchange, reversed phase, and hydrophobic interaction chromatography, and peptide mapping of proteolytic digests (LC-MS)). Suitable assays for measuring physical stability include, e.g., analysis of melting points and/or refolding of antibody structure following denaturation (e.g., percent reversibility as described, e.g., in Example 3, Section 3).

Binding to human LAG-3 can be assessed using one or more techniques also well established in the art. For example, an antibody can be tested by a flow cytometry assay in which the antibody is reacted with a cell line that expresses human LAG-3, such as CHO cells that have been transfected to express LAG-3 (e.g., human LAG-3, or monkey LAG-3 (e.g., rhesus or cynomolgus monkey) or mouse LAG-3) on their cell surface. Other suitable cells for use in flow cytometry assays include anti-CD3-stimulated CD4+ activated T cells, which express native LAG-3. Additionally or alternatively, binding of the antibody, including the binding kinetics (e.g., $K_D$ value), can be tested in BIAcore assays. Still other suitable binding assays include ELISA assays, for example, using a recombinant LAG-3 protein.

Antibodies of the invention preferably bind to human LAG-3 protein with a $K_D$ of $1 \times 10^{-7}$M or less, and more preferably $1 \times 10^{-8}$ M or less, $5 \times 10^{-9}$M or less, or $1 \times 10^{-9}$M or less.

Typically, the antibody binds to LAG-3 in lymphoid tissues, such as tonsil, spleen or thymus, which can be detected by immunohistochemistry. In one embodiment, the antibody stains pituitary tissue (e.g., are retained in the pituitary) as measured by immunohistochemistry. In another embodiment, the antibody does not stain pituitary tissue (i.e., is not retained in the pituitary) as measured by immunohistochemistry.

Additional functional properties include cross-reactivity with LAG-3 from other species. For example, the antibody can bind to monkey LAG-3 (e.g., cynomolgus monkey, rhesus monkey), but not substantially bind to LAG-3 from mouse LAG-3. Preferably, an antibody of the invention binds to human LAG-3 with high affinity.

Other functional properties include the ability of the antibody to stimulate an immune response, such as an antigen-specific T cell response. This can be tested, for example, by assessing the ability of the antibody to stimulate interleukin-2 (IL-2) production in an antigen-specific T cell response. In certain embodiments, the antibody binds to human LAG-3 and stimulates an antigen-specific T cell response. In other embodiments, the antibody binds to human LAG-3 but does not stimulate an antigen-specific T cell response. Other means for evaluating the capacity of the antibody to stimulate an immune response include testing its ability to inhibit tumor growth, such as in an in vivo tumor graft model (see, e.g., Example 6) or the ability to stimulate an autoimmune response, such as the ability to promote the development of an autoimmune disease in an autoimmune model, e.g., the ability to promote the development of diabetes in the NOD mouse model.

Preferred antibodies of the invention are human monoclonal antibodies. Additionally or alternatively, the antibodies can be, for example, chimeric or humanized monoclonal antibodies.

Monoclonal Antibody LAG3.5

A preferred antibody of the invention is the human monoclonal antibody, LAG3.5, structurally and chemically characterized as described below and in the following Examples. The $V_H$ amino acid sequence of LAG3.5 is shown in SEQ ID NO: 12 (FIG. 2A). The $V_L$ amino acid sequence of LAG3.5 is shown in SEQ ID NO: 14 (FIG. 2B).

The $V_H$ and $V_L$ sequences (or CDR sequences) of other anti-LAG-3 antibodies which bind human LAG-3 can be "mixed and matched" with the $V_H$ and $V_L$ sequences (or CDR sequences) of antibody LAG3.5. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one embodiment, antibodies of the invention, or antigen binding portions thereof, comprise:

(a) a heavy chain variable region comprising amino acid sequence SEQ ID NO: 12 (i.e., the $V_H$ of LAG3.5); and (b) a light chain variable region comprising amino acid sequence SEQ ID NO: 14 (i.e., the $V_L$ of LAG3.5) or the $V_L$ of another anti-LAG3 antibody (i.e., which differs from LAG3.5);

wherein the antibody specifically binds human LAG-3.

In another embodiment, antibodies of the invention, or antigen binding portions thereof, comprise:

(a) the CDR1, CDR2, and CDR3 regions of the heavy chain variable region comprising amino acid sequence SEQ ID NO: 12 (i.e., the CDR sequences of LAG3.5, SEQ ID NOs:15, 16, and 17, respectively); and (b) the CDR1, CDR2, and CDR3 regions of the light chain variable region comprising amino acid sequence SEQ ID NO: 14 (i.e., the CDR sequences of LAG3.5, SEQ ID NOs:18, 19, and 20, respectively) or the CDRs of another anti-LAG3 antibody (i.e., which differs from LAG3.5);

wherein the antibody specifically binds human LAG-3.

In yet another embodiment, the antibody, or antigen binding portion thereof, includes the heavy chain variable CDR2 region of LAG3.5 combined with CDRs of other antibodies which bind human LAG-3, e.g., a CDR1 and/or CDR3 from the heavy chain variable region, and/or a CDR1, CDR2, and/or CDR3 from the light chain variable region of a different anti-LAG-3 antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al., *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIAjournal* 8: Scientific Review 8 (2001); Igarashi et al., *J. Biochem* (Tokyo) 117:452-7 (1995); Bourgeois et al., *J. Virol* 72:807-10 (1998); Levi et al., *Proc. Natl. Acad. Sci. U.S.A.* 90:4374-8 (1993); Polymenis and Stoller, *J. Immunol.* 152: 5218-5329 (1994) and Xu and Davis, *Immunity* 13:37-45 (2000). See also, U.S. Pat. Nos. 6,951,646; 6,914,128; 6,090,382; 6,818,216; 6,156,313; 6,827,925; 5,833,943;

5,762,905 and 5,760,185. Each of these references is hereby incorporated by reference in its entirety.

Accordingly, in another embodiment, antibodies of the invention include the CDR2 of the heavy chain variable region of LAG3.5 and at least the CDR3 of the heavy and/or light chain variable region of LAG3.5 (SEQ ID NOs: 17 and/or 20), or the CDR3 of the heavy and/or light chain variable region of another LAG-3 antibody, wherein the antibody is capable of specifically binding to human LAG-3. These antibodies preferably (a) compete for binding with; (b) retain the functional characteristics; (c) bind to the same epitope; and/or (d) have a similar binding affinity as LAG3.5. In yet another embodiment, the antibodies further may include the CDR2 of the light chain variable region of LAG3.5 (SEQ ID NOs: 17 and/or 20), or the CDR2 of the light chain variable region of another LAG-3 antibody, wherein the antibody is capable of specifically binding to human LAG-3. In another embodiment, the antibodies of the invention further may include the CDR1 of the heavy and/or light chain variable region of LAG3.5 (SEQ ID NOs: 17 and/or 20), or the CDR1 of the heavy and/or light chain variable region of another LAG-3 antibody, wherein the antibody is capable of specifically binding to human LAG-3.

Conservative Modifications

In another embodiment, antibodies of the invention comprise a heavy and/or light chain variable region sequences of CDR1, CDR2 and CDR3 sequences which differ from those of LAG3.5 by one or more conservative modifications. In a preferred embodiment, however, residues 54 and 56 of the $V_H$ CDR2 remain as arginine and serine, respectively (i.e., are not mutated). It is understood in the art that certain conservative sequence modification can be made which do not remove antigen binding. See, e.g., Brummell et al. (1993) Biochem 32:1180-8; de Wildt et al. (1997) Prot. Eng. 10:835-41; Komissarov et al. (1997) J. Biol. Chem. 272: 26864-26870; Hall et al. (1992) J. Immunol. 149:1605-12; Kelley and O'Connell (1993) Biochem. 32:6862-35; Adib-Conquy et al. (1998) Int. Immunol. 10:341-6 and Beers et al. (2000) Clin. Can. Res. 6:2835-43. Accordingly, in one embodiment, the antibody comprises a heavy chain variable region comprising CDR1, CDR2, and CDR3 sequences and/or a light chain variable region comprising CDR1, CDR2, and CDR3 sequences, wherein:

(a) the heavy chain variable region CDR1 sequence comprises SEQ ID NO: 15, and/or conservative modifications thereof, except at positions 54 and 56; and/or (b) the heavy chain variable region CDR3 sequence comprises SEQ ID NO: 17, and conservative modifications thereof; and/or (c) the light chain variable region CDR1, and/or CDR2, and/or CDR3 sequences comprise SEQ ID NO: 18, and/or, SEQ ID NO: 19, and/or SEQ ID NO: 20, and/or conservative modifications thereof; and (d) the antibody specifically binds human LAG-3.

Additionally or alternatively, the antibody can possess one or more of the following functional properties described above, such as high affinity binding to human LAG-3, binding to monkey LAG-3, lack of binding to mouse LAG-3, the ability to inhibit binding of LAG-3 to MHC Class II molecules and/or the ability to stimulate antigen-specific T cell responses.

In various embodiments, the antibody can be, for example, a human, humanized or chimeric antibody As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth above) using the functional assays described herein.

Engineered and Modified Antibodies

Antibodies of the invention can be prepared using an antibody having one or more of the $V_H$ and/or $V_L$ sequences of LAG3.5 as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al. (1998) Nature 332:323-327; Jones et al. (1986) Nature 321:522-525; Queen et al. (1989) Proc. Natl. Acad. See. U.S.A. 86:10029-10033; U.S. Pat. Nos. 5,225, 539; 5,530,101; 5,585,089; 5,693,762 and 6,180,370).

Accordingly, another embodiment of the invention pertains to an isolated monoclonal antibody, or antigen binding portion thereof, comprising a heavy chain variable region comprising CDR1, CDR2, and CDR3 sequences comprising SEQ ID NOs: 15, 16, 17, respectively, and/or a light chain variable region comprising CDR1, CDR2, and CDR3 sequences comprising SEQ ID NOs: 18, 19, 20, respectively (i.e., the CDRs of LAG3.5). While these antibodies contain the $V_H$ and $V_L$ CDR sequences of monoclonal antibody LAG3.5, they can contain differing framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al. (1991), cited supra; Tomlinson et al. (1992) "The Repertoire of Human Germline $V_H$ Sequences Reveals about Fifty Groups of $V_H$ Segments with Different Hypervariable Loops" *J. Mol. Biol.* 227:776-798; and Cox et al. (1994) "A Directory of Human Germ-line $V_H$ Segments Reveals a Strong Bias in their Usage" *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG_0010109, NT_024637 & BC070333), 3-33 (NG_0010109 & NT_024637) and 3-7 (NG_0010109 & NT_024637). As another example, the following heavy chain germline sequences found in the HCo12 HuMAb mouse are available in the accompanying Genbank Accession Nos.: 1-69 (NG_0010109, NT_024637 & BC070333), 5-51 (NG_0010109 & NT_024637), 4-34 (NG_0010109 & NT_024637), 3-30.3 (CAJ556644) & 3-23 (AJ406678).

Antibody protein sequences are compared against a compiled protein sequence database using one of the sequence similarity searching methods called the Gapped BLAST (Altschul et al. (1997), supra), which is well known to those skilled in the art.

Preferred framework sequences for use in the antibodies of the invention are those that are structurally similar to the framework sequences used by selected antibodies of the invention, e.g., similar to the $V_H$ 4-34 framework sequences and/or the $V_K$ L6 framework sequences used by preferred monoclonal antibodies of the invention. The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations can be amino acid substitutions, additions or deletions, but are preferably substitutions. Moreover, typically no more than one, two, three, four or five residues within a CDR region are altered.

Accordingly, in another embodiment, the invention provides isolated anti-LAG-3 monoclonal antibodies, or antigen binding portions thereof, comprising a heavy chain variable region comprising: (a) a $V_H$ CDR1 region comprising SEQ ID NO: 15, or an amino acid sequence having one, two, three, four or five amino acid substitutions, deletions or additions as compared to SEQ ID NO: 15; (b) a $V_H$ CDR2 region comprising SEQ ID NO: 16, or an amino acid sequence having one, two, three, four or five amino acid substitutions, deletions or additions as compared to SEQ ID NO: 16 (preferably wherein positions 54 and 56 are the same as in SEQ ID NO:16); (c) a $V_H$ CDR3 region comprising SEQ ID NO: 17, or an amino acid sequence having one, two, three, four or five amino acid substitutions, deletions or additions as compared to SEQ ID NO: 17; (d) a $V_L$ CDR1 region comprising SEQ ID NO: 18, or an amino acid sequence having one, two, three, four or five amino acid substitutions, deletions or additions as compared to SEQ ID NO: 18; (e) a $V_L$ CDR2 region comprising SEQ ID NO: 19, or an amino acid sequence having one, two, three, four or five amino acid substitutions, deletions or additions as compared to SEQ ID NO: 19; and (f) a $V_L$ CDR3 region comprising SEQ ID NO: 20, or an amino acid sequence having one, two, three, four or five amino acid substitutions, deletions or additions as compared to SEQ ID NO: 20.

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition or alternative to modifications made within the framework or CDR regions, antibodies of the invention can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention can be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In a preferred embodiment, the antibody is an IgG4 isotype antibody comprising a Serine to Proline mutation at a position corresponding to position 228 (S228P; EU index) in the hinge region of the heavy chain constant region. This mutation has been reported to abolish the heterogeneity of inter-heavy chain disulfide bridges in the hinge region (Angal et al. supra; position 241 is based on the Kabat numbering system).

In one embodiment, the hinge region of CH1 is modified such that the number of cysteine residues in the hinge region is altered, e.g., increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In another embodiment, the antibody is modified to increase its biological half life. Various approaches are possible. For example, one or more of the following mutations can be introduced: T252L, T254S, T256F, as described in U.S. Pat. No. 6,277,375. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551.

In another example, one or more amino acid residues within amino acid positions 231 and 239 are altered to thereby alter the ability of the antibody to fix complement. This approach is described further in PCT Publication WO 94/29351.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described (see Shields et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 ($\alpha$(1,6)-fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 and Yamane-Ohnuki et al. (2004) *Biotechnol Bioeng* 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the $\alpha$-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al. (2002) *J. Biol. Chem.* 277:26733-26740). Antibodies with a modified glycosylation profile can also be produced in chicken eggs, as described in PCT Publication WO 06/089231. Alternatively, antibodies with a modified glycosylation profile can be produced in plant cells, such as *Lemna*. Methods for production of antibodies in a plant system are disclosed in the U.S. patent application corresponding to Alston & Bird LLP 60/836,998 filed on Aug. 11, 2006. PCT Publication WO 99/54342 describes cell lines engineered to express glycoprotein-modifying glycosyl transferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody can be cleaved off using a fucosidase enzyme; e.g., the fucosidase α-L-fucosidase removes fucosyl residues from antibodies (Tarentino et al. (1975) *Biochem.* 14:5516-23).

Another modification of the antibodies herein that is contemplated by this disclosure is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, e.g., EP 0 154 316 and EP 0 401 384.

Antibody Physical Properties

Antibodies of the invention can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) Annu Rev Biochem 41:673-702; Gala and Morrison (2004) J Immunol 172:5489-94; Wallick et al (1988) J Exp Med 168:1099-109; Spiro (2002) Glycobiology 12:43R-56R; Parekh et al (1985) Nature 316:452-7; Mimura et al. (2000) Mol Immunol 37:697-706). Glycosylation has been known to occur at motifs containing an N-X-S/T sequence. In some instances, it is preferred to have an anti-LAG-3 antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-LAG-3 antibody that contains a pI value that falls in the normal range. This can be achieved either by selecting antibodies with a pI in the normal range or by mutating charged surface residues.

Nucleic Acid Molecules Encoding Antibodies of the Invention

In another aspect, the invention provides nucleic acid molecules that encode heavy and/or light chain variable regions, or CDRs, of the antibodies of the invention. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, Ausubel, et al., ed. (1987) Current Protocols in Molecular Biology, Greene Publishing and Wiley Interscience, New York. A nucleic acid of the invention can be, e.g., DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the invention include those encoding the $V_H$ and $V_L$ sequences of LAG3.5 monoclonal antibody (SEQ ID NOs: 12 and 14, respectively) or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat et al. (1991), supra) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (see e.g., Kabat et al., supra) and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly$_4$-Ser)$_3$ (SEQ ID NO: 28), such that the $V_H$ and $V_L$ sequences can be expressed as a contiguous single-chain protein, with the $V_L$ and $V_H$ regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Production of Monoclonal Antibodies of the Invention

Monoclonal antibodies (mAbs) of the present invention can be produced using the well-known somatic cell hybridization (hybridoma) technique of Kohler and Milstein (1975) Nature 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

In a preferred embodiment, the antibodies of the invention are human monoclonal antibodies. Such human monoclonal antibodies directed against human LAG-3 can be generated using transgenic or transchromosomic mice carrying parts of the human immune system rather than the mouse system. These transgenic and transchromosomic mice include mice referred to herein as the HuMAb Mouse® and KM Mouse®, respectively, and are collectively referred to herein as "human Ig mice."

The HuMAb Mouse® (Medarex®, Inc.) contains human immunoglobulin gene miniloci that encode unrearranged human heavy ($\mu$ and $\gamma$) and $\kappa$ light chain immunoglobulin sequences, together with targeted mutations that inactivate the endogenous $\mu$ and $\kappa$ chain loci (see e.g., Lonberg et al. (1994) *Nature* 368(6474): 856-859). Accordingly, the mice exhibit reduced expression of mouse IgM or $\kappa$, and in response to immunization, the introduced human heavy and light chain transgenes undergo class switching and somatic mutation to generate high affinity human IgG$\kappa$ monoclonal antibodies (Lonberg et al. (1994), supra; reviewed in Lonberg (1994) *Handbook of Experimental Pharmacology* 113: 49-101; Lonberg, N. and Huszar, D. (1995) *Intern. Rev. Immunol.* 13: 65-93, and Harding and Lonberg (1995) *Ann. N.Y. Acad. Sci.* 764:536-546). Preparation and use of the HuMAb Mouse®, and the genomic modifications carried by such mice, is further described in Taylor et al. (1992) *Nucleic Acids Research* 20:6287-6295; Chen et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen et al. (1993) *EMBO J.* 12: 821-830; Tuaillon et al. (1994) *J. Immunol.* 152:2912-2920; Taylor et al. (1994) *International Immunology* 6: 579-591; and Fishwild et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807; PCT Publication Nos. WO 92/03918; WO 93/12227; WO 94/25585; WO 97/13852; WO 98/24884; WO 99/45962 and WO 01/14424, the contents of which are incorporated herein by reference in their entirety.

In another embodiment, human antibodies of the invention can be raised using a mouse that carries human immunoglobulin sequences on transgenes and transchomosomes, such as a mouse that carries a human heavy chain transgene and a human light chain transchromosome. This mouse is referred to herein as a "KM Mouse®," and is described in detail in PCT Publication WO 02/43478. A modified form of this mouse, which further comprises a homozygous disruption of the endogenous Fc$\gamma$RIIIB receptor gene, is also described in PCT Publication WO 02/43478 and referred to herein as a "KM/FCGR2D Mouse®." In addition, mice with either the HCo7 or HCo12 heavy chain transgenes or both can be used.

Additional transgenic animal embodiments include the Xenomouse (Abgenix, Inc., U.S. Pat. Nos. 5,939,598; 6,075,181; 6,114,598; 6,150,584 and 6,162,963). Further embodiments include "TC mice" (Tomizuka et al. (2000) *Proc. Natl. Acad. Sci. USA* 97:722-727) and cows carrying human heavy and light chain transchromosomes (Kuroiwa et al. (2002) *Nature Biotechnology* 20:889-894; PCT Publication WO 02/092812). The contents of these patents and publications are specifically incorporated herein by reference in their entirety.

In one embodiment, human monoclonal antibodies of the invention are prepared using phage display methods for screening libraries of human immunoglobulin genes. See, e.g. U.S. Pat. Nos. 5,223,409; 5,403,484; 5,571,698; 5,427,908; 5,580,717; 5,969,108; 6,172,197; 5,885,793; 6,521,404; 6,544,731; 6,555,313; 6,582,915; and 6,593,081, the contents of which are incorporated herein by reference in their entirety.

Human monoclonal antibodies of the invention can also be prepared using SCID mice into which human immune cells have been reconstituted such that a human antibody response can be generated upon immunization. See, e.g., U.S. Pat. Nos. 5,476,996 and 5,698,767, the contents of which are incorporated herein by reference in their entirety.

In another embodiment, human anti-LAG-3 antibodies are prepared using phage display where the phages comprise nucleic acids encoding antibodies generated in transgenic animals previously immunized with LAG-3. In a preferred embodiment, the transgenic animal is a HuMab, KM, or Kirin mouse. See, e.g. U.S. Pat. No. 6,794,132, the contents of which are incorporated herein by reference in its entirety.

Immunization of Human Ig Mice

In one embodiment of the invention, human Ig mice are immunized with a purified or enriched preparation of a LAG-3 antigen, recombinant LAG-3 protein, or cells expressing a LAG-3 protein. See, e.g., Lonberg et al. (1994), supra; Fishwild et al. (1996), supra; PCT Publications WO 98/24884 or WO 01/14424, the contents of which are incorporated herein by reference in their entirety. In a preferred embodiment, 6-16 week old mice are immunized with 5-50 µg of LAG-3 protein. Alternatively, a portion of LAG-3 fused to a non-LAG-3 polypeptide is used.

In one embodiment, the transgenic mice are immunized intraperitoneally (IP) or intravenously (IV) with LAG-3 antigen in complete Freund's adjuvant, followed by subsequent IP or IV immunizations with antigen in incomplete Freund's adjuvant. In other embodiments, adjuvants other than Freund's or whole cells in the absence of adjuvant are used. The plasma can be screened by ELISA and cells from mice with sufficient titers of anti-LAG-3 human immunoglobulin can be used for fusions.

Generation of Hybridomas Producing Human Monoclonal Antibodies of the Invention

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. Generation of hybridomas is well-known in the art. See, e.g., Harlow and Lane (1988) *Antibodies, A Laboratory Manual*, Cold Spring Harbor Publications, New York.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) *Science* 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody chain genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al. (1988) *Mol. Cell. Biol.* 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the invention can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr⁻ CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Immunoconjugates

Antibodies of the invention can be conjugated to a therapeutic agent to form an immunoconjugate such as an antibody-drug conjugate (ADC). Suitable therapeutic agents include antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val (SEQ ID NO: 39), Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038658; WO 07/051081; WO 07/059404; WO 08/083312; and WO 08/103693; U.S. Patent Publications 20060024317; 20060004081; and 20060247295; the disclosures of which are incorporated herein by reference.

Bispecific Molecules

In another aspect, the present disclosure features bispecific molecules comprising one or more antibodies of the invention linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities. In a preferred embodiment, the bispecific molecule comprises a first binding specificity for LAG-3 and a second binding specificity for a triggering molecule that recruits cytotoxic effector cells that can kill a LAG-3 expressing target cell. Examples of suitable triggering molecules are CD64, CD89, CD16, and CD3. See, e.g., Kufer et al., *TRENDS in Biotechnology,* 22 (5), 238-244 (2004).

In an embodiment, a bispecific molecule has, in addition to an anti-Fc binding specificity and an anti-LAG-3 binding specificity, a third specificity. The third specificity can be for an anti-enhancement factor (EF), e.g., a molecule that binds to a surface protein involved in cytotoxic activity and thereby increases the immune response against the target cell. For example, the anti-enhancement factor can bind a cytotoxic T-cell (e.g. via CD2, CD3, CD8, CD28, CD4, CD40, or ICAM-1) or other immune cell, resulting in an increased immune response against the target cell.

Bispecific molecules can come in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv)$_2$ construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al, cited supra; Cao and Suresh, *Bioconjugate Chemistry*, 9 (6), 635-644 (1998); and van Spriel et al., *Immunology Today*, 21 (8), 391-397 (2000), and the references cited therein.

Pharmaceutical Compositions

In another aspect, the present disclosure provides a pharmaceutical composition comprising one or more antibodies of the present invention formulated together with a pharmaceutically acceptable carrier. The composition may optionally contain one or more additional pharmaceutically active ingredients, such as another antibody or a drug. The pharmaceutical compositions of the invention also can be administered in a combination therapy with, for example, another immunostimulatory agent, anti-cancer agent, an anti-viral agent, or a vaccine, such that the anti-LAG-3 antibody enhances the immune response against the vaccine.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: *The Science and Practice of Pharmacy*, 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active compound can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, e.g., intranasally, orally, vaginally, rectally, sublingually or topically.

The pharmaceutical compositions of the invention can include pharmaceutically acceptable salts. A "pharmaceutically acceptable salt" refers to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Alternatively, antibody can be administered as a sustained release formulation, in which case less frequent administration is required.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-LAG-3 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 µg/ml and in some methods about 25-300 µg/ml.

A "therapeutically effective dosage" of an anti-LAG-3 antibody of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., *Sustained and Controlled Release Drug Delivery Systems*, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparati (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the human monoclonal antibodies of the invention can be formulated to ensure proper distribution in vivo. For example, to ensure that the therapeutic compounds of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al. (1995) *FEBS Lett.* 357:140; M. Owais et al. (1995) *Antimicrob. Agents Chemother.* 39:180; Briscoe et al. (1995) *Am. J. Physiol.* 1233:134; Schreier et al. (1994) *J. Biol. Chem.* 269:9090; Keinanen and Laukkanen (1994) *FEBS Lett.* 346:123; and Killion and Fidler (1994) *Immunomethods* 4:273.

Uses and Methods of the Invention

Antibodies (compositions, bispecifics, and immunoconjugates) of the present invention have numerous in vitro and in vivo utilities involving, for example, detection of LAG-3 or enhancement of immune responses by blockade of LAG-3. In a preferred embodiment, the antibodies are human antibodies. Such antibodies can be administered to cells in culture, in vitro or ex vivo, or to human subjects, e.g., in vivo, to enhance immunity in a variety of situations. Accordingly, in one aspect, the invention provides a method of modifying an immune response in a subject comprising administering to the subject the antibody, or antigen-binding portion thereof, of the invention such that the immune response in the subject is modified. Preferably, the response is enhanced, stimulated or up-regulated.

Preferred subjects include human patients in need of enhancement of an immune response. The methods are particularly suitable for treating human patients having a disorder that can be treated by augmenting an immune response (e.g., the T-cell mediated immune response). In a particular embodiment, the methods are particularly suitable for treatment of cancer in vivo. To achieve antigen-specific enhancement of immunity, the anti-LAG-3 antibodies can be administered together with an antigen of interest or the antigen may already be present in the subject to be treated (e.g., a tumor-bearing or virus-bearing subject). When antibodies to LAG-3 are administered together with another agent, the two can be administered in either order or simultaneously.

The invention further provides methods for detecting the presence of human LAG-3 antigen in a sample, or measuring the amount of human LAG-3 antigen, comprising contacting the sample, and a control sample, with a human monoclonal antibody, or an antigen binding portion thereof, which specifically binds to human LAG-3, under conditions that allow for formation of a complex between the antibody or portion thereof and human LAG-3. The formation of a complex is then detected, wherein a difference complex formation between the sample compared to the control sample is indicative the presence of human LAG-3 antigen in the sample. Moreover, the anti-LAG-3 antibodies of the invention can be used to purify human LAG-3 via immunoaffinity purification.

Given the ability of anti-LAG-3 antibodies of the invention to inhibit the binding of LAG-3 to WIC Class II molecules and to stimulate antigen-specific T cell responses, the invention also provides in vitro and in vivo methods of using the antibodies to stimulate, enhance or upregulate antigen-specific T cell responses. For example, the invention provides a method of stimulating an antigen-specific T cell response comprising contacting said T cell with an antibody of the invention, such that an antigen-specific T cell response is stimulated. Any suitable indicator of an antigen-specific T cell response can be used to measure the antigen-specific T cell response. Non-limiting examples of such suitable indicators include increased T cell proliferation in the presence of the antibody and/or increase cytokine production in the presence of the antibody. In a preferred embodiment, interleukin-2 production by the antigen-specific T cell is stimulated.

The invention also provides method for stimulating an immune response (e.g., an antigen-specific T cell response) in a subject comprising administering an antibody of the invention to the subject such that an immune response (e.g., an antigen-specific T cell response) in the subject is stimulated. In a preferred embodiment, the subject is a tumor-bearing subject and an immune response against the tumor is stimulated. In another preferred embodiment, the subject is a virus-bearing subject and an immune response against the virus is stimulated.

In another embodiment, the invention provides methods for inhibiting growth of tumor cells in a subject comprising administering to the subject an antibody of the invention such that growth of the tumor is inhibited in the subject. In yet another embodiment, the invention provides methods for treating a viral infection in a subject comprising administering to the subject an antibody of the invention such that the viral infection is treated in the subject.

These and other methods of the invention are discussed in further detail below.

Cancer

Blockade of LAG-3 by antibodies can enhance the immune response to cancerous cells in the patient. In one aspect, the present invention relates to treatment of a subject in vivo using an anti-LAG-3 antibody such that growth of cancerous tumors is inhibited. An anti-LAG-3 antibody can be used alone to inhibit the growth of cancerous tumors. Alternatively, an anti-LAG-3 antibody can be used in conjunction with other immunogenic agents, standard cancer treatments, or other antibodies, as described below.

Accordingly, in one embodiment, the invention provides a method of inhibiting growth of tumor cells in a subject, comprising administering to the subject a therapeutically effective amount of an anti-LAG-3 antibody, or antigen-binding portion thereof. Preferably, the antibody is a human anti-LAG-3 antibody (such as any of the human anti-human LAG-3 antibodies described herein). Additionally or alternatively, the antibody can be a chimeric or humanized anti-LAG-3 antibody.

Preferred cancers whose growth may be inhibited using the antibodies of the invention include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the invention includes refractory or recurrent malignancies whose growth may be inhibited using the antibodies of the invention.

Examples of other cancers that can be treated using the methods of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers, especially metastatic cancers that express PD-L1 (Iwai et al. (2005) *Int. Immunol.* 17:133-144).

Optionally, antibodies to LAG-3 can be combined with an immunogenic agent, such as cancerous cells, purified tumor antigens (including recombinant proteins, peptides, and carbohydrate molecules), cells, and cells transfected with genes encoding immune stimulating cytokines (He et al (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

In humans, some tumors have been shown to be immunogenic such as melanomas. By raising the threshold of T cell activation by LAG-3 blockade, the tumor responses in the host can be activated.

LAG-3 blockade is likely to be more effective when combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita et al. (eds.), 1997, Cancer: Principles and Practice of Oncology, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci U.S.A.* 90: 3539-43).

The study of gene expression and large scale gene expression patterns in various tumors has led to the definition of so called tumor specific antigens (Rosenberg, S A (1999) *Immunity* 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. LAG-3 blockade can be used in conjunction with a collection of recombinant proteins and/or peptides expressed in a tumor in order to generate an immune response to these proteins. These proteins are normally viewed by the immune system as self antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) *Science* 266: 2011-2013). (These somatic tissues may be protected from immune attack by various means). Tumor antigen can also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines can include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which can be used in conjunction with LAG-3 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) *Science* 269:1585-1588; Tamura et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle et al. (1998) *Nature Medicine* 4: 328-332). DCs can also be transduced by genetic means to express these tumor antigens as well. DCs have also been fused directly to tumor cells for the purposes of immunization (Kugler et al. (2000) *Nature Medicine* 6:332-336). As a method of vaccination, DC immunization can be effectively combined with LAG-3 blockade to activate more potent anti-tumor responses.

LAG-3 blockade can also be combined with standard cancer treatments. LAG-3 blockade can be effectively combined with chemotherapeutic regimes. In these instances, it may be possible to reduce the dose of chemotherapeutic reagent administered (Mokyr et al. (1998) *Cancer Research* 58: 5301-5304). An example of such a combination is an anti-LAG-3 antibody in combination with decarbazine for the treatment of melanoma. Another example of such a combination is an anti-LAG-3 antibody in combination with interleukin-2 (IL-2) for the treatment of melanoma. The scientific rationale behind the combined use of LAG-3 blockade and chemotherapy is that cell death, that is a consequence of the cytotoxic action of most chemotherapeutic compounds, should result in increased levels of tumor antigen in the antigen presentation pathway. Other combination therapies that may result in synergy with LAG-3 blockade through cell death are radiation, surgery, and hormone deprivation. Each of these protocols creates a source of tumor antigen in the host. Angiogenesis inhibitors can also be combined with LAG-3 blockade. Inhibition of angiogenesis leads to tumor cell death which may feed tumor antigen into host antigen presentation pathways.

LAG-3 blocking antibodies can also be used in combination with bispecific antibodies that target Fcα or Fcγ receptor-expressing effectors cells to tumor cells (see, e.g., U.S. Pat. Nos. 5,922,845 and 5,837,243). Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would be augmented by the use of LAG-3 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). Antibodies to each of these entities can be used in combination with anti-LAG-3 to counteract the effects of the immunosuppressive agent and favor tumor immune responses by the host.

Other antibodies which activate host immune responsiveness can be used in combination with anti-LAG-3. These include molecules on the surface of dendritic cells which activate DC function and antigen presentation. Anti-CD40 antibodies are able to substitute effectively for T cell helper activity (Ridge et al. (1998) *Nature* 393: 474-478) and can be used in conjunction with LAG-3 antibodies (Ito et al. (2000) *Immunobiology* 201 (5) 527-40). Activating antibodies to T cell costimulatory molecules such as CTLA-4 (e.g., U.S. Pat. No. 5,811,097), OX-40 (Weinberg et al. (2000) *Immunol* 164: 2160-2169), 4-1BB (Melero et al. (1997) *Nature Medicine* 3: 682-685 (1997), and ICOS (Hutloff et al. (1999) *Nature* 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. LAG-3 blockade can be used to increase the effectiveness of the donor engrafted tumor specific T cells.

There are also several experimental treatment protocols that involve ex vivo activation and expansion of antigen specific T cells and adoptive transfer of these cells into recipients in order to stimulate antigen-specific T cells against tumor (Greenberg & Riddell (1999) *Science* 285: 546-51). These methods can also be used to activate T cell responses to infectious agents such as CMV. Ex vivo activation in the presence of anti-LAG-3 antibodies can increase the frequency and activity of the adoptively transferred T cells.

Infectious Diseases

Other methods of the invention are used to treat patients that have been exposed to particular toxins or pathogens. Accordingly, another aspect of the invention provides a method of treating an infectious disease in a subject comprising administering to the subject an anti-LAG-3 antibody, or antigen-binding portion thereof, such that the subject is treated for the infectious disease. Preferably, the antibody is a human anti-human LAG-3 antibody (such as any of the human anti-LAG-3 antibodies described herein). Additionally or alternatively, the antibody can be a chimeric or humanized antibody.

Similar to its application to tumors as discussed above, antibody mediated LAG-3 blockade can be used alone, or as an adjuvant, in combination with vaccines, to stimulate the immune response to pathogens, toxins, and self-antigens. Examples of pathogens for which this therapeutic approach can be particularly useful, include pathogens for which there is currently no effective vaccine, or pathogens for which conventional vaccines are less than completely effective. These include, but are not limited to HIV, Hepatitis (A, B, & C), Influenza, Herpes, Giardia, Malaria, *Leishmania, Staphylococcus aureus, Pseudomonas aeruginosa*. LAG-3 blockade is particularly useful against established infections by agents such as HIV that present altered antigens over the course of the infections. These novel epitopes are recognized as foreign at the time of anti-human LAG-3 administration, thus provoking a strong T cell response that is not dampened by negative signals through LAG-3.

Some examples of pathogenic viruses causing infections treatable by methods of the invention include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the invention include *chlamydia*, rickettsial bacteria, mycobacteria, staphylococci, streptococci, pneumonococci, meningococci and gonococci, *klebsiella, proteus, serratia, pseudomonas, legionella*, diphtheria, *salmonella*, bacilli, cholera, tetanus, botulism, anthrax, plague, leptospirosis, and Lymes disease bacteria.

Some examples of pathogenic fungi causing infections treatable by methods of the invention include *Candida (albicans, krusei, glabrata, tropicalis*, etc.), *Cryptococcus neoformans, Aspergillus (fumigatus, niger*, etc.), Genus *Mucorales (mucor, absidia, rhizopus), Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the invention include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii, Nippostrongylus brasiliensis*.

In all of the above methods, LAG-3 blockade can be combined with other forms of immunotherapy such as cytokine treatment (e.g., interferons, GM-CSF, G-CSF, or bispecific antibody therapy, which provides for enhanced presentation of tumor antigens (see, e.g., Holliger (1993) *Proc. Natl. Acad. Sci.* USA 90:6444-6448; Poljak (1994) Structure 2:1121-1123).

Autoimmune Reactions

Anti-LAG-3 antibodies may provoke and amplify autoimmune responses. Indeed, induction of anti-tumor responses using tumor cell and peptide vaccines reveals that many anti-tumor responses involve anti-self reactivities (van Elsas et al. (2001) *J. Exp. Med.* 194:481-489; Overwijk, et al. (1999) *Proc. Natl. Acad. Sci. U.S.A.* 96: 2982-2987; Hurwitz, (2000) supra; Rosenberg & White (1996) *J. Immunother Emphasis Tumor Immunol* 19 (1): 81-4). Therefore, it is possible to consider using anti-LAG-3 blockade in conjunction with various self proteins in order to devise vaccination protocols to efficiently generate immune responses against these self proteins for disease treatment. For example, Alzheimer's disease involves inappropriate accumulation of Aβ peptide in amyloid deposits in the brain; antibody responses against amyloid are able to clear these amyloid deposits (Schenk et al., (1999) *Nature* 400: 173-177).

Other self proteins can also be used as targets such as IgE for the treatment of allergy and asthma, and TNFα for rheumatoid arthritis. Finally, antibody responses to various hormones may be induced by the use of anti-LAG-3 antibody. Neutralizing antibody responses to reproductive hormones can be used for contraception. Neutralizing antibody response to hormones and other soluble factors that are required for the growth of particular tumors can also be considered as possible vaccination targets.

Analogous methods as described above for the use of anti-LAG-3 antibody can be used for induction of therapeutic autoimmune responses to treat patients having an inappropriate accumulation of other self-antigens, such as amyloid deposits, including Aβ in Alzheimer's disease, cytokines such as TNFα, and IgE.

Vaccines

Anti-LAG-3 antibodies can be used to stimulate antigen-specific immune responses by coadministration of an anti-LAG-3 antibody with an antigen of interest (e.g., a vaccine). Accordingly, in another aspect the invention provides a method of enhancing an immune response to an antigen in a subject, comprising administering to the subject: (i) the antigen; and (ii) an anti-LAG-3 antibody, or antigen-binding portion thereof, such that an immune response to the antigen in the subject is enhanced. Preferably, the antibody is a human anti-human LAG-3 antibody (such as any of the human anti-LAG-3 antibodies described herein). Additionally or alternatively, the antibody can be a chimeric or humanized antibody. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

Suitable routes of administering the antibody compositions (e.g., human monoclonal antibodies, multispecific and bispecific molecules and immunoconjugates) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-LAG-3 antibodies of the invention can be co-administered with one or other more therapeutic agents, e.g., a cytotoxic agent, a radiotoxic agent or an immunosuppressive agent. The antibody can be linked to the agent (as an immuno-complex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, dacarbazine and cyclophosphamide hydroxyurea which, by themselves, are only effective at levels which are toxic or subtoxic to a patient. Cisplatin is intravenously administered as a 100 mg/ml dose once every four weeks and adriamycin is intravenously administered as a 60-75 mg/ml dose once every 21 days. Co-administration of the human anti-LAG-3 antibodies, or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Also within the scope of the present invention are kits comprising the antibody compositions of the invention (e.g., human antibodies, bispecific or multispecific molecules, or immunoconjugates) and instructions for use. The kit can further contain at least one additional reagent, or one or more additional human antibodies of the invention (e.g., a human antibody having a complementary activity which binds to an epitope in LAG-3 antigen distinct from the first human antibody). Kits typically include a label indicating the intended use of the contents of the kit. The term label includes any writing, or recorded material supplied on or with the kit, or which otherwise accompanies the kit.

Combination Therapy

In another aspect, the invention provides methods of combination therapy in which an anti-LAG-3 antibody (or antigen-binding portion thereof) of the present invention is coadministered with one or more additional antibodies that are effective in stimulating immune responses to thereby further enhance, stimulate or upregulate immune responses in a subject. In one embodiment, the invention provides a method for stimulating an immune response in a subject comprising administering to the subject an anti-LAG-3 antibody and one or more additional immunostimulatory antibodies, such as an anti-PD-1 antibody, an anti-PD-L1 antibody and/or an anti-CTLA-4 antibody, such that an immune response is stimulated in the subject, for example to inhibit tumor growth or to stimulate an anti-viral response. In another embodiment, the subject is administered an anti-LAG-3 antibody and an anti-PD-1 antibody. In still another embodiment, the subject is administered an anti-LAG-3 antibody and an anti-PD-L1 antibody. In yet another embodiment, the subject is administered an anti-LAG-3 antibody and an anti-CTLA-4 antibody. In one embodiment, the anti-LAG-3 antibody is a human antibody, such as an antibody of the disclosure. Alternatively, the anti-LAG-3 antibody can be, for example, a chimeric or humanized antibody (e.g., prepared from a mouse anti-LAG-3 mAb). In another embodiment, the at least one additional immunostimulatory antibody (e.g., anti-PD-1, anti-PD-L1 and/or anti-CTLA-4 antibody) is a human antibody. Alternatively, the at least one additional immunostimulatory antibody can be, for example, a chimeric or humanized antibody (e.g., prepared from a mouse anti-PD-1, anti-PD-L1 and/or anti-CTLA-4 antibody).

In another embodiment, the invention provides a method for treating a hyperproliferative disease (e.g., cancer), comprising administering a LAG-3 antibody and a CTLA-4 antibody to a subject. In further embodiments, the anti-LAG-3 antibody is administered at a subtherapeutic dose, the anti-CTLA-4 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering an anti-LAG-3 antibody and a subtherapeutic dose of anti-CTLA-4 antibody to a subject. In certain embodiments, the subject is human. In other embodiments, the anti-CTLA-4 antibody is human sequence monoclonal antibody 10D1 (described in PCT Publication WO 01/14424) and the anti-LAG-3 antibody is human sequence monoclonal antibody, such as LAG3.5 described herein. Other anti-CTLA-4 antibodies encompassed by the methods of the present invention include, for example, those disclosed in: WO 98/42752; WO 00/37504; U.S. Pat. No. 6,207,156; Hurwitz et al. (1998) *Proc. Natl. Acad. Sci. USA* 95(17):10067-10071; Camacho et al. (2004) *J. Clin. Oncology* 22(145): Abstract No. 2505 (antibody CP-675206); and Mokyr et al. (1998) *Cancer Res.* 58:5301-5304. In certain embodiments, the anti-CTLA-4 antibody binds to human CTLA-4 with a $K_D$ of $5\times10^{-8}$ M or less, binds to human CTLA-4 with a $K_D$ of $1\times10^{-8}$ M or less, binds to human CTLA-4 with a $K_D$ of $5\times10^{-9}$ M or less, or binds to human CTLA-4 with a $K_D$ of between $1\times10^{-8}$ M and $1\times10^{10}$ M or less.

In another embodiment, the present invention provides a method for treating a hyperproliferative disease (e.g., cancer), comprising administering a LAG-3 antibody and a PD-1 antibody to a subject. In further embodiments, the anti-LAG-3 antibody is administered at a subtherapeutic dose, the anti-PD-1 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering an anti-LAG-3 antibody and a subtherapeutic dose of anti-PD-1 antibody to a subject. In certain embodiments, the subject is human. In certain embodiments, the anti-PD-1 antibody is a human sequence monoclonal antibody and the anti-LAG-3 antibody is human sequence monoclonal antibody, such as LAG3.5 described herein. Examples of human sequence anti-PD-1 antibodies include 17D8, 2D3, 4H1, 5C4 and 4A11, which are described in PCT Publication WO 06/121168. Other anti-PD-1 antibodies include, e.g., lambrolizumab (WO2008/156712), and AMP514 (WO2010/027423, WO2010/027827, WO2010/027828, WO2010/098788). In certain embodiments, the anti-PD-1 antibody binds to human PD-1 with a $K_D$ of $5\times10^{-8}$ M or less, binds to human PD-1 with a $K_D$ of $1\times10^{-8}$ M or less, binds to human PD-1 with a $K_D$ of $5\times10^{-9}$ M or less, or binds to human PD-1 with a $K_D$ of between $1\times10^{-8}$ M and $1\times10^{10}$ M or less.

In another embodiment, the present invention provides a method for treating a hyperproliferative disease (e.g., cancer), comprising administering a LAG-3 antibody and a PD-L1 antibody to a subject. In further embodiments, the anti-LAG-3 antibody is administered at a subtherapeutic dose, the anti-PD-L1 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering an anti-LAG-3 antibody and a subtherapeutic dose of anti-PD-L1 antibody to a subject. In certain embodiments, the subject is human. In other embodiments, the anti-PD-L1 antibody is a human sequence monoclonal antibody and the anti-LAG-3 antibody is human sequence monoclonal antibody, such as LAG3.5 described herein. Examples of human sequence anti-PD-L1 antibodies include 3G10, 12A4, 10A5, 5F8, 10H10, 1B12, 7H1, 11E6, 12B7 and 13G4, which are described in PCT Publication WO 07/005874. Other anti-PD-L1 antibodies include, e.g., MPDL3280A (RG7446) (WO2010/077634), MEDI4736 (WO2011/066389), and MDX1105 (WO2007/005874). In certain embodiments, the anti-PD-L1 antibody binds to human PD-L1 with a $K_D$ of $5\times10^{-8}$ M or less, binds to human PD-L1 with a $K_D$ of $1\times10^{-8}$ M or less, binds to human PD-L1 with a $K_D$ of $5\times10^{-9}$ M or less, or binds to human PD-L1 with a $K_D$ of between $1\times10^{-8}$ M and $1\times10^{10}$ M or less.

Blockade of LAG-3 and one or more second target antigens such as CTLA-4 and/or PD-1 and/or PD-L1 by antibodies can enhance the immune response to cancerous cells in the patient. Cancers whose growth may be inhibited using the antibodies of the instant disclosure include cancers typically responsive to immunotherapy. Representative examples of cancers for treatment with the combination therapy of the instant disclosure include those cancers specifically listed above in the discussion of monotherapy with anti-LAG-3 antibodies.

In certain embodiments, the combination of therapeutic antibodies discussed herein can be administered concurrently as a single composition in a pharmaceutically acceptable carrier, or concurrently as separate compositions with each antibody in a pharmaceutically acceptable carrier. In another embodiment, the combination of therapeutic antibodies can be administered sequentially. For example, an anti-CTLA-4 antibody and an anti-LAG-3 antibody can be administered sequentially, such as anti-CTLA-4 antibody being administered first and anti-LAG-3 antibody second, or anti-LAG-3 antibody being administered first and anti-CTLA-4 antibody second. Additionally or alternatively, an anti-PD-1 antibody and an anti-LAG-3 antibody can be administered sequentially, such as anti-PD-1 antibody being administered first and anti-LAG-3 antibody second, or anti-LAG-3 antibody being administered first and anti-PD-1 antibody second. Additionally or alternatively, an anti-PD-L1 antibody and an anti-LAG-3 antibody can be administered sequentially, such as anti-PD-L1 antibody being administered first and anti-LAG-3 antibody second, or anti-LAG-3 antibody being administered first and anti-PD-L1 antibody second.

Furthermore, if more than one dose of the combination therapy is administered sequentially, the order of the sequential administration can be reversed or kept in the same order at each time point of administration, sequential administrations can be combined with concurrent administrations, or any combination thereof. For example, the first administration of a combination anti-CTLA-4 antibody and anti-LAG-3 antibody can be concurrent, the second administration can be sequential with anti-CTLA-4 first and anti-LAG-3 second, and the third administration can be sequential with anti-LAG-3 first and anti-CTLA-4 second, etc. Additionally or alternatively, the first administration of a combination anti-PD-1 antibody and anti-LAG-3 antibody can be concurrent, the second administration can be sequential with anti-PD-1 first and anti-LAG-3 second, and the third administration can be sequential with anti-LAG-3 first and anti-PD-1 second, etc. Additionally or alternatively, the first administration of a combination anti-PD-L1 antibody and anti-LAG-3 antibody can be concurrent, the second administration can be sequential with anti-PD-L1 first and anti-LAG-3 second, and the third administration can be sequential with anti-LAG-3 first and anti-PD-L1 second, etc. Another representative dosing scheme can involve a first administration that is sequential with anti-LAG-3 first and anti-CTLA-4 (and/or anti-PD-1 and/or anti-PD-L1) second, and subsequent administrations may be concurrent.

Optionally, the combination of anti-LAG-3 and one or more additional antibodies (e.g., anti-CTLA-4 and/or anti-PD-1 and/or anti-PD-L1 antibodies) can be further combined with an immunogenic agent, such as cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below). A combined LAG-3 and CTLA-4 and/or PD-1 and/or PD-L1 blockade can be further combined with a vaccination protocol, such as any of the vaccination protocols discussed in detail above with respect to monotherapy with anti-LAG-3 antibodies.

A combined LAG-3 and CTLA-4 and/or PD-1 and/or PD-L1 blockade can also be further combined with standard cancer treatments. For example, a combined LAG-3 and CTLA-4 and/or PD-1 and/or PD-L1 blockade can be effectively combined with chemotherapeutic regimes. In these instances, it is possible to reduce the dose of other chemotherapeutic reagent administered with the combination of the instant disclosure (Mokyr et al. (1998) *Cancer Research* 58: 5301-5304). An example of such a combination is a combination of anti-LAG-3 and anti-CTLA-4 antibodies and/or anti-PD-1 antibodies and/or anti-PD-L1 antibodies further in combination with decarbazine for the treatment of melanoma. Another example is a combination of anti-LAG-3 and anti-CTLA-4 antibodies and/or anti-PD-1 antibodies and/or anti-PD-L1 antibodies further in combination with interleukin-2 (IL-2) for the treatment of melanoma. The scientific rationale behind the combined use of LAG-3 and CTLA-4 and/or PD-1 and/or PD-L1 blockade with chemotherapy is that cell death, which is a consequence of the cytotoxic action of most chemotherapeutic compounds, should result in increased levels of tumor antigen in the antigen presentation pathway. Other combination therapies that may result in synergy with a combined LAG-3 and CTLA-4 and/or PD-1 and/or PD-L1 blockade through cell death include radiation, surgery, or hormone deprivation. Each of these protocols creates a source of tumor antigen in the host. Angiogenesis inhibitors can also be combined with a combined LAG-3 and CTLA-4 and/or PD-1 and/or PD-L1 blockade. Inhibition of angiogenesis leads to tumor cell death, which can be a source of tumor antigen fed into host antigen presentation pathways.

A combination of LAG-3 and CTLA-4 and/or PD-1 and/or PD-L1 blocking antibodies can also be used in combination with bispecific antibodies that target Fcα or Fcγ receptor-expressing effector cells to tumor cells (see, e.g., U.S. Pat. Nos. 5,922,845 and 5,837,243). Bispecific antibodies can be used to target two separate antigens. The T cell arm of these responses would be augmented by the use of a combined LAG-3 and CTLA-4 and/or PD-1 and/or PD-L1 blockade.

In another example, a combination of anti-LAG-3 and anti-CTLA-4 and/or anti-PD-1 antibodies and/or anti-PD-L1 antibodies can be used in conjunction with anti-neoplastic antibodies, such as Rituxan® (rituximab), Herceptin® (trastuzumab), Bexxar® (tositumomab), Zevalin® (ibritumomab), Campath® (alemtuzumab), Lymphocide® (eprtuzumab), Avastin® (bevacizumab), and Tarceva® (erlotinib), and the like. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4, PD-1, PD-L1 or LAG-3. In an exemplary embodiment, a treatment of a hyperproliferative disease (e.g., a cancer tumor) can include an anti-cancer antibody in combination with anti-LAG-3 and anti-CTLA-4 and/or anti-PD-1 and/or anti-PD-L1 antibodies, concurrently or sequentially or any combination thereof, which can potentiate an anti-tumor immune responses by the host.

Tumors evade host immune surveillance by a large variety of mechanisms. Many of these mechanisms may be overcome by the inactivation of proteins, which are expressed by the tumors and which are immunosuppressive. These include, among others, TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). In another example, antibodies to each of these entities can be further combined with an anti-LAG-3 and anti-CTLA-4 and/or anti-PD-1 and/or anti-PD-L1 antibody combination to counteract the effects of immunosuppressive agents and favor anti-tumor immune responses by the host.

Other antibodies that can be used to activate host immune responsiveness can be further used in combination with an anti-LAG-3 and anti-CTLA-4 and/or anti-PD-1 and/or anti-PD-L1 antibody combination. These include molecules on the surface of dendritic cells that activate DC function and antigen presentation. Anti-CD40 antibodies (Ridge et al., supra) can be used in conjunction with an anti-LAG-3 and anti-CTLA-4 and/or anti-PD-1 and/or anti-PD-L1 combination (Ito et al., supra). Other activating antibodies to T cell costimulatory molecules Weinberg et al., supra, Melero et al. supra, Hutloff et al., supra) may also provide for increased levels of T cell activation.

As discussed above, bone marrow transplantation is currently being used to treat a variety of tumors of hematopoietic origin. A combined LAG-3 and CTLA-4 and/or PD-1 and/or PD-L1 blockade can be used to increase the effectiveness of the donor engrafted tumor specific T cells.

Several experimental treatment protocols involve ex vivo activation and expansion of antigen specific T cells and adoptive transfer of these cells into recipients in order to antigen-specific T cells against tumor (Greenberg & Riddell, supra). These methods can also be used to activate T cell responses to infectious agents such as CMV. Ex vivo activation in the presence of anti-LAG-3 and anti-CTLA-4 and/or anti-PD-1 and/or anti-PD-L1 antibodies can be expected to increase the frequency and activity of the adoptively transferred T cells.

In certain embodiments, the present invention provides a method for altering an adverse event associated with treatment of a hyperproliferative disease (e.g., cancer) with an immunostimulatory agent, comprising administering an anti-LAG-3 antibody and a subtherapeutic dose of anti- CTLA-4 and/or anti-PD-1 and/or anti-PD-L1 antibody to a subject. For example, the methods of the present invention provide for a method of reducing the incidence of immunostimulatory therapeutic antibody-induced colitis or diarrhea by administering a non-absorbable steroid to the patient. Because any patient who will receive an immunostimulatory therapeutic antibody is at risk for developing colitis or diarrhea induced by such an antibody, this entire patient population is suitable for therapy according to the methods of the present invention. Although steroids have been administered to treat inflammatory bowel disease (IBD) and prevent exacerbations of IBD, they have not been used to prevent (decrease the incidence of) IBD in patients who have not been diagnosed with IBD. The significant side effects associated with steroids, even non-absorbable steroids, have discouraged prophylactic use.

In further embodiments, a combination LAG-3 and CTLA-4 and/or PD-1 and/or PD-L1 blockade (i.e., immunostimulatory therapeutic antibodies anti-LAG-3 and anti-CTLA-4 and/or anti-PD-1 antibodies and/or anti-PD-L1 antibodies) can be further combined with the use of any non-absorbable steroid. As used herein, a "non-absorbable steroid" is a glucocorticoid that exhibits extensive first pass metabolism such that, following metabolism in the liver, the bioavailability of the steroid is low, i.e., less than about 20%. In one embodiment of the invention, the non-absorbable steroid is budesonide. Budesonide is a locally-acting glucocorticosteroid, which is extensively metabolized, primarily by the liver, following oral administration. ENTOCORT EC.® (Astra-Zeneca) is a pH- and time-dependent oral formulation of budesonide developed to optimize drug delivery to the ileum and throughout the colon. ENTOCORT EC.® is approved in the U.S. for the treatment of mild to moderate Crohn's disease involving the ileum and/or ascending colon. The usual oral dosage of ENTOCORT EC.® for the treatment of Crohn's disease is 6 to 9 mg/day. ENTOCORT EC is released in the intestines before being absorbed and retained in the gut mucosa. Once it passes through the gut mucosa target tissue, ENTOCORT EC.® is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT EC.® can result in systemic glucocorticoid effects such as hypercorticism and adrenal suppression. See PDR 58$^{th}$ ed. 2004; 608-610.

In still further embodiments, a combination LAG-3 and CTLA-4 and/or PD-1 and/or PD-L1 blockade (i.e., immunostimulatory therapeutic antibodies anti-LAG-3 and anti-CTLA-4 and/or anti-PD-1 antibodies and/or anti-PD-L1 antibodies) in conjunction with a non-absorbable steroid can be further combined with a salicylate. Salicylates include 5-ASA agents such as, for example: sulfasalazine (AZUILFIDINE®, Pharmacia & UpJohn); olsalazine (DIPENTUM®, Pharmacia & UpJohn); balsalazide (COLAZAL®, Salix Pharmaceuticals, Inc.); and mesalamine (ASACOL®, Procter & Gamble Pharmaceuticals; PENTASA®, Shire US; CANASA®, Axcan Scandipharm, Inc.; ROWASA®, Solvay).

In accordance with the methods of the present invention, a salicylate administered in combination with anti-LAG-3 and anti-CTLA-4 and/or anti-PD-1 and/or anti-PD-L1 antibodies and a non-absorbable steroid can includes any overlapping or sequential administration of the salicylate and the non-absorbable steroid for the purpose of decreasing the incidence of colitis induced by the immunostimulatory antibodies. Thus, for example, methods for reducing the incidence of colitis induced by the immunostimulatory antibodies according to the present invention encompass administering a salicylate and a non-absorbable concurrently or sequentially (e.g., a salicylate is administered 6 hours after a non-absorbable steroid), or any combination thereof. Further, according to the present invention, a salicylate and a non-absorbable steroid can be administered by the same route (e.g., both are administered orally) or by different routes (e.g., a salicylate is administered orally and a non-absorbable steroid is administered rectally), which may differ from the route(s) used to administer the anti-LAG-3 and anti-CTLA-4 and/or anti-PD-1 and/or anti-PD-L1 antibodies.

The present disclosure is further illustrated by the following examples, which should not be construed as further limiting. The contents of all figures and all references, Genbank sequences, patents and published patent applications cited throughout this application are expressly incorporated herein by reference. In particular, the disclosures of PCT publications WO 09/045957, WO 09/073533, WO 09/073546, and WO 09/054863 are expressly incorporated herein by reference.

EXAMPLES

Example 1: Design of Variants of LAG3.1 (Antibody 25F7)

Antibody variants of the previously described anti-LAG-3 antibody, 25F7, referred to herein as LAG3.1, were created by first analyzing the amino acid sequence of the antibody for potential sites of degradation. Expression of site-directed mutagenesis of LAG3.1 $V_H$ region was performed using QuikChange II XL® Site-Directed Mutagenesis Kit (Agilent Technologies). The altered $V_H$ regions were then subcloned into UCOE® (EMD Millipore) vectors that contain the human IgG4-S228P constant region. The various heavy chain vectors were each co-transfected with a vector expressing the LAG3.1 kappa chain into CHO-S cells, and stable pools were selected for expression.

Five potential deamidation motifs were identified within the variable region heavy chain CDR2. These sites were located at positions 52, 54, 56, 58, and 60 of the heavy chain variable region of LAG3.1 (SEQ ID NO: 2) (see FIG. 1A). In particular, deamidation of the "NG" sequence within the VH CDR2 (SEQ ID NO: 6) was observed under all conditions, as well as further isomerization of the sequence. Deamidation of the starting material was about 10%. Further, it was found that this "NG" sequence did not correspond to a germline sequence (see FIG. 3). However, the consensus germline sequence was a potential glycosylation site and, therefore, was not included among the antibody variants.

Four variants (referred to herein as LAG3.5, LAG3.6, LAG3.7, and LAG3.8) were designed which addressed two of the potential deamidation motifs (positions 54 and 56), as shown in FIG. 3. These variants were subjected to a matrix of conditions as summarized in Table 1 below and the following characteristics were analyzed: (a) chemical and thermal stabilities (physical stability); (b) size exclusion chromatography (aggregation); (c) Isoelectric Focusing gel (IEF) (charge heterogeneity); (d) activity by Biacore analysis (binding and functional activity); and (e) peptide mapping by mass-spectrometry (chemical modifications/molecular stability).

TABLE 1

| Buffer | Acetate (100 nM NaCl, 3% w/v mannitol, 0.03% Tween-20) | Citrate (100 nM NaCl, 3% w/v mannitol, 0.03% Tween-20) |
|---|---|---|
| pH | 5.5, 6.0, 6.5, 7.0 | 5.5, 6.0, 6.5, 7.0 |
| Temperature | 4° C. and 37° C. | 4° C. and 37° C. |
| Time | 0, 4, 8, 12 weeks | 0, 4, 8, 12 weeks |

Example 2: Characterization of LAG-3 Variants

1. Activated Human CD4+ T Cell Binding

To test the ability of the antibody variants to bind to native human LAG-3 on the surface of activated human T cells, normal healthy donor peripheral blood mononuclear cells were stimulated in 15 cm tissue culture plates at a density of 2×10e6 cells/mL, with a combination of anti-CD3 (eBioscience, Cat #16-0037-85) and anti-CD28 (BD Bioscience, Cat #555725) antibodies present in solution at 5 µg/mL and 3 µg/mL, respectively. Following three days of stimulation cells were harvested, washed 1× with 1×PFAE buffer (1×PBS+2% FBS, 0.02% sodium azide, 2 mM Na EDTA), and resuspended in 1×PFAE buffer for staining.

For the binding reaction, the LAG3.1 variants were serially diluted with cold 1×PFAE buffer, then 50 µl of diluted antibody solution was mixed with 50 µl of Fitc-labeled anti-human CD4 (BD Bioscience, Cat #555346) diluted 1:16 in 1×PFAE buffer. For the binding reaction, 100 µl of this diluted antibody mixture was added to $2\times10^5$ cells and the mixture was incubated on at 4° C. for 30 minutes. The cells were then washed two times with 1×PFAE buffer. A 1:200 dilution of PE-labeled goat anti-human Fcγ-specific antibody (Jackson ImmunoResearch, Cat. #109-116-170) was added and the mixture was incubated for 30 minutes at 4° C., followed by washing twice with cold 1×PFAE buffer. After the final wash, 150 µl of cold 1×PFAE was added to each solution and analysis of antibody binding was carried out by flow cytometry using a FACSCanto flow cytometer (BD Bioscience).

The results of the flow cytometry analysis are summarized in FIG. 4A which is a graph showing the $EC_{50}$ for antibody binding to activated human CD4+ T cells. FIG. 4B is a graph showing antibody binding to soluble human LAG-3/Fc antigen by BIACORE. As shown, the binding affinities of LAG3.5 and LAG3.8 are slightly lower, compared to LAG3.1, while their off-rate constants are slightly higher compared to LAG3.1.

2. Physical Stability

Thermal stability and thermal denaturation of the variants was tested using Microcal VP-DSC. Specifically, each variant was diluted into PBS (Mediatech cat #21-040-CV lot #21040139). The final concentration of sample was 250 µg/mL after dilution into PBS. The sample was scanned to 74° C., cooled to 25° C., and reheated to 74° C. PBS buffer was used as a blank control. Data was fit to a Non-2-state model and curve fitting performed by Origin software.

As summarized in Table 2 and shown in FIG. 5, LAG3.5 had a higher melting temperature TM2 than LAG3.1, indicating greater overall stability.

TABLE 2

| MAb | Tm1 (° C.) Corresponds to CH2 and/or Fab domains | Tm2 (° C.) Corresponds to CH3 and/or Fab domains |
|---|---|---|
| LAG3.1 | 70.7 | 75.7 |
| LAG3.5 | 70.5 | 76.3 |
| LAG3.6 | 67.8 | 70.8 |
| LAG3.7 | 69.4 | 73.5 |
| LAG3.8 | 70.3 | 75.4 |

Antibody refolding following denaturation is an inverse measure of long-term aggregation potential. Accordingly, the LAG-3 variants also were tested and compared in terms of thermal reversability. Specifically, the antibodies were heated to 74° C. and cooled to room temperature before heated back to 74° C. The ratio of area under the curve of the second to first thermograms provides the estimate of thermal reversibility, which is a direct measure of conformational reversibility.

As summarized in Table 3 and shown in FIG. 6, LAG3.5 had substantially higher thermal reversibility than all other variants. Notably, the percent reversibility for LAG3.5 (47%) was more than double that of LAG3.1 (20%). The thermal reversibility is strongly correlated to the long-term aggregation potential. Lower reversibility corresponds to higher potential aggregation. Based on this observation, LAG3.1 would potentially exhibit substantially higher aggregation over time, compared to LAG3.5. Similarly, all other variants could potentially exhibit substantially higher aggregation over time compared to LAG3.5.

TABLE 3

| MAb | Thermal reversibility (%) |
|---|---|
| LAG3.1 | 20 |
| LAG3.5 | 47 |
| LAG3.6 | 0 |
| LAG3.7 | 11 |
| LAG3.8 | 26 |

3. Aggregation

The variants also were tested for stability as a measure of protein aggregation using standard Size Exclusion HPLC (SEC-HPLC) according the following protocol: antibody test samples were diluted to 1.0 mg/ml with phosphate buffered saline (PBS) and 10 uL was applied to an HPLC (Waters, model 2795). Separation was accomplished on a gel filtration column (TOSOH Bioscience, TSKgel G3000 SWxl, 7.8 mm×300 mm, product #08541) using a mobile phase of 0.1M sodium phosphate, 0.15M sodium chloride, 0.1M sodium sulfate, pH 7.2. The analyte was detected by monitoring UV absorbance at 280 nm, and the antibody peak area percent composition was determined using Empower software. As shown in Table 4, LAG3.5 exhibited substantially reduced aggregation compared to LAG3.1.

TABLE 4

| Sample | IgG Monomer (% peak area) | IgG Aggregate (% peak area) |
|---|---|---|
| LAG3.1 | 90 | 10 |
| LAG3.5 | 96 | 4 |
| LAG3.6 | 96 | 4 |
| LAG3.7 | 95 | 5 |
| LAG3.8 | 95 | 5 |

Example 3: Variant Selection

Based on the studies described above, antibody variant LAG3.5 was selected for further analysis, in view of its significantly improved physical and chemical stability compared to its unmodified form (LAG3.1), particularly its high capacity for conformational refolding (thermal reversibility). This analysis included a two-step approach of (a) accelerated stress, (b) followed by 12-week real-time stability evaluation. Specifically, LAG3.5 was incubated at 1.0 mg/ml in pH 8.0, 50 mM Ammonium Bicarbonate, for 5 days at 40 C.°. The degree of modifications after 5 days was analyzed, as well as the effects on activity and stability. The LAG3.5 variant was then subjected to real-time stability in PBS for a duration of 12 weeks and subsequently analyzed. The results of these studies are described below.

1. Antigen Binding

Figure 7:
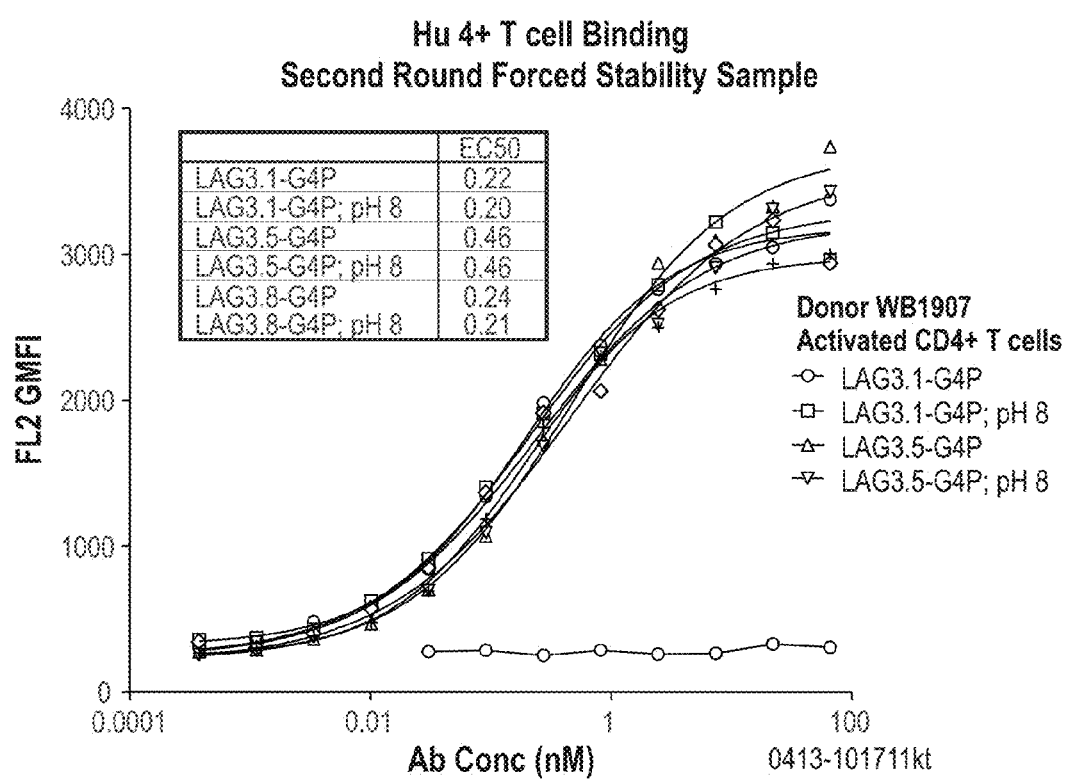
FIG. 7 is a graph, showing the binding activity of antibodies LAG3.1 (25F7) and LAG3.5 to activated human CD4+ T cells and antigen binding (Biacore).

As shown in FIG. 7 (and Table 5), no change in antigen binding was observed after 5 days. As also shown in FIGS. 10A and B, LAG3.5 exhibited no change in antigen binding or physical stability after 12 weeks. In particular, LAG3.5 maintains higher affinity than LAG3.8 over the entire 12 week period at both 4° C. and 40° C.

TABLE 5

| Clone ID | Antigen | $K_D \times 10^{-9}$ (M) | $k_{on} \times 10^4$ (1/Ms) | $K_{off} \times 10^{-4}$ (1/s) |
| --- | --- | --- | --- | --- |
| Lag3.1 | PBS | 0.21 | 166 | 3.44 |
|  | pH 8 | 0.20 | 184 | 3.61 |
| Lag3.5 | PBS | 0.25 | 130 | 3.22 |
|  | pH 8 | 0.20 | 148 | 2.98 |
| Lag3.8 | PBS | 0.25 | 147 | 3.68 |
|  | pH 8 | 0.25 | 162 | 4.02 |

2. Chemical Modifications/Molecular Stability

Peptide mapping by mass spectrometry was used to analyze the chemical/molecular stability of LAG3.5 compared to LAG3.1. Specifically, purified antibody was reduced, alkylated, dialyzed, and digested with trypsin (Promega Cat. V5111) and GluC (Roche Cat. 11047817001). Digests were analyzed by nano-LC MSMS mass spectrometry (Thermo Fisher LTQ Orbitrap).

As shown in FIG. 8, LAG3.1 showed increased heterogeneity in $V_H$ compared to LAG3.5 when subjected to accelerated stability at higher pH, which deamidates asparagine residues (step 1). Change in mass due to isomerization could not be detected under the current experimental conditions. The percentage change is expressed as a ratio of all changes combined to the parental peak.

Figure 11A:
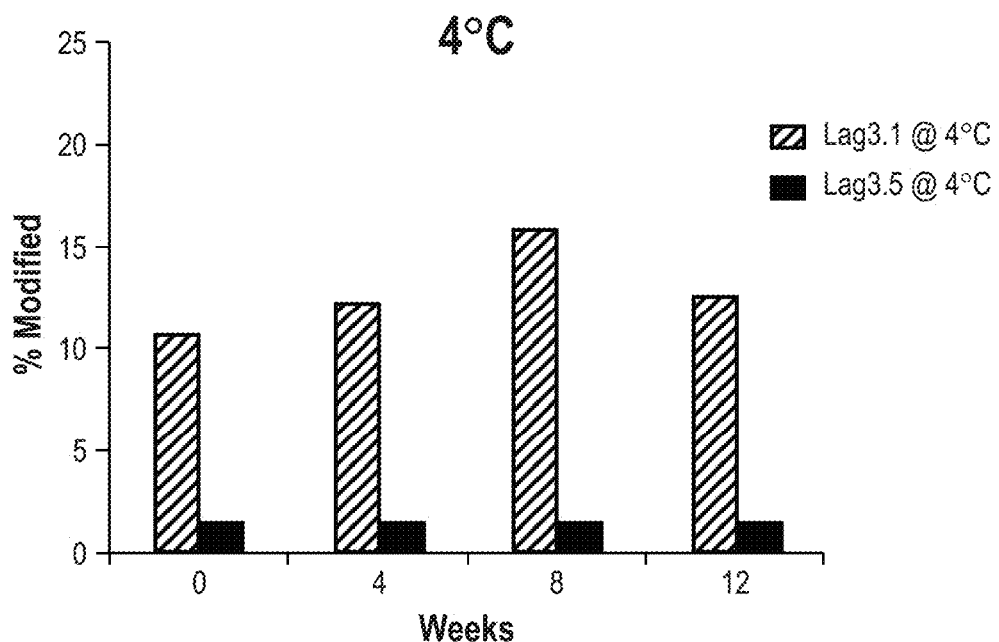
FIGS. 11 A and B are graphs comparing the percent modification of the amino acid sequences of antibodies LAG3.1 and LAG3.5 at 4 C.° and 40 C.°.
Figure 11B:
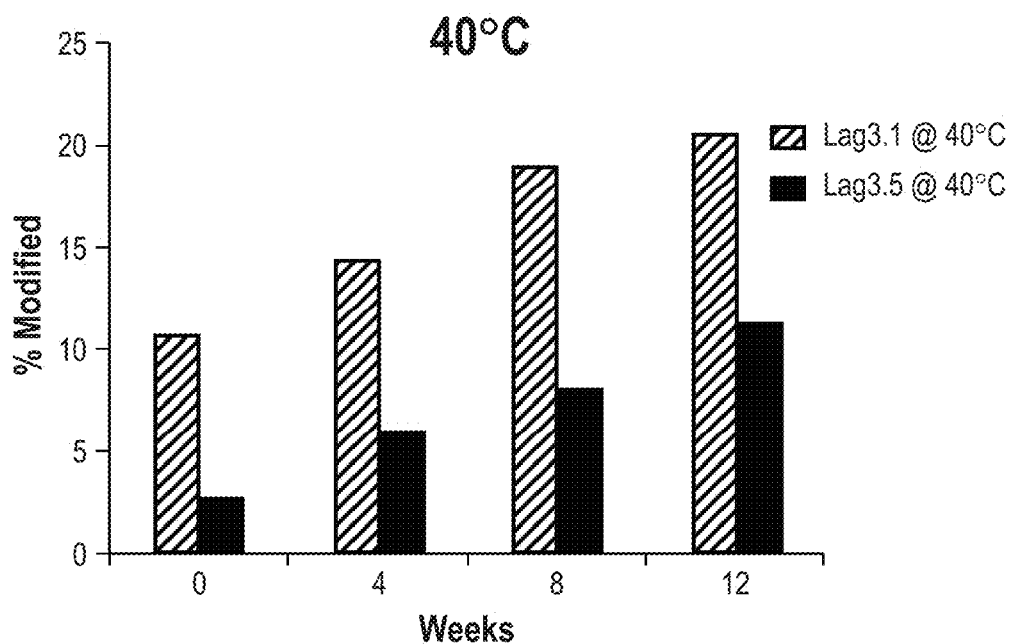

In addition, as shown in FIG. 11, LAG3.1 showed increased heterogeneity in $V_H$ compared to LAG3.5 when subjected to prolonged real-time stability of 12 weeks, at both 4° C. and 40° C. (step 2).

3. Physical Stability

Thermal reversibility was measured in PBS and at pH 8.0. Under both conditions, LAG3.5 again exhibited approximately double the level of refolding compared to LAG3.1. Specifically, as shown in Tables 6-8, LAG3.5 exhibited 43% refolding compared to 18% for LAG3.1 in PBS. LAG3.5 also exhibited 48% refolding compared to 29% refolding for LAG3.1 at pH 8.0.

TABLE 6

| DSC: melting | | | |
| --- | --- | --- | --- |
| MAb | Condition | Tm1 | Tm2 |
| Lag3.1 | PBS | 70.7 | 75.7 |
| Lag3.1 | pH 8 | 70.4 | 75.6 |
| Lag3.5 | PBS | 70.8 | 76.4 |
| Lag3.5 | pH 8 | 70.5 | 76.3 |

TABLE 7

| Fluorolog-2: unfolding | | |
| --- | --- | --- |
| Mab/mutants | Midpoint (M) | Aggregation (M) |
| Lag3.1 PBS | 1.99 | — |
| Lag3.1 pH 8 | 2.08 | — |
| Lag3.5 PBS | 1.86 | — |
| Lag3.5 pH 8 | 2.00 | — |

TABLE 8

| DSC: refolding | | |
| --- | --- | --- |
| MAb | % reversibility PBS | % reversibility pH 8 |
| Lag3.1 | 18 | 29 |
| Lag3.5 | 43 | 48 |

4. Charge Heterogeneity

To assess charge heterogeneity, the variants were analyzed using isoelectrofocusing (IEF) with standard markers of pI 5.5 and pI 10.0 compared to LAG3.1. Briefly, antibody solutions were applied onto a 1 mm thick IEF pI 3-7 pre-made gel (Invitrogen, Cat#EC6648BOX) along with a pI 3-10 markers (SERVA, Cat#39212). Electrophoresis was carried out using IEF 3-7 Cathode buffer (Invitrogen, Cat# LC5370) and IEF Anode buffer (Invitrogen, Cat#LC5300) and applying electrical current in the order of 100 V constant for 1 hr, 200 V constant for 1 hr, and 500 V constant for 30 min. The IEF gels were stained with Coomassie blue to detect the protein bands and destained with methanol-acetic acid solution. IEF gels were then analyzed by ImageQuant TL software. Based on this analysis (data not shown), LAG3.5 exhibited significantly less heterogeneity compared to LAG3.1.

5. HIC-HPLC

Figure 9:
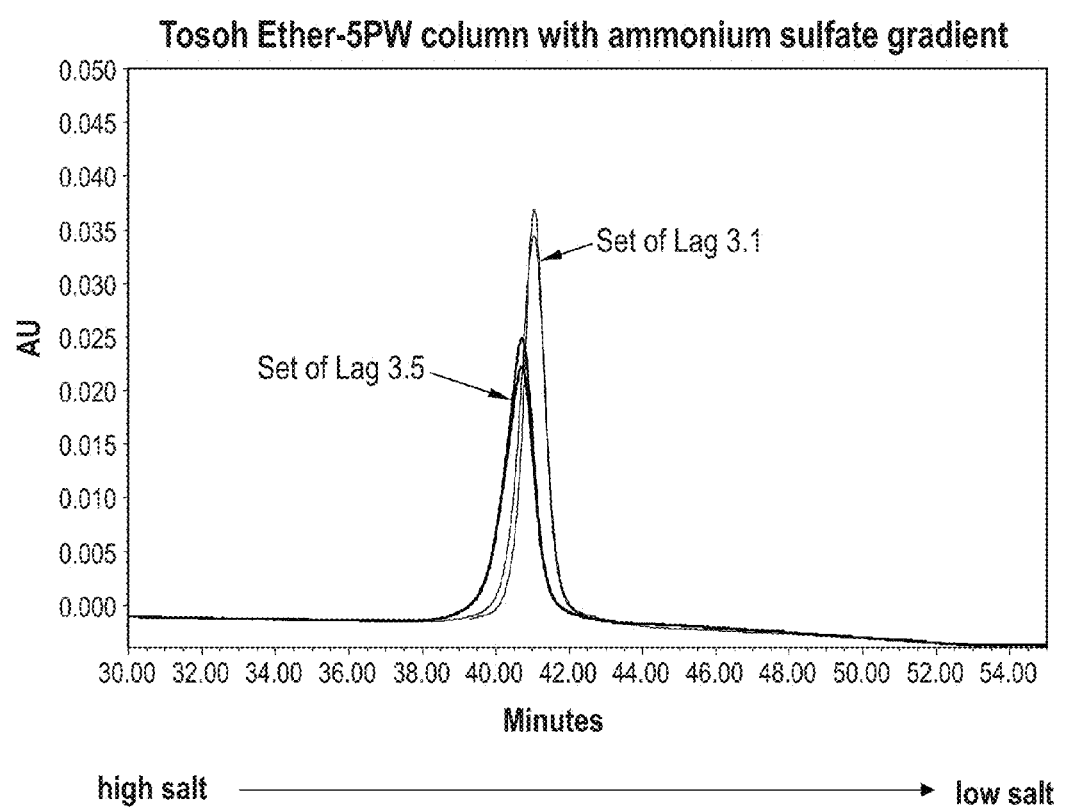
FIG. 9 is a graph comparing the hydrophilicity profiles of antibodies LAG3.1 (25F7) and LAG3.5.

To assess solubility, the variants were analyzed using standard Hydrophobic Interaction Chromatography (HIC-HPLC) according to the following protocol: 50 uL of 2M ammonium sulfate was added to 50 uL of antibody test sample at 1 mg/ml. 80 uL of the test sample was then applied to an HPLC (Waters, model 2795) connected in-line to an HIC column (TOSOH Bioscience, Ether-5PW TSK-gel, 7.5 mm×75 mm, product #07573). The sample was eluted at a flow rate of 1.0 ml/min with a gradient of 100% buffer A (2M ammonium sulfate, 0.1M sodium phosphate, pH 7.0) to 100% buffer B (0.1M sodium phosphate, pH 7.0) over 50 minutes. The antibody was detected by monitoring UV absorbance at 280 nm and data was analyzed using Empower software. As shown in FIG. 9, the hydrophilicity of LAG3.5 exhibited solubility at high concentrations of ammonium sulfate.

Example 4: Reversal of T-Cell Mediated Immune Response Inhibition

The activity of LAG3.5 was determined by means of a functional assay that utilized an antigen-specific mouse T cell hybridoma (3A9). Hybridoma 3A9 expresses a T cell receptor specific for a peptide from hen egg lysozyme (HEL48-62) and secretes IL-2 when co-cultured with peptide-pulsed, MHC-matched, antigen presenting cells (LK35.2). Since huLAG-3-Fc is capable of binding to MHC Class II-positive mouse B cell lines, expression of huLAG-3 in the 3A9 line could exert an inhibitory effect through engagement with Class II on the murine presenting line. A comparison of the peptide response profile of the 3A9 parent with that of the human LAG-3-transduced 3A9 cells co-cultured with MHC-matched antigen presenting cells demonstrated that the expression of human LAG-3 inhibited peptide responsiveness compared to control 3A9 cells. This inhibition was reversed by LAG-3 blockade using LAG3.5. Therefore, blockade of LAG-3-mediated inhibition was demonstrated for LAG3.5.

Example 5: T-Cell Activation by LAG3.5

The functional activity of LAG3.5 on primary T cells was assessed using human PBMC cultures stimulated by the superantigen SEB. Total PBMC were isolated from the blood of eighteen human donors and stimulated for 72 hours in either of two assay formats: (i) a fixed amount of antibody (20 m/mL) and serial dilutions of SEB, or (ii) a fixed amount of SEB (85 ng/mL) and serial dilutions of antibody. Secreted IL-2, as a measure of T cell activity, was monitored by ELISA. Antibody anti-PD-1 antibody and Ipilimumab were used as positive controls and the activity of LAG3.5 in combination with anti-PD-1 or anti-CTLA-4 was also evaluated for a subset of donors.

Enhanced IL-2 secretion was observed over a range of SEB concentrations from fifteen of the eighteen donors treated with LAG3.5 alone, compared to isotype control antibody treatment. In most instances the stimulation was less than that observed for treatment with anti-PD-1 or Ipilimumab. With respect to LAG3.5, the results of the two assay formats (described above) were in agreement with one another. Moreover, in 5 of 6 donors tested, combining LAG3.5 with anti-PD-1 or Ipilimumab resulted in higher levels of stimulation than observed for isotype control antibody combined with anti-PD-1 or Ipilimumab. These data revealed that LAG3.5 can function in normal human T cell assays and can further activate responses mediated by inhibition of PD-1 and CTLA-4 function.

SUMMARY OF SEQUENCE LISTING

| SEQ ID NO: | DESCRIPTION | SEQUENCE |
|---|---|---|
| 1 | $V_H$ n.a. 25F7 (LAG3.1) | |

>1408_LAG-3_403_25F7.1_VH1_NT
CAGGTGCAGCTACAGCAGTGGGGCGCAGGACTGTTGAAGCCTTCGGAGAC
CCTGTCCCTCACCTGCGCTGTCTATGGTGGGTCCTTCAGTGATTACTACT
GGAACTGGATCCGCCAGCCCCCAGGGAAGGGGCTGGAGTGGATTGGGGAA
ATCAATCATAATGGAAACACCAACTCCAACCCGTCCCTCAAGAGTCGAGT
CACCCTATCACTAGACACGTCCAAGAACCAGTTCTCCCTGAAGCTGAGGT
CTGTGACCGCCGCGGACACGGCTGTGTATTACTGTGCGTTTGGATATAGT
GACTACGAGTACAACTGGTTCGACCCCTGGGGCCAGGGAACCCTGGTCAC
CGTCTCCTCA

| 2 | $V_H$ a.a. 25F7 | |

>1408_LAG-3_403_25F7.1_VH1_AA
QVQLQQWGAGLLKPSETLSLTCAVYGGSFSDYYWNWIRQPPGKGLEWIGE
INHNGNTNSNPSLKSRVTLSLDTSKNQFSLKLRSVTAADTAVYYCAFGYS
DYEYNWFDPWGQGTLVTVSS

SUMMARY OF SEQUENCE LISTING

| SEQ ID NO: | DESCRIPTION | SEQUENCE |
|---|---|---|
| 3 | $V_K$ n.a. 25F7 | |

>1408_LAG-3_403_25F7.1_VK1_NT
GAAATTGTGTTGACACAGTCTCCAGCCACCCTGTCTTTGTCTCCAGGGGA
AAGAGCCACCCTCTCCTGCAGGGCCAGTCAGAGTATTAGCAGCTACTTAG
CCTGGTACCAACAGAAACCTGGCCAGGCTCCCAGGCTCCTCATCTATGAT
GCATCCAACAGGGCCACTGGCATCCCAGCCAGGTTCAGTGGCAGTGGGTC
TGGGACAGACTTCACTCTCACCATCAGCAGCCTAGAGCCTGAAGATTTTG
CAGTTTATTACTGTCAGCAGCGTAGCAACTGGCCTCTCACTTTTGGCCAG
GGGACCAACCTGGAGATCAAA

| 4 | $V_K$ a.a. 25F7 | |

>1408_LAG-3_403_25F7.1_VK1_AA
EIVLTQSPATLSLSPGERATLSCRASQSISSYLAWYQQKPGQAPRLLIYD
ASNRATGIPARFSGSGSGTDFTLTISSLEPEDFAVYYCQQRSNWPLTFGQ
GTNLEIK

| 5 | $V_H$ CDR1 a.a. 25F7 | DYYWN |
| 6 | $V_H$ CDR2 a.a. 25F7 | EINHNGNTNSNPSLKS |
| 7 | $V_H$ CDR3 a.a. 25F7 | GYSDYEYNWFDP |
| 8 | $V_K$ CDR1 a.a. 25F7 | RASQSISSYLA |
| 9 | $V_K$ CDR2 a.a. 25F7 | DASNRAT |
| 10 | $V_K$ CDR3 a.a. 25F7 | QQRSNWPLT |
| 11 | $V_H$ n.a. LAG3.5 | |

$V_H$ n.a. LAG3.5
caggtgcagctacagcagtggggcgcaggactgttgaagccttcggagac
cctgtccctcacctgcgctgtctatggtgggtccttcagtgattactact
ggaactggatccgccagccccagggaaggggctggagtggattgggaa
atcaatcatcgtggaagcaccaactccaacccgtccctcaagagtcgagt
caccctatcactagacacgtccaagaaccagttctccctgaagctgaggt
ctgtgaccgccgcggacacggctgtgtattactgtgcgtttggatatagt
gactacgagtacaactggttcgacccctggggccagggaaccctggtcac
cgtctcctca

| 12 | $V_H$ a.a. LAG3.5 | |

$V_H$ a. a. LAG3.5
QVQLQQWGAGLLKPSETLSLTCAVYGGSFSDYYWNWIRQPPGKGLEWIGE
INHRGSTNSNPSLKSRVTLSLDTSKNQFSLKLRSVTAADTAVYYCAFGYS
DYEYNWFDPWGQGTLVTVSS

| 13 | $V_K$ n.a. LAG3.5 | |

$V_K$ n.a. LAG3.5
gaaattgtgttgacacagtctccagccaccctgtattgtctccaggggaa
agagccaccctctcctgcagggccagtcagagtattagcagctacttagc
ctggtaccaacagaaacctggccaggctcccaggctcctcatctatgatg
catccaacagggccactggcatcccagccaggttcagtggcagtgggtct
gggacagacttcactctcaccatcagcagcctagagcctgaagattttgc
agtttattactgtcagcagcgtagcaactggcctctcacttttggccagg
ggaccaacctggagatcaaa

| 14 | $V_K$ a.a. LAG3.5 | |

$V_K$ a.a. LAG3.5
EIVLTQSPATLSLSPGERATLSCRASQSISSYLAWYQQKPGQAPRLLIYD
ASNRATGIPARFSGSGSGTDFTLTISSLEPEDFAVYYCQQRSNWPLTFGQ
GTNLEIK

| 15 | $V_H$ CDR1 a.a. LAG3.5 | DYYWN |
| 16 | $V_H$ CDR2 a.a. LAG3.5 | EINHRGSTNSNPSLKS |
| 17 | $V_H$ CDR3 a.a. LAG3.5 | GYSDYEYNWFDP |
| 18 | $V_K$ CDR1 a.a. LAG3.5 | RASQSISSYLA |
| 19 | $V_K$ CDR2 a.a. LAG3.5 | DASNRAT |
| 20 | $V_K$ CDR3 a.a. LAG3.5 | QQRSNWPLT |

SUMMARY OF SEQUENCE LISTING

| SEQ ID NO: | DESCRIPTION | SEQUENCE |
|---|---|---|
| 21 | LAG-3 epitope | PGHPLAPG |
| 22 | LAG-3 epitope | HPAAPSSW |
| 23 | LAG-3 epitope | PAAPSSWG |
| 24 | V_H CDR2 a.a. LAG3.6 | EIIHSGSTNSNPSLKS |
| 25 | V_H CDR2 a.a. LAG3.7 | EINHGGGTNSNPSLKS |
| 26 | V_H CDR2 a.a. LAG3.8 | EINHIGNTNSNPSLKS |
| 27 | V_H CDR2 a.a. HUMAN GERMLINE | GEINHSGSTNY |
| 28 | | (Gly_4-Ser)_3 |
| 29 | Human LAG-3 a.a. | | human LAG-3 a.a. sequence
MWEAQFLGLLFLQPLWVAPVKPLQPGAEVPVVWAQEGAPAQLPCSPTIPL
QDLSLLRRAGVTWQHQPDSGPPAAAPGHPLAPGPHPAAPSSWGPRPRRYT
VLSVGPGGLRSGRLPLQPRVQLDERGRQRGDFSLWLRPARRADAGEYRAA
VHLRDRALSCRLRLRLGQASMTASPPGSLRASDWVILNCSFSRPDRPASV
HWFRNRGQGRVPVRESPHHHLAESFLFLPQVSPMDSGPWGCILTYRDGFN
VSIMYNLTVLGLEPPTPLTVYAGAGSRVGLPCRLPAGVGTRSFLTAKWTP
PGGGPDLLVTGDNGDFTLRLEDVSQAQAGTYTCHIHLQEQQLNATVTLAI
ITVTPKSFGSPGSLGKLLCEVTPVSGQERFVWSSLDTPSQRSFSGPWLEA
QEAQLLSQPWQCQLYQGERLLGAAVYFTELSSPGAQRSGRAPGALPAGHL
LLFLTLGVLSLLLLVTGAFGFHLWRRQWRPRRFSALEQGIHPPQAQSKIE
ELEQEPEPEPEPEPEPEPEPEPEQL*

| 30 | V_H CDR2 a.a. LAG3.2 | VIWYDGSNKYYADSVKG |
| 31 | V_H LAG3.1 n.a. | |

LAG3.1HC
CAGGTGCAGCTACAGCAGTGGGGCGCAGGACTGTTGAAGCCTTCGGAGAC
CCTGTCCCTCACCTGCGCTGTCTATGGTGGGTCCTTCAGTGATTACTACT
GGAACTGGATCCGCCAGCCCCCAGGGAAGGGGCTGGAGTGGATTGGGGAA
ATCAATCATAATGGAAACACCAACTCCAACCCGTCCCTCAAGAGTCGAGT
CACCCTATCACTAGACACGTCCAAGAACCAGTTCTCCCTGAAGCTGAGGT
CTGTGACCGCCGCGGACACGGCTGTGTATTACTGTGCGTTTGGATATAGT
GACTACGAGTACAACTGGTTCGACCCCTGGGGCCAGGGAACCCTGGTCAC
CGTCTCCTCAGCTAGCACCAAGGGCCCATCCGTCTTCCCCCTGGCGCCCT
GCTCCAGGAGCACCTCCGAGAGCACAGCCGCCCTGGGCTGCCTGGTCAAG
GACTACTTCCCCGAACCGGTGACGGTGTCGTGGAACTCAGGCGCCCTGAC
CAGCGGCGTGCACACCTTCCCGGCTGTCCTACAGTCCTCAGGACTCTACT
CCCTCAGCAGCGTGGTGACCGTGCCCTCCAGCAGCTTGGGCACGAAGACC
TACACCTGCAACGTAGATCACAAGCCCAGCAACACCAAGGTGGACAAGAG
AGTTGAGTCCAAATATGGTCCCCCATGCCCACCATGCCCAGCACCTGAGT
TCCTGGGGGGACCATCAGTCTTCCTGTTCCCCCCAAAACCCAAGGACACT
CTCATGATCTCCCGGACCCCTGAGGTCACGTGCGTGGTGGTGGACGTGAG
CCAGGAAGACCCCGAGGTCCAGTTCAACTGGTACGTGGATGGCGTGGAGG
TGCATAATGCCAAGACAAAGCCGCGGGAGGAGCAGTTCAACAGCACGTAC
CGTGTGGTCAGCGTCCTCACCGTCCTGCACCAGGACTGGCTGAACGGCAA
GGAGTACAAGTGCAAGGTCTCCAACAAAGGCCTCCCGTCCTCCATCGAGA
AAACCATCTCCAAAGCCAAAGGGCAGCCCCGAGAGCCACAGGTGTACACC
CTGCCCCCATCCCAGGAGGAGATGACCAAGAACCAGGTCAGCCTGACCTG
CCTGGTCAAAGGCTTCTACCCCAGCGACATCGCCGTGGAGTGGGAGAGCA
ATGGGCAGCCGGAGAACAACTACAAGACCACGCCTCCCGTGCTGGACTCC
GACGGCTCCTTCTTCCTCTACAGCAGGCTAACCGTGGACAAGAGCAGGTG
GCAGGAGGGGAATGTCTTCTCATGCTCCGTGATGCATGAGGCTCTGCACA
ACCACTACACAGAAGAGCCTCTCCCTGTCTCTGGGTAAATGA

| 32 | V_H LAG3.1 a.a. | |

TRANSLATION\OF\LAG3.1HC
QVQLQQWGAGLLKPSETLSLTCAVYGGSFSDYYWNWIRQPPGKGLEWIGE
INHNGNTNSNPSLKSRVTLSLDTSKNQFSLKLRSVTAADTAVYYCAFGYS
DYEYNWFDPWGQGTLVTVSSASTKGPSVFPLAPCSRSTSESTAALGCLVK
DYFPEPVTVSWNSGALTSGVHTFPAVLQSSGLYSLSSVVTVPSSSLGTKT
YTCNVDHKPSNTKVDKRVESKYGPPCPPCPAPEFLGGPSVFLFPPKPKDT
LMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDS
DGSFFLYSRLTVDKSRWQEGNVFSCSVMHEALHNHYTQKSLSLSLGK*

| 33 | V_L LAG3.1 n.a. | |

LAG3.1LC
GAAATTGTGTTGACACAGTCTCCAGCCACCCTGTCTTTGTCTCCAGGGGA
AAGAGCCACCCTCTCCTGCAGGGCCAGTCAGAGTATTAGCAGCTACTTAG
CCTGGTACCAACAGAAACCTGGCCAGGCTCCCAGGCTCCTCATCTATGAT
GCATCCAACAGGGCCACTGGCATCCCAGCCAGGTTCAGTGGCAGTGGGTC
TGGGACAGACTTCACTCTCACCATCAGCAGCCTAGAGCCTGAAGATTTTG
CAGTTTATTACTGTCAGCAGCGTAGCAACTGGCCTCTCACTTTTGGCCAG
GGGACCAACCTGGAGATCAAACGTACGGTGGCTGCACCATCTGTCTTCAT
CTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTG
GATAACGCCCTCCAATCGGGTAACTCCCAGGAGAGTGTCACAGAGCAGGA
CAGCAAGGACAGCACCTACAGCCTCAGCAGCACCCTGACGCTGAGCAAAG
CAGACTACGAGAAACACAAAGTCTACGCCTGCGAAGTCACCCATCAGGGC
CTGAGCTCGCCCGTCACAAAGAGCTTCAACAGGGGAGAGTGTTAG

| 34 | V_L LAG3.1 a.a. | |

TRANSLATION\OF\LAG3.1LC
EIVLTQSPATLSLSPGERATLSCRASQSISSYLAWYQQKPGQAPRLLIYD
ASNRATGIPARFSGSGSGTDFTLTISSLEPEDFAVYYCQQRSNWPLTFGQ
GTNLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC*

| 35 | V_H LAG3.5 a.a. | |

LAG3.5 heavy chain sequence-complete
QVQLQQWGAGLLKPSETLSLTCAVYGGSFSDYYWNWIRQPPGKGLEWIGE
INHRGSTNSNPSLKSRVTLSLDTSKNQFSLKLRSVTAADTAVYYCAFGYS
DYEYNWFDPWGQGTLVTVSSASTKGPSVFPLAPCSRSTSESTAALGCLVK
DYFPEPVTVSWNSGALTSGVHTFPAVLQSSGLYSLSSVVTVPSSSLGTKT
YTCNVDHKPSNTKVDKRVESKYGPPCPPCPAPEFLGGPSVFLFPPKPKDT
LMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDS
DGSFFLYSRLTVDKSRWQEGNVFSCSVMHEALHNHYTQKSLSLSLGK*

| 36 | V_H LAG3.5 n.a. | |

LAG3.5 heavy chain sequence-complete
caggtgcagctacagcagtggggcgcaggactgttgaagccttcggagac
cctgtccctcacctgcgctgtctatggtgggtccttcagtgattactact
ggaactggatccgccagccccagggaaggggctggagtggattggggaa
atcaatcatcgtggaagcaccaactccaacccgtccctcaagagtcgagt
caccctatcactagacacgtccaagaaccagttctccctgaagctgaggt
ctgtgaccgccgcggacacggctgtgtattactgtgcgtttggatatagt
gactacgagtacaactggttcgaccctggggccagggaaccctggtcac
cgtctcctcagctagcaccaagggcccatccgtcttccccctggcgccct
gctccaggagcacctccgagagcacagccgccctgggctgcctggtcaag
gactacttccccgaaccggtgacggtgtcgtggaactcaggcgccctgac
cagcggcgtgcacaccttcccggctgtcctacagtcctcaggactctact
ccctcagcagcgtggtgaccgtgccctccagcagcttgggcacgaagacc
tacacctgcaacgtagatcacaagcccagcaacaccaaggtggacaagag
agttgagtccaaatatggtccccatgcccaccatgcccagcacctgagt
tcctggggggaccatcagtcttcctgttccccccaaaacccaaggacact
ctcatgatctcccggacccctgaggtcacgtgcgtggtggtggacgtgag
ccaggaagaccccgaggtccagttcaactggtacgtggatggcgtggagg
tgcataatgccaagacaaagccgcgggaggagcagttcaacagcacgtac
cgtgtggtcagcgtcctcaccgtcctgcaccaggactggctgaacggcaa
ggagtacaagtgcaaggtctccaacaaaggcctcccgtcctccatcgaga
aaaccatctccaaagccaaagggcagccccgagagccacaggtgtacacc
ctgcccccatcccaggaggagatgaccaagaaccaggtcagcctgacctg
cctggtcaaaggcttctaccccagcgacatcgccgtggagtgggagagca
atgggcagccggagaacaactacaagaccacgcctcccgtgctggactcc
gacggctccttcttcctctacagcaggctaaccgtggacaagagcaggtg
gcaggaggggaatgtcttctcatgctccgtgatgcatgaggctctgcaca
accactacacagaagagcctctccctgtctctgggtaaatga

| 37 | V_L LAG3.5 a.a. | |

LAG3.5 kappa chain sequence-Complete
EIVLTQSPATLSLSPGERATLSCRASQSISSYLAWYQQKPGQAPRLLIYD
ASNRATGIPARFSGSGSGTDFTLTISSLEPEDFAVYYCQQRSNWPLTFGQ
GTNLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC*

SUMMARY OF SEQUENCE LISTING

| SEQ ID NO: | DESCRIPTION | SEQUENCE |
|---|---|---|
| 38 | V_L LAG3.5 n.a. | |

LAG3.5-kappa chain sequence-Complete
gaaattgtgttgacacagtctccagccaccctgtctttgtctccagggga
aagagccaccctctcctgcagggccagtcagagtattagcagctacttag
cctggtaccaacagaaacctggccaggctcccaggctcctcatctatgat
gcatccaacagggccactggcatcccagccaggttcagtggcagtggtc
tgggacagacttcactctcaccatcagcagcctagagcctgaagattttg
cagtttattactgtcagcagcgtagcaactggcctctcacttttggccag

SUMMARY OF SEQUENCE LISTING

| SEQ ID NO: | DESCRIPTION | SEQUENCE |
|---|---|---| gggaccaacctggagatcaaacgtacggtggctgcaccatctgtcttcat
cttcccgccatctgatgagcagttgaaatctggaactgcctctgttgtgt
gcctgctgaataacttctatcccagagaggccaaagtacagtggaaggtg
gataacgccctccaatcgggtaactcccaggagagtgtcacagagcagga
cagcaaggacagcacctacagcctcagcagcaccctgacgctgagcaaag
cagactacgagaaacacaaagtctacgcctgcgaagtcacccatcagggc
ctgagctcgcccgtcacaaagagcttcaacaggggagagtgttag

What is claimed:

1. A method of stimulating an immune response in a subject comprising administering to the subject an antibody, or antigen-binding portion thereof, such that an immune response in the subject is stimulated, wherein the antibody, or antigen-binding portion thereof, binds human LAG-3, and wherein the heavy chain CDR1, CDR2, and CDR3 regions comprise the amino acid sequences of SEQ ID NOs: 15, 16, and 17, respectively, and the light chain CDR1, CDR2, and CDR3 regions comprise the amino acid sequences of SEQ ID NOs: 18, 19, and 20, respectively.

2. A method of stimulating an immune response in a subject comprising administering to the subject an antibody, or antigen-binding portion thereof, such that an immune response in the subject is stimulated, wherein the antibody or antigen-binding portion thereof binds human LAG-3, and wherein the heavy chain variable region comprises the amino acid sequence of SEQ ID NO: 12 and the light chain variable region comprises the amino acid sequence of SEQ ID NO:14.

3. The method of claim 1 or 2, wherein the antibody is a full-length antibody.

4. The method of claim 1 or 2, wherein the antibody, or antigen-binding portion thereof, is a human antibody.

5. The method of claim 1 or 2, wherein the antibody, or antigen-binding portion thereof, is an IgG4 isotype.

6. The method of claim 5, wherein the antibody is a full-length antibody.

7. The method of claim 1, wherein the antibody, or antigen-binding portion thereof, binds to human LAG-3 with a $K_D$ of $0.27 \times 10^{-9}$M or less.

8. The method of claim 1, wherein the antibody, or antigen-binding portion thereof, exhibits one or a combination of the following properties:

(a) binding to monkey LAG-3;
(b) lack of binding to mouse LAG-3;
(c) binding to LAG-3 major histocompatibility (MEW) class II molecules; or
(d) inhibits binding of LAG-3 to major histocompatibility (MEW) class II molecules.

9. A method of stimulating an immune response in a subject comprising administering to the subject an antibody such that an immune response in the subject is stimulated, wherein the antibody is a full-length IgG4 human monoclonal antibody that binds human LAG-3, and wherein the heavy chain variable region comprises the amino acid sequence of SEQ ID NO: 12 and the light chain variable region comprises the amino acid sequence of SEQ ID NO: 14.

10. The method of claim 1, wherein the subject is a tumor-bearing subject and an immune response against the tumor is stimulated.

11. The method of claim 1, wherein the subject is a virus-bearing subject and an immune response against the virus is stimulated.

12. The method of claim 1, wherein the immune response is an antigen-specific T cell response, such that an antigen-specific T cell response is stimulated.

13. The method of claim 12, wherein interleukin-2 production by the antigen-specific T cell is stimulated.

14. The method of claim 1, further comprising the step of administering at least one additional immunostimulatory antibody, or antigen-binding fragment thereof.

15. The method of claim 14, wherein the at least one immunostimulatory additional antibody, or antigen-binding fragment thereof, is an anti-PD-1 antibody, or antigen-binding fragment thereof.

16. The method of claim 14, wherein the at least one additional immunostimulatory antibody, or antigen-binding fragment thereof, is an anti-PD-L1 antibody, or antigen-binding fragment thereof.

17. The method of claim 14, wherein the at least one additional immunostimulatory antibody, or antigen-binding fragment thereof, is an anti-CTLA-4 antibody, or antigen-binding fragment thereof.

18. The method of claim 15, wherein the anti-PD-1 antibody, or antigen-binding fragment thereof, is selected from the group of antibodies consisting of nivolumab (MDX1106), lambrolizumab, and AMP514.

19. The method of claim 18, wherein the anti-PD-1 antibody, or antigen-binding fragment thereof, is nivolumab (MDX1106).

20. The method of claim 18 or 19, wherein the antibodies, or antigen-binding fragments thereof, are administered sequentially as separate compositions with each antibody in a pharmaceutically acceptable carrier.

21. The method of claim 18 or 19, wherein the antibodies, or antigen-binding fragments thereof, are administered concurrently as separate compositions with each antibody in a pharmaceutically acceptable carrier.

22. The method of claim 18 or 19, wherein the antibodies, or antigen-binding fragments thereof, are administered concurrently as a single composition in a pharmaceutically acceptable carrier.

23. The method of claim 16, wherein the anti-PD-L1 antibody, or antigen-binding fragment thereof, is selected from the group of antibodies consisting of MDX1105 (BMS-936559), MPDL3280A, and MEDI4736.

24. The method of claim 23, wherein the anti-PD-L1 antibody, or antigen-binding fragment thereof, is MDX1105 (BMS-936559).

25. The method of claim 23 or 24, wherein the antibodies, or antigen-binding fragments thereof, are administered sequentially as separate compositions with each antibody in a pharmaceutically acceptable carrier.

26. The method of claim 23 or 24, wherein the antibodies, or antigen-binding fragments thereof, are administered concurrently as separate compositions with each antibody in a pharmaceutically acceptable carrier.

27. The method of claim 23 or 24, wherein the antibodies, or antigen-binding fragments thereof, are administered concurrently as a single composition in a pharmaceutically acceptable carrier.

28. The method of claim 17, wherein the anti-CTLA-4 antibody, or antigen-binding fragment thereof, is selected from the group of antibodies consisting of ipilimumab (MDX010), the antibody produced by hybridoma A3.6B10 deposited under ATCC Accession No. HB-12318, the antibody produced by hybridoma A3.6B10 deposited under ATCC Accession No. HB-12319, and CP-675206.

29. The method of claim 28, wherein the anti-CTLA-4 antibody, or antigen-binding fragment thereof, is ipilimumab (MDX010).

30. The method of claim 28 or 29, wherein the antibodies, or antigen-binding fragments thereof, are administered sequentially as separate compositions with each antibody in a pharmaceutically acceptable carrier.

31. The method of claim 28 or 29, wherein the antibodies, or antigen-binding fragments thereof, are administered concurrently as separate compositions with each antibody in a pharmaceutically acceptable carrier.

32. The method of claim 28 or 29, wherein the antibodies, or antigen-binding fragments thereof, are administered concurrently as a single composition in a pharmaceutically acceptable carrier.

33. The method of claim 9, further comprising the step of administering at least one additional immunostimulatory antibody, or antigen-binding fragment thereof, wherein the immunostimulatory antibody, or antigen-binding fragment thereof, is nivolumab (MDX1106).

34. The method of claim 9, further comprising the step of administering at least one additional immunostimulatory antibody, or antigen-binding fragment thereof, wherein the immunostimulatory antibody, or antigen-binding fragment thereof, is ipilimumab (MDX010).

35. The method of claim 1, wherein the heavy chain comprises the amino acid sequence of SEQ ID NO: 35 and the light chain comprises the amino acid sequence of SEQ ID NO: 37.

36. The method of claim 2, wherein the heavy chain comprises the amino acid sequence of SEQ ID NO: 35 and the light chain comprises the amino acid sequence of SEQ ID NO: 37.

37. The method of claim 9, wherein the heavy chain comprises the amino acid sequence of SEQ ID NO: 35 and the light chain comprises the amino acid sequence of SEQ ID NO: 37.

* * * * *

UNITED STATES PATENT AND TRADEMARK OFFICE
CERTIFICATE OF CORRECTION

PATENT NO. : 10,266,591 B2
APPLICATION NO. : 15/296290
DATED : April 23, 2019
INVENTOR(S) : Longerg et al.

It is certified that error appears in the above-identified patent and that said Letters Patent is hereby corrected as shown below:

In the Claims

Column 84
Line 37, "(c) binding to LAG-3 major histocompatibility (MEW)" should read --(c) binding to LAG-3 major histocompatibility (MHC)--.

Column 84
Line 40, "(MEW) class II molecules." should read --(MHC) class II molecules.--.

Signed and Sealed this
Sixteenth Day of July, 2019

Andrei Iancu
*Director of the United States Patent and Trademark Office*

UNITED STATES PATENT AND TRADEMARK OFFICE
CERTIFICATE OF CORRECTION

PATENT NO. : 10,266,591 B2
APPLICATION NO. : 15/296290
DATED : April 23, 2019
INVENTOR(S) : Lonberg et al.

It is certified that error appears in the above-identified patent and that said Letters Patent is hereby corrected as shown below:

In the Specification

In Column 45, following Line 50, delete the text beginning with "Summary of Sequence Listing" to and ending in "tgttag," as identified in Column 50, Seq. 38, and insert the following text:

SUMMARY OF SEQUENCE LISTING

| SEQ ID NO: | DESCRIPTION | SEQUENCE |
|---|---|---|
| 1 | $V_H$ n.a. 25F7 (LAG3.1) | |

>1408_LAG-3_403_25F7.1_VH1_NT
CAGGTGCAGCTACAGCAGTGGGGCGCAGGACTGTTGAAGCCTTCGGAGACCCTGTCCCTCACCTGCGC
TGTCTATGGTGGGTCCTTCAGTGATTACTACTGGAACTGGATCCGCCAGCCCCCAGGGAAGGGGCTGGA
GTGGATTGGGGAAATCAATCATAATGGAAACACCAACTCCAACCCGTCCCTCAAGAGTCGAGTCACCCTA
TCACTAGACACGTCCAAGAACCAGTTCTCCCTGAAGCTGAGGTCTGTGACCGCCGCGGACACGGCTGTG
TATTACTGTGCGTTTGGATATAGTGACTACGAGTACAACTGGTTCGACCCCTGGGGCCAGGGAACCCTG
GTCACCGTCTCCTCA

| 2 | $V_H$ a.a. 25F7 | |

>1408_LAG-3_403_25F7.1_VH1_AA
QVQLQQWGAGLLKPSETLSLTCAVYGGSFSDYYWNWIRQPPGKGLEWIGEINHNGNTNSNPSLKSRVTLSL
DTSKNQFSLKLRSVTAADTAVYYCAFGYSDYEYNWFDPWGQGTLVTVSS

| 3 | $V_K$ n.a. 25F7 | |

>1408_LAG-3_403_25F7.1_VK1_NT
GAAATTGTGTTGACACAGTCTCCAGCCACCCTGTCTTTGTCTCCAGGGGAAAGAGCCACCCTCTCCTGCA
GGGCCAGTCAGAGTATTAGCAGCTACTTAGCCTGGTACCAACAGAAACCTGGCCAGGCTCCCAGGCTCC
TCATCTATGATGCATCCAACAGGGCCACTGGCATCCCAGCCAGGTTCAGTGGCAGTGGGTCTGGGACAG
ACTTCACTCTCACCATCAGCAGCCTAGAGCCTGAAGATTTTGCAGTTTATTACTGTCAGCAGCGTAGCAA
CTGGCCTCTCACTTTTGGCCAGGGGACCAACCTGGAGATCAAA

Signed and Sealed this
Seventeenth Day of March, 2020

Andrei Iancu
*Director of the United States Patent and Trademark Office*

| 4 | $V_K$ a.a. 25F7 | |

>1408_LAG-3_403_25F7.1_VK1_AA

EIVLTQSPATLSLSPGERATLSCRASQSISSYLAWYQQKPGQAPRLLIYDASNRATGIPARFSGSGSGTDFTLTI
SSLEPEDFAVYYCQQRSNWPLTFGQGTNLEIK

| 5 | $V_H$ CDR1 a.a. 25F7 | DYYWN |
|---|---|---|
| 6 | $V_H$ CDR2 a.a. 25F7 | EINHNGNTNSNPSLKS |
| 7 | $V_H$ CDR3 a.a. 25F7 | GYSDYEYNWFDP |
| 8 | $V_K$ CDR1 a.a. 25F7 | RASQSISSYLA |
| 9 | $V_K$ CDR2 a.a. 25F7 | DASNRAT |
| 10 | $V_K$ CDR3 a.a. 25F7 | QQRSNWPLT |
| 11 | $V_H$ n.a. LAG3.5 | |

$V_H$ n.a. LAG3.5 caggtgcagctacagcagtggggcgcaggactgttgaagccttcggagaccctgtccctcacctgcgctgtctatggtgggtccttcagtgattactactgga
actggatccgccagccccagggaaggggctggagtggattggggaaatcaatcatcgtggaagcaccaactccaacccgtccctcaagagtcgagtc
accctatcactagacacgtccaagaaccagttctccctgaagctgaggtctgtgaccgccgcggacacggctgtgtattactgtgcgtttggatatagtgact
acgagtacaactggttcgacccctgggggccagggaaccctggtcaccgtctcctca

| 12 | $V_H$ a.a. LAG3.5 | |

$V_H$ a.a. LAG3.5

QVQLQQWGAGLLKPSETLSLTCAVYGGSFSDYYWNWIRQPPGKGLEWIGE
INHRGSTNSNPSLKSRVTLSLDTSKNQFSLKLRSVTAADTAVYYCAFGYS
DYEYNWFDPWGQGTLVTVSS

| 13 | $V_K$ n.a. LAG3.5 | |

$V_K$ n.a. LAG3.5 gaaattgtgttgacacagtctccagccaccctgtctttgtctccaggggaaagagccaccctctcctgcagggccagtcagagtattagcagctacttagcctggtaccaacagaa acctggccaggctcccaggctcctcatctatgatgcatccaacagggccactggcatcccagccaggttcagtggcagtgggtctgggacagacttcactctcaccatcagcag cctagagcctgaagattttgcagtttattactgtcagcagcgtagcaactggcctctcacttttggccaggggaccaacctggagatcaaa

| 14 | $V_K$ a.a. LAG3.5 | |

$V_K$ a.a. LAG3.5

EIVLTQSPATLSLSPGERATLSCRASQSISSYLAWYQQKPGQAPRLLIYD
ASNRATGIPARFSGSGSGTDFTLTISSLEPEDFAVYYCQQRSNWPLTFGQ
GTNLEIK

| 15 | $V_H$ CDR1 a.a. LAG3.5 | DYYWN |
|---|---|---|
| 16 | $V_H$ CDR2 a.a. LAG3.5 | EINHRGSTNSNPSLKS |
| 17 | $V_H$ CDR3 a.a. LAG3.5 | GYSDYEYNWFDP |

| 18 | V$_K$ CDR1 a.a. LAG3.5 | RASQSISSYLA |
| --- | --- | --- |
| 19 | V$_K$ CDR2 a.a. LAG3.5 | DASNRAT |
| 20 | V$_K$ CDR3 a.a. LAG3.5 | QQRSNWPLT |
| 21 | LAG-3 epitope | PGHPLAPG |
| 22 | LAG-3 epitope | HPAAPSSW |
| 23 | LAG-3 epitope | PAAPSSWG |
| 24 | V$_H$ CDR2 a.a. LAG3.6 | EIIHSGSTNSNPSLKS |
| 25 | V$_H$ CDR2 a.a. LAG3.7 | EINHGGGTNSNPSLKS |
| 26 | V$_H$ CDR2 a.a. LAG3.8 | EINHIGNTNSNPSLKS |
| 27 | V$_H$ CDR2 a.a. HUMAN GERMLINE | GEINHSGSTNY |
| 28 | | (Gly$_4$-Ser)$_3$ |
| 29 | Human LAG-3 a.a. | | human LAG-3 a.a. sequence
MWEAQFLGLLFLQPLWVAPVKPLQPGAEVPVVWAQEGAPAQLPCSPTIPLQDLSLLRRAGVTWQHQPDSGP
PAAAPGHPLAPGPHPAAPSSWGPRPRRYTVLSVGPGGLRSGRLPLQPRVQLDERGRQRGDFSLWLRPARR
ADAGEYRAAVHLRDRALSCRLRLRLGQASMTASPPGSLRASDWVILNCSFSRPDRPASVHWFRNRGQGRVP
VRESPHHHLAESFLFLPQVSPMDSGPWGCILTYRDGFNVSIMYNLTVLGLEPPTPLTVYAGAGSRVGLPCRLP
AGVGTRSFLTAKWTPPGGGPDLLVTGDNGDFTLRLEDVSQAQAGTYTCHIHLQEQQLNATVTLAIITVTPKSF
GSPGSLGKLLCEVTPVSGQERFVWSSLDTPSQRSFSGPWLEAQEAQLLSQPWQCQLYQGERLLGAAVYFTE
LSSPGAQRSGRAPGALPAGHLLLFLTLGVLSLLLLVTGAFGFHLWRRQWRPRRFSALEQGIHPPQAQSKIEEL
EQEPEPEPEPEPEPEPEPEPEPEQL*

| 30 | V$_H$ CDR2 a.a. LAG3.2 | VIWYDGSNKYYADSVKG |
| --- | --- | --- |
| 31 | V$_H$ LAG3.1 n.a. | |

LAG3.1HC
CAGGTGCAGCTACAGCAGTGGGGCGCAGGACTGTTGAAGCCTTCGGAGACCCTGTCCCTCACCTGCGC
TGTCTATGGTGGGTCCTTCAGTGATTACTACTGGAACTGGATCCGCCAGCCCCCAGGGAAGGGGCTGGA
GTGGATTGGGGAAATCAATCATAATGGAAACACCAACTCCAACCCGTCCCTCAAGAGTCGAGTCACCCTA
TCACTAGACACGTCCAAGAACCAGTTCTCCCTGAAGCTGAGGTCTGTGACCGCCGCGGACACGGCTGTG
TATTACTGTGCGTTTGGATATAGTGACTACGAGTACAACTGGTTCGACCCCTGGGGCCAGGGAACCCTG
GTCACCGTCTCCTCAGCTAGCACCAAGGGCCCATCCGTCTTCCCCCTGGCGCCCTGCTCCAGGAGCACC
TCCGAGAGCACAGCCGCCCTGGGCTGCCTGGTCAAGGACTACTTCCCCGAACCGGTGACGGTGTCGTG
GAACTCAGGCGCCCTGACCAGCGGCGTGCACACCTTCCCGGCTGTCCTACAGTCCTCAGGACTCTACTC
CCTCAGCAGCGTGGTGACCGTGCCCTCCAGCAGCTTGGGCACGAAGACCTACACCTGCAACGTAGATCA
CAAGCCCAGCAACACCAAGGTGGACAAGAGAGTTGAGTCCAAATATGGTCCCCCATGCCCACCATGCCC
AGCACCTGAGTTCCTGGGGGGACCATCAGTCTTCCTGTTCCCCCCAAAACCCAAGGACACTCTCATGATC
TCCCGGACCCCTGAGGTCACGTGCGTGGTGGTGGACGTGAGCCAGGAAGACCCCGAGGTCCAGTTCAA
CTGGTACGTGGATGGCGTGGAGGTGCATAATGCCAAGACAAAGCCGCGGGAGGAGCAGTTCAACAGCA
CGTACCGTGTGGTCAGCGTCCTCACCGTCCTGCACCAGGACTGGCTGAACGGCAAGGAGTACAAGTGC
AAGGTCTCCAACAAAGGCCTCCCGTCCTCCATCGAGAAAACCATCTCCAAAGCCAAAGGGCAGCCCCGA
GAGCCACAGGTGTACACCCTGCCCCCATCCCAGGAGGAGATGACCAAGAACCAGGTCAGCCTGACCTG
CCTGGTCAAAGGCTTCTACCCCAGCGACATCGCCGTGGAGTGGGAGAGCAATGGGCAGCCGGAGAACA
ACTACAAGACCACGCCTCCCGTGCTGGACTCCGACGGCTCCTTCTTCCTCTACAGCAGGCTAACCGTGG
ACAAGAGCAGGTGGCAGGAGGGGAATGTCTTCTCATGCTCCGTGATGCATGAGGCTCTGCACAACCACT
ACACACAGAAGAGCCTCTCCCTGTCTCTGGGTAAATGA

CERTIFICATE OF CORRECTION (continued)
U.S. Pat. No. 10,266,591 B2

| 32 | V$_H$ LAG3.1 a.a. | |

TRANSLATION\OF\LAG3.1HC
QVQLQQWGAGLLKPSETLSLTCAVYGGSFSDYYWNWIRQPPGKGLEWIGEINHNGNTNSNPSLKSRVTLSL
DTSKNQFSLKLRSVTAADTAVYYCAFGYSDYEYNWFDPWGQGTLVTVSSASTKGPSVFPLAPCSRSTSESTA
ALGCLVKDYFPEPVTVSWNSGALTSGVHTFPAVLQSSGLYSLSSVVTVPSSSLGTKTYTCNVDHKPSNTKVD
KRVESKYGPPCPPCPAPEFLGGPSVFLFPPKPKDTLMISRTPEVTCVVVDVSQEDPEVQFNWYVDGVEVHNA
KTKPREEQFNSTYRVVSVLTVLHQDWLNGKEYKCKVSNKGLPSSIEKTISKAKGQPREPQVYTLPPSQEEMT
KNQVSLTCLVKGFYPSDIAVEWESNGQPENNYKTTPPVLDSDGSFFLYSRLTVDKSRWQEGNVFSCSVMHE
ALHNHYTQKSLSLSLGK*

| 33 | V$_L$ LAG3.1 n.a. | |

LAG3.1LC
GAAATTGTGTTGACACAGTCTCCAGCCACCCTGTCTTTGTCTCCAGGGGAAAGAGCCACCCTCTCCTGCA
GGGCCAGTCAGAGTATTAGCAGCTACTTAGCCTGGTACCAACAGAAACCTGGCCAGGCTCCCAGGCTCC
TCATCTATGATGCATCCAACAGGGCCACTGGCATCCCAGCCAGGTTCAGTGGCAGTGGGTCTGGGACAG
ACTTCACTCTCACCATCAGCAGCCTAGAGCCTGAAGATTTTGCAGTTTATTACTGTCAGCAGCGTAGCAA
CTGGCCTCTCACTTTTGGCCAGGGGACCAACCTGGAGATCAAACGTACGGTGGCTGCACCATCTGTCTT
CATCTTCCCGCCATCTGATGAGCAGTTGAAATCTGGAACTGCCTCTGTTGTGTGCCTGCTGAATAACTTCT
ATCCCAGAGAGGCCAAAGTACAGTGGAAGGTGGATAACGCCCTCCAATCGGGTAACTCCCAGGAGAGTG
TCACAGAGCAGGACAGCAAGGACAGCACCTACAGCCTCAGCAGCACCCTGACGCTGAGCAAAGCAGAC
TACGAGAAACACAAAGTCTACGCCTGCGAAGTCACCCATCAGGGCCTGAGCTCGCCCGTCACAAAGAGC
TTCAACAGGGGAGAGTGTTAG

| 34 | V$_L$ LAG3.1 a.a. | |

TRANSLATION\OF\LAG3.1LC
EIVLTQSPATLSLSPGERATLSCRASQSISSYLAWYQQKPGQAPRLLIYDASNRATGIPARFSGSGSGTDFTLTI
SSLEPEDFAVYYCQQRSNWPLTFGQGTNLEIKRTVAAPSVFIFPPSDEQLKSGTASVVCLLNNFYPREAKVQ
WKVDNALQSGNSQESVTEQDSKDSTYSLSSTLTLSKADYEKHKVYACEVTHQGLSSPVTKSFNRGEC*

| 35 | V$_H$ LAG3.5 a.a. | |

LAG3.5 heavy chain sequence - complete
QVQLQQWGAGLLKPSETLSLTCAVYGGSFSDYYWNWIRQPPGKGLEWIGE
INHRGSTNSNPSLKSRVTLSLDTSKNQFSLKLRSVTAADTAVYYCAFGYS
DYEYNWFDPWGQGTLVTVSSASTKGPSVFPLAPCSRSTSESTAALGCLVK
DYFPEPVTVSWNSGALTSGVHTFPAVLQSSGLYSLSSVVTVPSSSLGTKT
YTCNVDHKPSNTKVDKRVESKYGPPCPPCPAPEFLGGPSVFLFPPKPKDT
LMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDS
DGSFFLYSRLTVDKSRWQEGNVFSCSVMHEALHNHYTQKSLSLSLGK*

| 36 | V$_H$ LAG3.5 n.a. | |

LAG3.5 heavy chain sequence - complete
caggtgcagctacagcagtggggcgcaggactgttgaagccttcggagaccctgtccctcacctgcgctgtctatggtgggtccttcagtgattactactgga
actggatccgccagcccccagggaaggggctggagtggattgggggaaatcaatcatcgtggaagcaccaactccaacccgtccctcaagagtcgagtc
accctatcactagacacgtccaagaaccagttctccctgaagctgaggtctgtgaccgccgcggacacggctgtgtattactgtgcgtttggatatagtgact
acgagtacaactggttcgaccctggggccagggaacccggtcaccgtctcctcagctagcaccaagggcccatccgtcttccccctggcgccctgctc
caggagcacctccgagagcacagccgccctgggctgcctggtcaaggactacttccccgaaccggtgacggtgtcgtggaactcaggcgccctgacca
gcggcgtgcacaccttcccggctgtcctacagtcctcaggactctactccctcagcagcgtggtgaccgtgccctccagcagcttgggcacgaagacctac
acctgcaacgtagatcacaagcccagcaacaccaaggtggacaagagagttgagtccaaatatggtcccccatgcccaccatgcccagcacctgagtt
cctggggggaccatcagtcttcctgttcccccaaaacccaaggacactctcatgatctcccggacccctgaggtcacgtgcgtggtggtggacgtgagcc
aggaagaccccgaggtccagttcaactggtacgtggatggcgtggaggtgcataatgccaagacaaagccgcgggaggagcagttcaacagcacgt
accgtgtggtcagcgtcctcaccgtcctgcaccaggactggctgaacggcaaggagtacaagtgcaaggtctccaacaaaggcctcccgtcctccatcg
agaaaaccatctccaaagccaaagggcagccccgagagccacaggtgtacaccctgcccccatcccaggaggagatgaccaagaaccaggtcagc
ctgacctgcctggtcaaaggcttctacccagcgacatcgccgtggagtgggagagcaatgggcagccggagaacaactacaagaccacgcctcccg
tgctggactccgacggctccttcttcctctacagcaggctaaccgtggacaagagcaggtggcaggaggggaatgtcttctcatgctccgtgatgcatgag
gctctgcacaaccactacacacagaagagcctctccctgtctctgggtaaatga

| 37 | V$_L$ LAG3.5 a.a. | |

LAG3.5 kappa chain sequence - Complete
EIVLTQSPATLSLSPGERATLSCRASQSISSYLAWYQQKPGQAPRLLIYD
ASNRATGIPARFSGSGSGTDFTLTISSLEPEDFAVYYCQQRSNWPLTFGQ
GTNLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC*

| 38 | V$_L$ LAG3.5 n.a. | |

LAG3.5 - kappa chain sequence - Complete
Gaaattgtgttgacacagtctccagccaccctgtctttgtctccaggggaaagagccaccctctcctgcagggccagtcagagtattagcagctacttagcc
tggtaccaacagaaacctggccaggctcccaggctcctcatctatgatgcatccaacagggccactggcatcccagccaggttcagtggcagtgggtctg
ggacagacttcactctcaccatcagcagcctagagcctgaagattttgcagtttattactgtcagcagcgtagcaactggcctctcacttttggccaggggac
caacctggagatcaaacgtacggtggctgcaccatctgtcttcatcttcccgccatctgatgagcagttgaaatctggaactgcctctgttgtgtgcctgctgaa
taacttctatcccagagaggccaaagtacagtggaaggtggataacgccctccaatcgggtaactcccaggagagtgtcacagagcaggacagcaag
gacagcacctacagcctcagcagcaccctgacgctgagcaaagcagactacgagaaacacaaagtctacgcctgcgaagtcacccatcagggcctg
agctcgcccgtcacaaagagcttcaacaggggagagtgttag

SEQUENCE LISTING

<160> NUMBER OF SEQ ID NOS: 52

<210> SEQ ID NO 1
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(360)

<400> SEQUENCE: 1

```
cag gtg cag cta cag cag tgg ggc gca gga ctg ttg aag cct tcg gag      48
Gln Val Gln Leu Gln Gln Trp Gly Ala Gly Leu Leu Lys Pro Ser Glu
1               5                   10                  15 acc ctg tcc ctc acc tgc gct gtc tat ggt ggg tcc ttc agt gat tac      96
Thr Leu Ser Leu Thr Cys Ala Val Tyr Gly Gly Ser Phe Ser Asp Tyr
            20                  25                  30 tac tgg aac tgg atc cgc cag ccc cca ggg aag ggg ctg gag tgg att     144
Tyr Trp Asn Trp Ile Arg Gln Pro Pro Gly Lys Gly Leu Glu Trp Ile
        35                  40                  45 ggg gaa atc aat cat aat gga aac acc aac tcc aac ccg tcc ctc aag     192
Gly Glu Ile Asn His Asn Gly Asn Thr Asn Ser Asn Pro Ser Leu Lys
    50                  55                  60 agt cga gtc acc cta tca cta gac acg tcc aag aac cag ttc tcc ctg     240
Ser Arg Val Thr Leu Ser Leu Asp Thr Ser Lys Asn Gln Phe Ser Leu
65                  70                  75                  80 aag ctg agg tct gtg acc gcc gcg gac acg gct gtg tat tac tgt gcg     288
Lys Leu Arg Ser Val Thr Ala Ala Asp Thr Ala Val Tyr Tyr Cys Ala
                85                  90                  95 ttt gga tat agt gac tac gag tac aac tgg ttc gac ccc tgg ggc cag     336
Phe Gly Tyr Ser Asp Tyr Glu Tyr Asn Trp Phe Asp Pro Trp Gly Gln
            100                 105                 110 gga acc ctg gtc acc gtc tcc tca                                     360
Gly Thr Leu Val Thr Val Ser Ser
        115                 120
```

<210> SEQ ID NO 2
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Gln Val Gln Leu Gln Gln Trp Gly Ala Gly Leu Leu Lys Pro Ser Glu
1               5                   10                  15
```

```
Thr Leu Ser Leu Thr Cys Ala Val Tyr Gly Gly Ser Phe Ser Asp Tyr
         20                  25                  30

Tyr Trp Asn Trp Ile Arg Gln Pro Pro Gly Lys Gly Leu Glu Trp Ile
         35                  40                  45

Gly Glu Ile Asn His Asn Gly Asn Thr Asn Ser Asn Pro Ser Leu Lys
     50                  55                  60

Ser Arg Val Thr Leu Ser Leu Asp Thr Ser Lys Asn Gln Phe Ser Leu
65                   70                  75                  80

Lys Leu Arg Ser Val Thr Ala Ala Asp Thr Ala Val Tyr Tyr Cys Ala
                 85                  90                  95

Phe Gly Tyr Ser Asp Tyr Glu Tyr Asn Trp Phe Asp Pro Trp Gly Gln
             100                 105                 110

Gly Thr Leu Val Thr Val Ser Ser
         115                 120

<210> SEQ ID NO 3
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(321)

<400> SEQUENCE: 3 gaa att gtg ttg aca cag tct cca gcc acc ctg tct ttg tct cca ggg      48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt att agc agc tac      96
Glu Arg Ala Thr Leu Ser Cys Arg Ala Ser Gln Ser Ile Ser Ser Tyr
            20                  25                  30 tta gcc tgg tac caa cag aaa cct ggc cag gct ccc agg ctc ctc atc     144
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc     192
Tyr Asp Ala Ser Asn Arg Ala Thr Gly Ile Pro Ala Arg Phe Ser Gly
    50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc aac tgg cct ctc     288
Glu Asp Phe Ala Val Tyr Tyr Cys Gln Gln Arg Ser Asn Trp Pro Leu
                85                  90                  95 act ttt ggc cag ggg acc aac ctg gag atc aaa                         321
Thr Phe Gly Gln Gly Thr Asn Leu Glu Ile Lys
            100                 105

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30
```

```
Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys
            100                 105

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Tyr Tyr Trp Asn
1               5

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Ile Asn His Asn Gly Asn Thr Asn Ser Asn Pro Ser Leu Lys Ser
1               5                   10                  15

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Tyr Ser Asp Tyr Glu Tyr Asn Trp Phe Asp Pro
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ala Ser Gln Ser Ile Ser Ser Tyr Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 9

Asp Ala Ser Asn Arg Ala Thr
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Gln Arg Ser Asn Trp Pro Leu Thr
1               5

<210> SEQ ID NO 11
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
caggtgcagc tacagcagtg gggcgcagga ctgttgaagc cttcggagac cctgtccctc      60
acctgcgctg tctatggtgg gtccttcagt gattactact ggaactggat ccgccagccc    120
ccagggaagg ggctggagtg gattggggaa atcaatcatc gtggaagcac caactccaac    180
ccgtccctca agagtcgagt caccctatca ctagacacgt ccaagaacca gttctccctg    240
aagctgaggt ctgtgaccgc cgcggacacg gctgtgtatt actgtgcgtt tggatatagt    300
gactacgagt acaactggtt cgaccctgg ggccagggaa ccctggtcac cgtctcctca    360

<210> SEQ ID NO 12
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
                20                  25                  30

Tyr Trp Asn Trp Ile Arg Gln Pro Pro Gly Lys Gly Leu Glu Trp Ile
            35                  40                  45

Gly Glu Ile Asn His Arg Gly Ser Thr Asn Ser Asn Pro Ser Leu Lys
        50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser
        115                 120

<210> SEQ ID NO 13
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(321)

<400> SEQUENCE: 13

```
gaa att gtg ttg aca cag tct cca gcc acc ctg tct ttg tct cca ggg      48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt att agc agc tac      96
Glu Arg Ala Thr Leu Ser Cys Arg Ala Ser Gln Ser Ile Ser Ser Tyr
            20                  25                  30 tta gcc tgg tac caa cag aaa cct ggc cag gct ccc agg ctc ctc atc     144
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc     192
Tyr Asp Ala Ser Asn Arg Ala Thr Gly Ile Pro Ala Arg Phe Ser Gly
    50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc aac tgg cct ctc     288
Glu Asp Phe Ala Val Tyr Tyr Cys Gln Gln Arg Ser Asn Trp Pro Leu
                85                  90                  95 act ttt ggc cag ggg acc aac ctg gag atc aaa                         321
Thr Phe Gly Gln Gly Thr Asn Leu Glu Ile Lys
            100                 105
```

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys
            100                 105
```

<210> SEQ ID NO 15
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 15

Asp Tyr Tyr Trp Asn
1               5

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu Ile Asn His Arg Gly Ser Thr Asn Ser Asn Pro Ser Leu Lys Ser
1               5                   10                  15

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Tyr Ser Asp Tyr Glu Tyr Asn Trp Phe Asp Pro
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ala Ser Gln Ser Ile Ser Ser Tyr Leu Ala
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Ala Ser Asn Arg Ala Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Gln Arg Ser Asn Trp Pro Leu Thr
1               5
```

```
<210> SEQ ID NO 21
<211> LENGTH: 8
<212> TYPE: PRT
<213> ORGANISM: Homo sapiens

<400> SEQUENCE: 21

Pro Gly His Pro Leu Ala Pro Gly
1               5

<210> SEQ ID NO 22
<211> LENGTH: 8
<212> TYPE: PRT
<213> ORGANISM: Homo sapiens

<400> SEQUENCE: 22

His Pro Ala Ala Pro Ser Ser Trp
1               5

<210> SEQ ID NO 23
<211> LENGTH: 8
<212> TYPE: PRT
<213> ORGANISM: Homo sapiens

<400> SEQUENCE: 23

Pro Ala Ala Pro Ser Ser Trp Gly
1               5

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Ile Ile His Ser Gly Ser Thr Asn Ser Asn Pro Ser Leu Lys Ser
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Ile Asn His Gly Gly Gly Thr Asn Ser Asn Pro Ser Leu Lys Ser
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu Ile Asn His Ile Gly Asn Thr Asn Ser Asn Pro Ser Leu Lys Ser
1               5                   10                  15

<210> SEQ ID NO 27
<211> LENGTH: 11
<212> TYPE: PRT
```

<213> ORGANISM: Homo sapiens

<400> SEQUENCE: 27

Gly Glu Ile Asn His Ser Gly Ser Thr Asn Tyr
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Gly Gly Ser Gly Gly Gly Ser Gly Gly Gly Gly Ser
1               5                   10                  15

<210> SEQ ID NO 29
<211> LENGTH: 525
<212> TYPE: PRT
<213> ORGANISM: Homo sapiens

<400> SEQUENCE: 29

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
        50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
                100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
        130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
            275                 280                 285

Gly Thr Arg Ser Phe Leu Thr Ala Lys Trp Thr Pro Gly Gly Gly
        290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
            325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
            355                 360                 365

Cys Glu Val Thr Pro Val Ser Gly Gln Glu Arg Phe Val Trp Ser Ser
            370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
            405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
            435                 440                 445

His Leu Leu Leu Phe Leu Thr Leu Gly Val Leu Ser Leu Leu Leu Leu
            450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
            485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Gln Leu
            515                 520                 525

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Ile Trp Tyr Asp Gly Ser Asn Lys Tyr Tyr Ala Asp Ser Val Lys
1               5                   10                  15

Gly

<210> SEQ ID NO 31
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
caggtgcagc tacagcagtg gggcgcagga ctgttgaagc cttcggagac cctgtccctc    60
acctgcgctg tctatggtgg gtccttcagt gattactact ggaactggat ccgccagccc   120

```
ccagggaagg ggctggagtg gattggggaa atcaatcata atggaaacac caactccaac    180
ccgtccctca agagtcgagt caccctatca ctagacacgt ccaagaacca gttctccctg    240
aagctgaggt ctgtgaccgc cgcggacacg gctgtgtatt actgtgcgtt tggatatagt    300
gactacgagt acaactggtt cgaccccctgg ggccagggaa ccctggtcac cgtctcctca    360
gctagcacca agggcccatc cgtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacctgca acgtagatca caagcccagc aacaccaagg tggacaagag agttgagtcc    660
aaatatggtc ccccatgccc accatgccca gcacctgagt tcctgggggg accatcagtc    720
ttcctgttcc ccccaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtct ccaacaaagg cctcccgtcc tccatcgaga aaaccatctc caaagccaaa    1020
gggcagcccc gagagccaca ggtgtacacc ctgcccccat cccaggagga gatgaccaag    1080
aaccaggtca gcctgacctg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggcta accgtggaca agagcaggtg gcaggagggg    1260
aatgtcttct catgctccgt gatgcatgag gctctgcaca accactacac acagaagagc    1320
ctctccctgt ctctgggtaa atga                                          1344
```

<210> SEQ ID NO 32
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Asn Gly Asn Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
```

```
                130             135             140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
            435                 440                 445

<210> SEQ ID NO 33
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
gaaattgtgt tgacacagtc tccagccacc ctgtctttgt ctccagggga aagagccacc      60
ctctcctgca gggccagtca gagtattagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctctcac ttttggccag     300
```

```
gggaccaacc tggagatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg ataacgccc  tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645
```

<210> SEQ ID NO 34
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 35
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Gln Val Gln Leu Gln Gln Trp Gly Ala Gly Leu Leu Lys Pro Ser Glu
1               5                   10                  15
```

Thr Leu Ser Leu Thr Cys Ala Val Tyr Gly Gly Ser Phe Ser Asp Tyr
            20                  25                  30

Tyr Trp Asn Trp Ile Arg Gln Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 36
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

| | |
|---|---|
| caggtgcagc tacagcagtg gggcgcagga ctgttgaagc cttcggagac cctgtccctc | 60 |
| acctgcgctg tctatggtgg gtccttcagt gattactact ggaactggat ccgccagccc | 120 |
| ccagggaagg ggctggagtg gattggggaa atcaatcatc gtggaagcac caactccaac | 180 |
| ccgtccctca agagtcgagt caccctatca ctagacacgt ccaagaacca gttctccctg | 240 |
| aagctgaggt ctgtgaccgc cgcggacacg gctgtgtatt actgtgcgtt tggatatagt | 300 |
| gactacgagt acaactggtt cgaccccctgg ggccagggaa ccctggtcac cgtctcctca | 360 |
| gctagcacca agggcccatc cgtcttcccc ctggcgccct gctccaggag cacctccgag | 420 |
| agcacagccg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacgaagacc | 600 |
| tacacctgca acgtagatca caagcccagc aacaccaagg tggacaagag agttgagtcc | 660 |
| aaatatggtc cccatgccc accatgccca gcacctgagt tcctgggggg accatcagtc | 720 |
| ttcctgttcc ccccaaaacc caaggacact ctcatgatct cccggacccc tgaggtcacg | 780 |
| tgcgtggtgg tggacgtgag ccaggaagac cccgaggtcc agttcaactg gtacgtggat | 840 |
| ggcgtggagg tgcataatgc caagacaaag ccgcgggagg agcagttcaa cagcacgtac | 900 |
| cgtgtggtca gcgtcctcac cgtcctgcac caggactggc tgaacggcaa ggagtacaag | 960 |
| tgcaaggtct ccaacaaagg cctcccgtcc tccatcgaga aaaccatctc caaagccaaa | 1020 |
| gggcagcccc gagagccaca ggtgtacacc ctgcccccat cccaggagga gatgaccaag | 1080 |
| aaccaggtca gcctgacctg cctggtcaaa ggcttctacc ccagcgacat cgccgtggag | 1140 |
| tgggagagca atgggcagcc ggagaacaac tacaagacca cgcctcccgt gctggactcc | 1200 |
| gacggctcct tcttcctcta cagcaggcta accgtggaca agagcaggtg gcaggagggg | 1260 |
| aatgtcttct catgctccgt gatgcatgag gctctgcaca accactacac acagaagagc | 1320 |
| ctctccctgt ctctgggtaa atga | 1344 |

<210> SEQ ID NO 37
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65              70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 38
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gaaattgtgt tgacacagtc tccagccacc ctgtctttgt ctccagggga aagagccacc    60
ctctcctgca gggccagtca gagtattagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctctcac ttttggccag   300
gggaccaacc tggagatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac agggagagt gttag   645

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Pro Val Gly Val Val

```
1               5
```

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Gly Glu Ile Asn His Arg Gly Ser Thr Asn Ser Asn Pro
1               5                   10
```

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Gly Glu Ile Asn His Asn Gly Asn Thr Asn Ser
1               5                   10
```

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Gly Glu Ile Asn His Arg Gly Ser Thr Asn Ser
1               5                   10
```

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Gly Glu Ile Ile His Ser Gly Ser Thr Asn Ser
1               5                   10
```

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Gly Glu Ile Asn His Gly Gly Gly Thr Asn Ser
1               5                   10
```

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Gly Glu Ile Asn His Ile Gly Asn Thr Asn Ser
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Isomerized residue

<400> SEQUENCE: 46

Ile Asn His Asp Gly Asn Thr Asn Ser Asn Pro Ser Leu Lys
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ile Asn His Asp Gly Asn Thr Asn Ser Asn Pro Ser Leu Lys
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ile Asn His Asn Gly Asn Thr Asp Ser Asn Pro Ser Leu Lys
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ile Asp His Asn Gly Asn Thr Asn Ser Asn Pro Ser Leu Lys
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Isomerized residue

```
<400> SEQUENCE: 50

Ile Asn His Arg Gly Ser Thr Asp Ser Asn Pro Ser Leu Lys
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ile Asn His Arg Gly Ser Thr Asn Ser Asn Pro Ser Leu Lys
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Isomerized residue

<400> SEQUENCE: 52

Ile Asp His Arg Gly Ser Thr Asp Ser Asn Pro Ser Leu Lys
1               5                   10
```